(12) United States Patent
Ray et al.

(10) Patent No.: US 7,994,211 B2
(45) Date of Patent: Aug. 9, 2011

(54) BICYCLO[2.2.1]HEPT-7-YLAMINE DERIVATIVES AND THEIR USES

(75) Inventors: Nicholas Charles Ray, Harlow (GB); Andrew Stephen Robert Jennings, Harlow (GB)

(73) Assignee: Argenta Discovery Limited, Essex (GB)

(*) Notice: Subject to any disclaimer, the term of this patent is extended or adjusted under 35 U.S.C. 154(b) by 136 days.

(21) Appl. No.: 12/063,212

(22) PCT Filed: Aug. 8, 2006

(86) PCT No.: PCT/GB2006/002957
§ 371 (c)(1),
(2), (4) Date: Feb. 7, 2008

(87) PCT Pub. No.: WO2007/017670
PCT Pub. Date: Feb. 15, 2007

(65) Prior Publication Data
US 2010/0144852 A1  Jun. 10, 2010

(30) Foreign Application Priority Data

Aug. 8, 2005 (GB) .................................. 0516314.2
Jul. 10, 2006 (GB) .................................. 0613709.5

(51) Int. Cl.
| | |
|---|---|
| A61K 31/381 | (2006.01) |
| A61K 31/24 | (2006.01) |
| C07C 269/00 | (2006.01) |
| C07D 409/06 | (2006.01) |
| A61P 11/06 | (2006.01) |
| A61P 1/00 | (2006.01) |
| A61P 9/10 | (2006.01) |

(52) U.S. Cl. ............. 514/444; 560/27; 549/59; 514/535
(58) Field of Classification Search .................. None
See application file for complete search history.

(56) References Cited

U.S. PATENT DOCUMENTS
4,353,922 A   10/1982   Pfister
(Continued)

FOREIGN PATENT DOCUMENTS
EP   0418716 A1   3/1991
(Continued)

OTHER PUBLICATIONS

Carroll et al., "Synthesis and Muscarinic Receptor Activity of Ester Derivatives of 2-Substituted 2-Azabicyclo[2.2.1]heptan-5-ol and -6-ol", *J. Med. Chem.* 35:2184-2191 (1992).

(Continued)

*Primary Examiner* — Brandon J Fetterolf
*Assistant Examiner* — Dennis Heyer

(74) *Attorney, Agent, or Firm* — Connolly Bove Lodge & Hutz LLP

(57) ABSTRACT

Compounds of formula (I) have muscarinic M3 receptor modulating activity; Formula (I) wherein A is an oxygen atom or group $—N(R^{12})—$; (i) $R^1$ is $C_1$-$C_6$-alkyl or a hydrogen atom; and $R^2$ is a hydrogen atom or a group $—R^5$, $—Z—Y—R^5$, $—Z—NR^9R^{10}$; $—Z—CO—NR^9R^{10}$; $—Z—NR^9—CO—R^5$; or $—Z—CO_2H$; and $R^3$ is a lone pair, or $C_1$-$C_6$-alkyl in which case the nitrogen atom to which it is attached is a quaternary nitrogen and carries a positive charge; or (ii) $R^1$ and $R^3$ together with the nitrogen to which they are attached form a heterocycloalkyl ring, and $R^2$ is a hydrogen atom; or a group $—R^5$, $—Z—Y—R^5$, $—Z—NR^9R^{10}$, $—Z—CO—NR^9R^{10}$, $—Z—NR^9—CO—R^5$, or $—Z—CO_2H$, in which cases the nitrogen atom to which it is attached is a quaternary nitrogen and carries a positive charge; or (iii) $R^1$ and $R^2$ together with the nitrogen to which they are attached form a heterocycloalkyl ring, said ring being substituted by a group $—Y—R^5$, $—Z—Y—R^5$, $—Z—NR^9R^{10}$; $—Z—CO—NR^9R^{10}$; $—Z—NR^9—CO—R^5$; or $—Z—CO_2H$ and $R^3$ is a lone pair, or $C_1$-$C_6$-alkyl in which case the nitrogen atom to which it is attached is a quaternary nitrogen and carries a positive charge; $R^4$ is a group of formula (a), (b), (c) or (d); is an $C_1$-$C_6$-alkyl, aryl, aryl-fused-cycloalkyl, aryl-fused-heterocycloalkyl, heteroaryl, aryl($C_1$-$C_8$-alkyl)-, heteroaryl($C_1$-$C_8$-alkyl)-, cycloalkyl or heterocycloalkyl group, and the remaining variables are as defined in the specification.

(I)

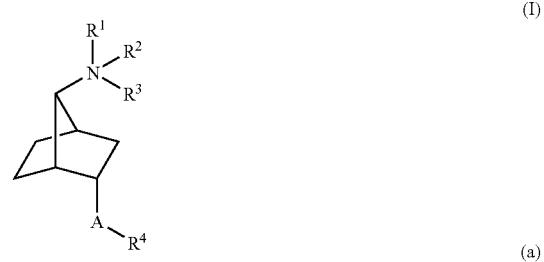

(a)

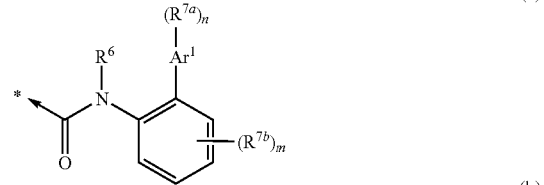

(b)

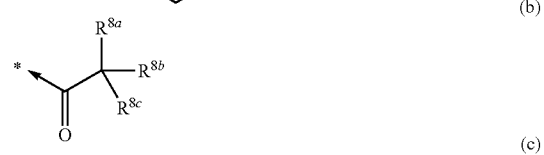

(c)

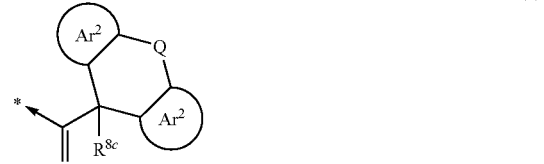

(d)

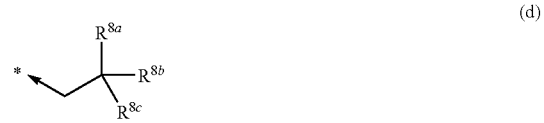

9 Claims, 1 Drawing Sheet

U.S. PATENT DOCUMENTS

Figure 1:
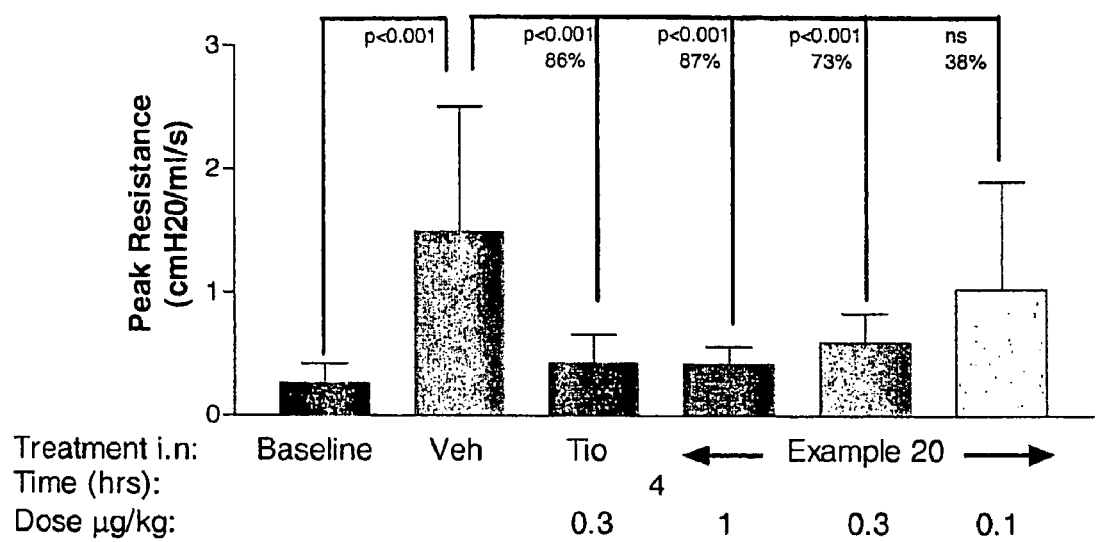

| | | |
|---|---|---|
| 5,610,163 A | 3/1997 | Banholzer et al. |
| 2005/0025718 A1 | 2/2005 | Meade et al. |
| 2005/0209272 A1 | 9/2005 | Forner et al. |

FOREIGN PATENT DOCUMENTS

| | | |
|---|---|---|
| WO | WO-02/060532 A1 | 8/2002 |
| WO | WO-02/060533 A2 | 8/2002 |
| WO | WO-03/087097 A1 | 10/2003 |
| WO | WO-2004/074246 A2 | 9/2004 |
| WO | WO-2004/089892 A2 | 10/2004 |
| WO | WO-2004/105759 A2 | 12/2004 |
| WO | WO-2005/111004 A1 | 11/2005 |
| WO | WO-2006/017768 A2 | 2/2006 |
| WO | WO-2006/023457 A1 | 3/2006 |
| WO | WO-2006/023460 A2 | 3/2006 |
| WO | WO-2006/035282 A2 | 4/2006 |
| WO | WO-2006/035303 A1 | 4/2006 |
| WO | WO 2006//048225 A1 | 5/2006 |
| WO | WO-2010/071581 A1 | 6/2010 |
| WO | WO-2010/071582 A1 | 6/2010 |

OTHER PUBLICATIONS

Pfister et al., "Synthesis and Bronchodilator Activity of *endo*-2-(2-Cyclo-penty1-2-hydroxy-2-phenyl)acetoxy-7-methyl-7-azabicyclo-[2.2.1]heptane Methobromide, a Potent and Long-Acting Anticholinergic Agent", *J. Pharm. Sci.* 74(2):208-210 (1985).

Gross et al., "Anticholinergic, Antimuscarinic Bronchodilators", *Am. Rev. Respir. Dis.*, vol. 129, pp. 856-870 (1984).

Gross et al., "Cholinergic Bronchomotor Tone in COPD*: Estimates of its Amount in Comparison with That in Normal Subjects", *Chest*, vol. 96, No. 5, pp. 984-987 (1989).

Caulfield, Muscarinic Receptors-Characterization, Coupling and Function, *Pharmac. Ther.*, vol. 58, pp. 319-379 (1993).

Fryer et al., "Muscarinic Receptors and Control of Airway Smooth Muscle", *Am. J. Respir. Crit. Care Med.*, vol. 158, pp. S154-S160 (1998).

Fryer et al., "Effects of Inflammatory Cells on Neuronal $M_2$ Muscarinic Receptor Function in the Lung", *Life Sciences*, vol. 64, Nos. 6/7, pp. 449-455 (1999).

Pauwels et al., "Global Strategy for the Diagnosis, Management, and Prevention of Chronic Obstruction Pulmonary Disease", *Am. J. Respir. Crit. Care Med.*, vol. 163, pp. 1256-1276 (2001).

Lee et al., "Selective Muscarinic Receptor Antagonists for Airway Diseases", *Current Opinion in Pharmacology*, vol. 1, pp. 223-229 (2001).

Cazzola et al., "Ultra Long Acting β-Agonists in Development for Asthma and Chronic Obstructive Pulmonary Disease", *Expert Opin. Investig. Drugs*, vol. 14, No. 7, pp. 775-783 (2005).

BICYCLO[2.2.1]HEPT-7-YLAMINE DERIVATIVES AND THEIR USES

CROSS-REFERENCE TO RELATED APPLICATIONS

This application is a national phase application under 35 U.S.C. §371 of PCT International Application No. PCT/GB2006/002957, filed Aug. 8, 2006, which claims the benefit of United Kingdom Application Serial No. 0516314.2, filed Aug. 8, 2005 and United Kingdom Application Serial No. 0613709.5, filed Jul. 10, 2006. Each of these prior applications is incorporated herein by reference in its entirety.

FIELD OF THE INVENTION

This invention relates to bicyclo[2.2.1]hept-7-ylamine derivatives, pharmaceutical compositions, methods for their preparation and use in the treatment of M3 muscarinic receptor mediated diseases, for example respiratory diseases.

BACKGROUND TO THE INVENTION

Anti-cholinergic agents prevent the passage of, or effects resulting from the passage of, impulses through the parasympathetic nerves. This is a consequence of the ability of such compounds to inhibit the action of acetylcholine (Ach) by blocking its binding to the muscarinic cholinergic receptors.

There are five subtypes of muscarinic acetylcholine receptors (mAChRs), termed M1-M5, and each is the product of a distinct gene and each displays unique pharmacological properties, mAChRs are widely distributed in vertebrate organs, and these receptors can mediate both inhibitory and excitatory actions. For example, in smooth muscle found in the airways, bladder and gastrointestinal tract, M3 mAChRs mediate contractile responses (reviewed by Caulfield, 1993, Pharmac. Ther., 58, 319-379).

In the lungs, muscarinic receptors M1, M2 and M3 have been demonstrated to be important and are localized to the trachea, the bronchi, submucosal glands and parasympathetic ganglia (reviewed in Fryer and Jacoby, 1998, Am J Resp Crit Care Med., 158 (5 part 3) S 154-160). M3 receptors on airway smooth muscle mediate contraction and therefore bronchoconstriction. Stimulation of M3 receptors localised to submucosal glands results in mucus secretion.

Increased signalling through muscarinic acetylcholine receptors has been noted in a variety of different pathophysiological states including asthma and COPD. In COPD, vagal tone may either be increased (Gross et al. 1989, Chest; 96:984-987) and/or may provoke a higher degree of obstruction for geometric reasons if applied on top of oedematous or mucus-laden airway walls (Gross et al. 1984, Am Rev Respir Dis; 129:856-870). In addition, inflammatory conditions can lead to a loss of inhibitory M2 receptor activity which results in increased levels of acetylcholine release following vagal nerve stimulation (Fryer et al, 1999, Life Sci., 64, (6-7) 449-455). The resultant increased activation of M3 receptors leads to enhanced airway obstruction. Thus the identification of potent muscarinic receptor antagonists would be useful for the therapeutic treatment of those disease states where enhanced M3 receptor activity is implicated. Indeed, contemporary treatment strategies currently support regular use of M3 antagonist bronchodilators as first-line therapy for COPD patients (Pauwels et al. 2001, Am Rev Respir Crit. Care Med; 163:1256-1276)

Incontinence due to bladder hypercontractility has also been demonstrated to be mediated through increased stimulation of M3 mAChRs. Thus M3 mAChR antagonists may be useful as therapeutics in these mAChR-mediated diseases.

Despite the large body of evidence supporting the use of anti-muscarinic receptor therapy for treatment of airway disease states, relatively few anti-muscarinic compounds are in use in the clinic for pulmonary indications. Thus, there remains a need for novel compounds that are capable of causing blockade at M3 muscarinic receptors, especially those compounds with a long duration of action, enabling a once-daily dosing regimen. Since muscarinic receptors are widely distributed throughout the body, the ability to deliver anticholinergic drugs directly to the respiratory tract is advantageous as it allows lower doses of the drug to be administered. The design and use of topically active drugs with a long duration of action and that are retained on the receptor or in the lung would allow reduction of unwanted side effects that could be seen with systemic administration of the same drugs.

Tiotropium (Spiriva™) is a long-acting muscarinic antagonist currently marketed for the treatment of chronic obstructive pulmonary disease, administered by the inhaled route.

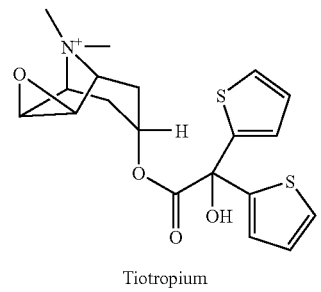

Tiotropium

Additionally ipratropium is a muscarinic antagonist marketed for the treatment of COPD.

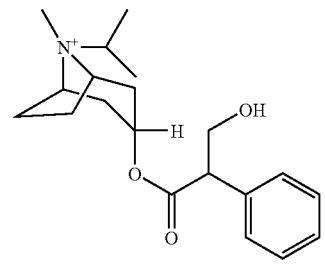

Ipratropium

Other muscarinic receptor modulators have been referred to. For example: U.S. Pat. No. 4,353,922 describes muscarinic modulators based upon a [2.2.1]azabicycloheptane ring system. EP418716 and US005610163 describe various [3.2.1]azabicyclooctane ring systems. WO06/017768 describes [3.3.1]azabicyclononane ring systems. [2.2.2] azabicyclooctane systems (quinuclidines) have been previously described, for example in US2005/0209272 and WO06/048225. [3.1.0]azabicyclohexane systems have been described in, for example in WO06/035282. [3.2.1]azabicyclooctane systems have been described in for example WO06/035303.

The class of β2 adrenergic receptor agonists is well known. Many known β2-agonists, in particular, long-acting β2-agonists such as salmeterol and formoterol, have a role in the treatment of asthma and COPD. These compounds are also generally administered by inhalation. Compounds currently under evaluation as once-daily β2 agonists are described in Expert Opin. Investig. Drugs 14 (7), 775-783 (2005). A well known β2-agonist pharmacophore is the moiety:

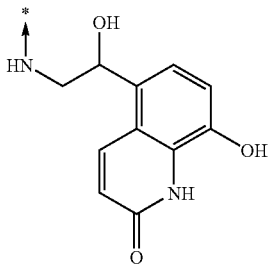

Also known in the art are pharmaceutical compositions that contain both a muscarinic antagonist and a β2-agonist for use in the treatment of respiratory disorders. For example, US2005/0025718 describes a β2-agonist in combination with tiotropium, oxotropium, ipratropium and other muscarinic antagonists; WO02/060532 describes the combination of ipratropium with β2-agonists and WO02/060533 describes the combination of oxotropium with β2-agonists. Other M3 antagonist/β2-agonist combinations are described in WO04/105759 and WO03/087097.

Also known in the art are compounds possessing both muscarinic receptor antagonist and β2-agonist activity present in the same molecule. Such bifunctional molecules provide bronchodilation through two separate modes of action whilst possessing single molecule pharmacokinetics. Such a molecule should be easier to formulate for therapeutic use as compared to two separate compounds and could be more easily co-formulated with a third active ingredient, for example a steroid. Such molecules are described in for example, WO04/074246, WO04/089892, WO05/111004, WO06/023457 and WO06/023460, all of which use different linker radicals for covalently linking the M3 antagonist to the β2-agonist, indicating that the structure of the linker radical is not critical to preserve both activities. This is not surprising since the molecule is not required to interact with the M3 and β2 receptors simultaneously.

SUMMARY OF THE INVENTION

According to the invention, there is provided a compound of formula (I):

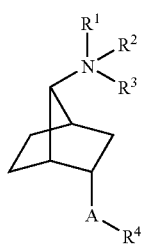

(I)

wherein
A is an oxygen atom or group —N($R^{12}$)—;
(i) $R^1$ is $C_1$-$C_6$-alkyl or a hydrogen atom; and $R^2$ is a hydrogen atom or a group —$R^5$, or a group, —Z—Y—$R^5$, or a group —Z—N$R^9R^{10}$; or a group —Z—CO—N$R^9R^{10}$; or a group —Z—N$R^9$—CO—$R^5$; or a group —Z—CO$_2$—$R^5$; or a group —Z—CO$_2$H; and $R^3$ is a lone pair, or $C_1$-$C_6$-alkyl in which case the nitrogen atom to which it is attached is a quaternary nitrogen and carries a positive charge; or (ii) $R^1$ and $R^3$ together with the nitrogen to which they are attached form a heterocycloalkyl ring, and $R^2$ is a hydrogen atom; or a group —$R^5$, or a group, —Z—Y—$R^5$, or a group —Z—N$R^9R^{10}$, or a group —Z—CO—N$R^9R^{10}$, or a group —Z—N$R^9$—CO—$R^5$, or a group —Z—CO$_2$—$R^5$, or a group —Z—CO$_2$H, in which cases the nitrogen atom to which it is attached is a quaternary nitrogen and carries a positive charge; or (iii) $R^1$ and $R^2$ together with the nitrogen to which they are attached form a heterocycloalkyl ring, said ring being substituted by a group —Y—$R^5$, or a group —Z—Y—$R^5$, or a group —Z—N$R^9R^{10}$; or a group —Z—CO—N$R^9R^{10}$; or a group —Z—N$R^9$—CO—$R^5$; or a group —Z—CO$_2$—$R^5$; or a group —Z—CO$_2$H and $R^3$ is a lone pair, or $C_1$-$C_6$-alkyl in which case the nitrogen atom to which it is attached is a quaternary nitrogen and carries a positive charge;
$R^4$ is selected from one of the groups of formula (a), (b), (c) or (d):

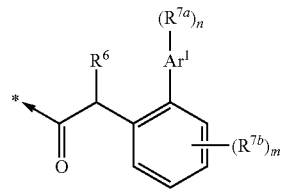

(a)

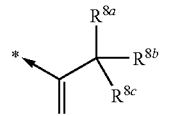

(b)

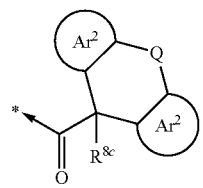

(c)

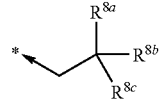

(d)

Z is a $C_1$-$C_{16}$-alkylene, $C_2$-$C_{16}$-alkenylene or $C_2$-$C_{16}$-alkynylene group;
Y is a bond or oxygen atom;
$R^6$ is an $C_1$-$C_6$-alkyl, aryl, aryl-fused-cycloalkyl, aryl-fused-heterocycloalkyl, heteroaryl, aryl($C_1$-$C_8$-alkyl)-, heteroaryl($C_1$-$C_8$-alkyl)-, cycloalkyl or heterocycloalkyl group;
$R^6$ is $C_1$-$C_6$-alkyl or a hydrogen atom;
$R^{7a}$ and $R^{7b}$ are a $C_1$-$C_6$-alkyl group or halogen;
n and m are independently 0, 1, 2 or 3;
$R^{8a}$ and $R^{8b}$ are independently selected from the group consisting of aryl, aryl-fused-heterocycloalkyl, heteroaryl, $C_1$-$C_6$-alkyl, cycloalkyl;
$R^{8c}$ is —OH, $C_1$-$C_6$-alkyl, hydroxy-$C_1$-$C_6$-alkyl, nitrile, a group CON$R^{8d}_2$ or a hydrogen atom;
$R^{8d}$ is $C_1$-$C_6$-alkyl or a hydrogen atom;

$R^9$ and $R^{10}$ are independently a hydrogen atom, $C_1$-$C_6$-alkyl, aryl, aryl-fused-heterocycloalkyl, aryl-fused-cycloalkyl, heteroaryl, aryl($C_1$-$C_6$-alkyl)-, or heteroaryl($C_1$-$C_6$-alkyl)-group; or $R^9$ and $R^{10}$ together with the nitrogen atom to which they are attached form a heterocyclic ring of 4-8 atoms, optionally containing a further nitrogen or oxygen atom;

$R^{12}$ is $C_1$-$C_6$-alkyl or a hydrogen atom;

$Ar^1$ is aryl, heteroaryl or cycloalkyl;

$Ar^2$ are independently aryl, heteroaryl or cycloalkyl; and

Q is an oxygen atom, —$CH_2$—, —$CH_2CH_2$— or a bond;

or a pharmaceutically acceptable salt, solvate, N-oxide or prodrug thereof.

In one subset of the compounds of the invention:

A is an oxygen atom or group —$N(R^{12})$—;

$R^1$ is $C_1$-$C_6$-alkyl or a hydrogen atom and $R^2$ is $C_1$-$C_6$-alkyl, a hydrogen atom or a group —Z—Y—$R^5$, or a group —Z—$NR^9R^{10}$; or $R^1$ and $R^2$ together with the nitrogen to which they are attached form a heterocycloalkyl ring;

$R^3$ is a lone pair; or $C_1$-$C_6$-alkyl, in which case the nitrogen atom to which it is attached is a quaternary nitrogen and carries a positive charge; or $R^1$ and $R^3$ together with the nitrogen to which they are attached form a heterocycloalkyl ring and $R^2$ is $C_1$-$C_6$-alkyl, in which case the nitrogen atom is quaternised and carries a positive charge;

$R^4$ is selected from one of the groups of formula (a) and (b):

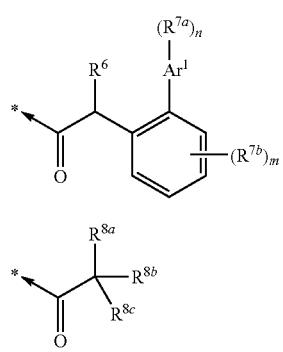

Z is a $C_1$-$C_8$-alkylene, $C_2$-$C_8$-alkenylene or $C_2$-$C_8$-alkynylene group;

Y is a bond or oxygen atom;

$R^5$ is an aryl, heteroaryl, aryl($C_1$-$C_8$-alkyl)-, or heteroaryl($C_1$-$C_8$-alkyl)-group;

$R^6$ is $C_1$-$C_6$-alkyl or a hydrogen atom;

$R^{7a}$ and $R^{7b}$ are independently a $C_1$-$C_6$-alkyl group or halogen;

n and m are independently 0, 1, 2 or 3;

$R^{8a}$ and $R^{8b}$ are independently selected from the group consisting of aryl, heteroaryl, $C_1$-$C_6$-alkyl, cycloalkyl;

$R^{8c}$ is —OH, $C_1$-$C_6$-alkyl, hydroxy-$C_1$-$C_6$-alkyl, or a hydrogen atom;

$R^9$ and $R^{10}$ are independently a hydrogen atom, $C_1$-$C_6$-alkyl, aryl, heteroaryl, aryl($C_1$-$C_6$-alkyl)-, or heteroaryl($C_1$-$C_6$-alkyl)-group; or $R^9$ and $R^{10}$ together with the nitrogen atom to which they are attached form a heterocyclic ring of 4-8 atoms, optionally containing a further nitrogen or oxygen atom; and $R^{12}$ is $C_1$-$C_6$-alkyl or a hydrogen atom.

Compounds of the invention exist in either the syn- or anti-forms;

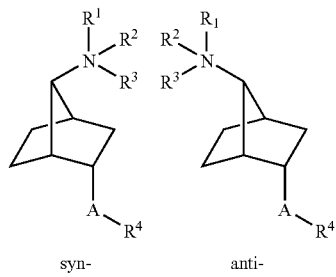

syn-    anti-

Compounds of the invention also exist with the group -$AR^4$ in either the exo or endo orientation;

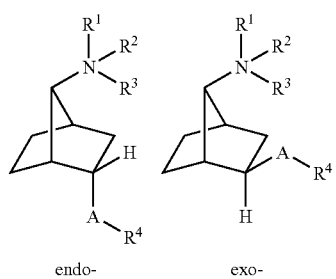

endo-    exo-

Currently it is preferred that the compounds of the invention be predominantly in the anti-endo configuration.

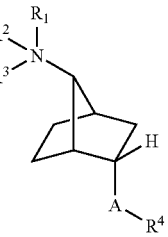

anti-, endo-

Compounds of the invention can also exist as optical isomers since substituted bicyclic ring systems can lack a plane of symmetry. The absolute configuration of the molecule can be defined using Cahn-Ingold-Prelog rules to assign the R or S designation to each position. To avoid confusion the ring numbering used below is employed.

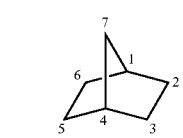

However, compounds of the invention include racemates, single enantiomers and mixtures of the enantiomers in any ratio, since all such forms have muscarinic M3 receptor modulating activity to varying extents.

A preferred class of compounds of the invention consists of quaternary ammonium salts of formula (I) wherein the nitrogen shown in formula (I) is quaternary nitrogen, carrying a positive charge.

Compounds of the invention may be useful in the treatment or prevention of diseases in which activation of muscarinic receptors are implicated, for example the present compounds are useful for treating a variety of indications, including but not limited to respiratory-tract disorders such as chronic obstructive lung disease, chronic bronchitis of all types (including dyspnoea associated therewith), asthma (allergic and non-allergic; 'wheezy-infant syndrome'), adult/acute respiratory distress syndrome (ARDS), chronic respiratory obstruction, bronchial hyperactivity, pulmonary fibrosis, pulmonary emphysema, and allergic rhinitis, exacerbation of airway hyperreactivity consequent to other drug therapy, particularly other inhaled drug therapy, pneumoconiosis (for example aluminosis, anthracosis, asbestosis, chalicosis, ptilosis, siderosis, silicosis, tabacosis and byssinosis); gastrointestinal-tract disorders such as irritable bowel syndrome, spasmodic colitis, gastroduodenal ulcers, gastrointestinal convulsions or hyperanakinesia, diverticulitis, pain accompanying spasms of gastrointestinal smooth musculature; urinary-tract disorders accompanying micturition disorders including neurogenic pollakisuria, neurogenic bladder, nocturnal enuresis, psychosomatic bladder, incontinence associated with bladder spasms or chronic cystitis, urinary urgency or pollakiuria; motion sickness; and
cardiovascular disorders such as vagally induced sinus bradycardia.

For treatment of respiratory conditions, administration by inhalation will often be preferred, and in such cases administration of compounds (I) which are quaternary ammonium salts will often be preferred. In many cases, the duration of action of quaternary ammonium salts of the invention administered by inhalation is may be more than 12, or more than 24 hours for a typical dose. For treatment of gastrointestinal-tract disorders and cardiovascular disorders, administration by the parenteral route, usually the oral route, may be preferred.

Another aspect of the invention is a pharmaceutical composition comprising a compound of the invention and a pharmaceutically acceptable carrier or excipient.

Another aspect of the invention is the use of a compound of the invention for the manufacture of a medicament for the treatment or prevention of a disease or condition in which muscarinic M3 receptor activity is implicated.

Terminology

Unless otherwise qualified in the context in which they are used herein, the following terms have the following meanings:

"Acyl" means a —CO-alkyl group in which the alkyl group is as described herein. Exemplary acyl groups include —COCH$_3$ and —COCH(CH$_3$)$_2$.

"Acylamino" means a —NR-acyl group in which R and acyl are as described herein. Exemplary acylamino groups include —NHCOCH$_3$ and —N(CH$_3$)COCH$_3$.

"Alkoxy" and "alkyloxy" means an —O-alkyl group in which alkyl is as described below. Exemplary alkoxy groups include methoxy (—OCH$_3$) and ethoxy (—OC$_2$H$_5$).

"Alkoxycarbonyl" means a —COO-alkyl group in which alkyl is as defined below. Exemplary alkoxycarbonyl groups include methoxycarbonyl and ethoxycarbonyl.

"Alkyl" as a group or part of a group refers to a straight or branched chain saturated hydrocarbon group having from 1 to 12, preferably 1 to 6, carbon atoms, in the chain. Exemplary alkyl groups include methyl, ethyl, 1-propyl and 2-propyl.

"Alkenyl" as a group or part of a group refers to a straight or branched chain hydrocarbon group having from 2 to 12, preferably 2 to 6, carbon atoms and one carbon-carbon double bond in the chain. Exemplary alkenyl groups include ethenyl, 1-propenyl, and 2-propenyl.

"Alkynyl" as a group or part of a group refers to a straight or branched chain hydrocarbon group having from 2 to 12, preferably 2 to 6, carbon atoms and one carbon-carbon triple bond in the chain. Exemplary alkenyl groups include ethynyl, 1-propynyl, and 2-propynyl.

"Alkylamino" means a —NH-alkyl group in which alkyl is as defined above. Exemplary alkylamino groups include methylamino and ethylamino.

"Alkylene means an -alkyl-group in which alkyl is as defined previously. Exemplary alkylene groups include —CH$_2$—, —(CH$_2$)$_2$— and —C(CH$_3$)HCH$_2$—.

"Alkenylene" means an -alkenyl-group in which alkenyl is as defined previously. Exemplary alkenylene groups include —CH=CH—, —CH=CHCH$_2$—, and —CH$_2$CH=CH—.

"Alkynylene" means an -alkynyl-group in which alkynyl is as defined previously. Exemplary alkenylene groups include —CC—, —CCCH$_2$—, and —CH$_2$CC—.

"Alkylsulfinyl" means a —SO-alkyl group in which alkyl is as defined above. Exemplary alkylsulfinyl groups include methylsulfinyl and ethylsulfinyl.

"Alkylsulfonyl" means a —SO$_2$-alkyl group in which alkyl is as defined above. Exemplary alkylsulfonyl groups include methylsulfonyl and ethylsulfonyl.

"Alkylthio" means a —S-alkyl group in which alkyl is as defined above. Exemplary alkylthio groups include methylthio and ethylthio.

"Aminoacyl" means a —CO—NRR group in which R is as herein described. Exemplary aminoacyl groups include —CONH$_2$ and —CONHCH$_3$.

"Aminoalkyl" means an alkyl-NH$_2$ group in which alkyl is as previously described. Exemplary aminoalkyl groups include CH$_2$NH$_2$.

"Aminosulfonyl" means a —SO$_2$—NRR group in which R is as herein described. Exemplary aminosulfonyl groups include —SO$_2$NH$_2$ and —SO$_2$NHCH$_3$.

"Aryl" as a group or part of a group denotes an optionally substituted monocyclic or multicyclic aromatic carbocyclic moiety of from 6 to 14 carbon atoms, preferably from 6 to 10 carbon atoms, such as phenyl or naphthyl. The aryl group may be substituted by one or more substituent groups.

"Arylalkyl" means an aryl-alkyl-group in which the aryl and alkyl moieties are as previously described. Preferred arylalkyl groups contain a C$_{1-4}$ alkyl moiety. Exemplary arylalkyl groups include benzyl, phenethyl and naphthlenemethyl. The aryl part thereof may be substituted by one or more substituent groups.

"Arylalkyloxy" means an aryl-alkyloxy-group in which the aryl and alkyloxy moieties are as previously described. Preferred arylalkyloxy groups contain a C$_{1-4}$ alkyl moiety. Exemplary arylalkyl groups include benzyloxy. The aryl part thereof may be substituted by one or more substituent groups.

"Aryl-fused-cycloalkyl" means a monocyclic aryl ring, such as phenyl, fused to a cycloalkyl group, in which the aryl and cycloalkyl are as described herein. Exemplary aryl-fused-cycloalkyl groups include tetrahydronaphthyl and indanyl. The aryl and cycloalkyl rings may each be substituted by one or more substituent groups. The aryl-fused-cycloalkyl group may be attached to the remainder of the compound by any available carbon atom.

"Aryl-fused-heterocycloalkyl" means a monocyclic aryl ring, such as phenyl, fused to a heterocycloalkyl group, in which the aryl and heterocycloalkyl are as described herein.

Exemplary aryl-fused-heterocycloalkyl groups include tetrahydroquinolinyl, indolinyl, benzodioxinyl, benzodioxolyl, dihydrobenzofuranyl and isoindolonyl. The aryl and heterocycloalkyl rings may each be substituted by one or more substituent groups. The aryl-fused-heterocycloalkyl group may be attached to the remainder of the compound by any available carbon or nitrogen atom.

"Aryloxy" means an —O-aryl group in which aryl is described above. Exemplary aryloxy groups include phenoxy. The aryl part thereof may be substituted by one or more substituent groups.

"Cyclic amine" is a special case of "Heterocycloalkyl" or "heterocyclic" and means an optionally substituted 3 to 8 membered monocyclic cycloalkyl ring system where one of the ring carbon atoms is replaced by nitrogen, and which may optionally contain an additional heteroatom selected from O, S or NR (where R is as described herein). Exemplary cyclic amines include pyrrolidine, piperidine, morpholine, piperazine and N-methylpiperazine. The cyclic amine group may be substituted by one or more substituent groups.

"Cycloalkyl" means an optionally substituted saturated monocyclic or bicyclic ring system of from 3 to 12 carbon atoms, preferably from 3 to 8 carbon atoms, and more preferably from 3 to 6 carbon atoms. Exemplary monocyclic cycloalkyl rings include cyclopropyl, cyclopentyl, cyclohexyl and cycloheptyl. The cycloalkyl group may be substituted by one or more substituent groups.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl. The cycloalkyl part thereof may be substituted by one or more substituent groups.

"Dialkylamino" means a —N(alkyl)$_2$ group in which alkyl is as defined above. Exemplary dialkylamino groups include dimethylamino and diethylamino.

"Halo" or "halogen" means fluoro, chloro, bromo, or iodo. Preferred are fluoro or chloro.

"Haloalkoxy" means an —O-alkyl group in which the alkyl is substituted by one or more halogen atoms. Exemplary haloalkyl groups include trifluoromethoxy and difluoromethoxy.

"Haloalkyl" means an alkyl group which is substituted by one or more halo atoms. Exemplary haloalkyl groups include trifluoromethyl.

"Heteroaryl" as a group or part of a group denotes an optionally substituted aromatic monocyclic or multicyclic organic moiety of from 5 to 14 ring atoms, preferably from 5 to 10 ring atoms, in which one or more of the ring atoms is/are is element(s) other than carbon, for example nitrogen, oxygen or sulfur. Examples of such groups include benzimidazolyl, benzoxazolyl, benzothiazolyl, benzofuranyl, benzothienyl, furyl, imidazolyl, indolyl, indolizinyl, isoxazolyl, isoquinolinyl, isothiazolyl, oxazolyl, oxadiazolyl, pyrazinyl, pyridazinyl, pyrazolyl, pyridyl, pyrimidinyl, pyrrolyl, quinazolinyl, quinolinyl, tetrazolyl, 1,3,4-thiadiazolyl, thiazolyl, thienyl and triazolyl groups. The heteroaryl group may be may be substituted by one or more substituent groups. The heteroaryl group may be attached to the remainder of the compound of the invention by any available carbon or nitrogen atom.

"Heteroarylalkyl" means a heteroaryl-alkyl-group in which the heteroaryl and alkyl moieties are as previously described. Preferred heteroarylalkyl groups contain a lower alkyl moiety. Exemplary heteroarylalkyl groups include pyridylmethyl. The heteroaryl part thereof may be substituted by one or more substituent groups.

"Heteroarylalkyloxy" means a heteroaryl-alkyloxy-group in which the heteroaryl and alkyloxy moieties are as previously described. Preferred heteroarylalkyloxy groups contain a lower alkyl moiety. Exemplary heteroarylalkyloxy groups include pyridylmethyloxy. The heteroaryl part thereof may be substituted by one or more substituent groups.

"Heteroaryloxy" means a heteroaryloxy-group in which the heteroaryl is as previously described. Exemplary heteroaryloxy groups include pyridyloxy. The heteroaryl part thereof may be substituted by one or more substituent groups.

"Heteroaryl-fused-cycloalkyl" means a monocyclic heteroaryl group, such as pyridyl or furanyl, fused to a cycloalkyl group, in which heteroaryl and cycloalkyl are as previously described. Exemplary heteroaryl-fused-cycloalkyl groups include tetrahydroquinolinyl and tetrahydrobenzofuranyl. The heteroaryl and cycloalkyl rings may each be substituted by one or more substituent groups. The heteroaryl-fused-cycloalkyl group may be attached to the remainder of the compound by any available carbon or nitrogen atom.

"Heteroaryl-fused-heterocycloalkyl" means a monocyclic heteroaryl group, such as pyridyl or furanyl, fused to a heterocycloalkyl group, in which heteroaryl and heterocycloalkyl are as previously described. Exemplary heteroaryl-fused-heterocycloalkyl groups include dihydrodioxinopyridinyl, dihydropyrrolopyridinyl, dihydrofuranopyridinyl and dioxolopyridinyl. The heteroaryl and heterocycloalkyl rings may each be substituted by one or more substituents groups. The heteroaryl-fused-heterocycloalkyl group may be attached to the remainder of the compound by any available carbon or nitrogen atom.

"Heterocycloalkyl" or "heterocyclic" means: (i) an optionally substituted cycloalkyl group of from 4 to 8 ring members which contains one or more heteroatoms selected from O, S or NR; (ii) a cycloalkyl group of from 4 to 8 ring members which contains CONR and CONRCO (examples of such groups include succinimidyl and 2-oxopyrrolidinyl). The heterocycloalkyl group may be substituted by one or more substituents groups. The heterocycloalkyl group may be attached to the remainder of the compound by any available carbon or nitrogen atom.

"Heterocycloalkylalkyl" or "heterocyclicalkyl" means a heterocycloalkyl-alkyl-group in which the heterocycloalkyl and alkyl moieties are as previously described.

"Lower alkyl" as a group means unless otherwise specified, an aliphatic hydrocarbon group which may be straight or branched having 1 to 4 carbon atoms in the chain, i.e, methyl, ethyl, propyl (propyl or iso-propyl) or butyl (butyl, iso-butyl or tert-butyl).

"Sulfonyl" means a —SO$_2$-alkyl group in which alkyl is as described herein. Exemplary sulfonyl groups include methanesulfonyl.

"Sulfonylamino" means a —NR-sulfonyl group in which R and sulfonyl are as described herein. Exemplary sulfonylamino groups include —NHSO$_2$CH$_3$. R means alkyl, aryl, or heteroaryl as described herein.

"Pharmaceutically acceptable salt" means a physiologically or toxicologically tolerable salt and includes, when appropriate, pharmaceutically acceptable base addition salts, pharmaceutically acceptable acid addition salts, and pharmaceutically acceptable quaternary ammonium salts. For example (i) where a compound of the invention contains one or more acidic groups, for example carboxy groups, pharmaceutically acceptable base addition salts that may be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that may be formed include hydrochlorides, hydrobromides, sulfates, phosphates, acetates, citrates, lactates, tartrates, mesylates, maleates, fumarates, succinates and the like; (iii) where a compound contains a quaternary ammonium group acceptable counter-ions may be, for example, chlorides, bromides, sulfates, methanesulfonates, benzenesulfonates, toluenesulfonates (tosylates), phosphates, acetates, citrates, lactates, tartrates, mesylates, maleates, fumarates, succinates and the like.

It will be understood that, as used herein, references to the compounds of the invention are meant to also include the pharmaceutically acceptable salts.

"Prodrug" refers to a compound which is convertible in vivo by metabolic means (e.g. by hydrolysis, reduction or oxidation) to a compound of the invention. For example an ester prodrug of a compound of the invention containing a hydroxy group may be convertible by hydrolysis in vivo to the parent molecule. Suitable esters of compounds of the invention containing a hydroxy group, are for example acetates, citrates, lactates, tartrates, malonates, oxalates, salicylates, propionates, succinates, fumarates, maleates, methylene-bis-β-hydroxynaphthoates, gentisates, isothionates, di-p-toluoyltartrates, methanesulfonates, ethanesulfonates, benzenesulfonates, p-toluenesulfonates, cyclohexylsulfamates and quinates. As another example an ester prodrug of a compound of the invention containing a carboxy group may be convertible by hydrolysis in vivo to the parent molecule. Examples of ester prodrugs are those described by F. J. Leinweber, Drug Metab. Res., 1987, 18, 379.

It will be understood that, as used in herein, references to the compounds of the invention are meant to also include the prodrug forms.

"Saturated" pertains to compounds and/or groups which do not have any carbon-carbon double bonds or carbon-carbon triple bonds.

"Optionally substituted" means optionally substituted with up to four substituents. Optional substituent groups include acyl (e.g. —COCH$_3$), alkoxy (e.g., —OCH$_3$), alkoxycarbonyl (e.g. —COOCH$_3$), alkylamino (e.g. —NHCH$_3$), alkylsulfinyl (e.g. —SOCH$_3$), alkylsulfonyl (e.g. —SO$_2$CH$_3$), alkylthio (e.g. —SCH$_3$), —NH$_2$, aminoacyl (e.g. —CON(CH$_3$)$_2$), aminoalkyl (e.g. —CH$_2$NH$_2$), arylalkyl (e.g. —CH$_2$Ph or —CH$_2$—CH$_2$-Ph), cyano, dialkylamino (e.g. —N(CH$_3$)$_2$), halo, haloalkoxy (e.g. —OCF$_3$ or —OCHF$_2$), haloalkyl (e.g. —CF), alkyl (e.g. —CH$_3$ or —CH$_2$CH$_3$), —OH, —NO$_2$, aryl (optionally substituted with alkoxy, haloalkoxy, halogen, alkyl or haloalkyl), heteroaryl (optionally substituted with alkoxy, haloalkoxy, halogen, alkyl or haloalkyl), heterocycloalkyl, aminoacyl (e.g. —CONH$_2$, —CONHCH$_3$), aminosulfonyl (e.g. —SO$_2$NH$_2$, —SO$_2$NHCH$_3$), acylamino (e.g. —NHCOCH$_3$), sulfonylamino (e.g. —NHSO$_2$CH$_3$), heteroarylalkyl, cyclic amine (e.g. morpholine), aryloxy, heteroaryloxy, arylalkyloxy (e.g. benzyloxy) and heteroarylalkyloxy.

Alkylene, alkenylene or alkynylene radicals may be optionally substituted. Optional substituent groups in the foregoing radicals include alkoxy (e.g., —OCH$_3$), alkylamino (e.g. —NHCH$_3$), alkylsulfinyl (e.g. —SOCH$_3$), alkylsulfonyl (e.g. —SO$_2$CH$_3$), alkylthio (e.g. —SCH$_3$), —NH$_2$, aminoalkyl (e.g. —CH$_2$NH$_2$), arylalkyl (e.g. —CH$_2$Ph or —CH$_2$—CH$_2$-Ph), cyano, dialkylamino (e.g. —N(CH$_3$)$_2$), halo, haloalkoxy (e.g. —OCF$_3$ or —OCHF$_2$), haloalkyl (e.g. —CF$_3$), alkyl (e.g. —CH$_3$ or —CH$_2$CH$_3$), —OH, and —NO$_2$.

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

The Groups $R^1$, $R^2$ and $R^3$

There are three combinations of groups $R^1$, $R^2$ and $R^3$

In combination (i) $R^1$ is $C_1$-$C_6$-alkyl or a hydrogen atom; and $R^2$ is a hydrogen atom or a group —$R^5$, or a group, —Z—Y—$R^5$, or a group —Z—$NR^9R^{10}$; or a group —Z—CO—$NR^9R^{10}$; or a group —Z—$NR^9$—CO—$R^5$; or a group —Z—$CO_2$—$R^5$; or a group —Z—$CO_2$H; and $R^3$ is a lone pair, or $C_1$-$C_6$-alkyl in which case the nitrogen atom to which it is attached is a quaternary nitrogen and carries a positive charge;

In combination (ii) $R^1$ and $R^3$ together with the nitrogen to which they are attached form a heterocycloalkyl ring, and $R^2$ is a hydrogen atom; or a group —$R^5$, or a group, —Z—Y—$R^5$, or a group —Z—$NR^9R^{10}$, or a group —Z—CO—$NR^9R^{10}$, or a group —Z—$NR^9$—CO—$R^5$, or a group —Z—$CO_2$—$R^5$, or a group —Z—$CO_2$H, in which cases the nitrogen atom to which it is attached is a quaternary nitrogen and carries a positive charge. In particular $R^1$ and $R^3$ together with the nitrogen to which they are attached may form a monocyclic ring of from 3 to 7 ring atoms, in which the hetero-atoms are nitrogen.

Examples of such rings include azetidinyl, piperidinyl, piperazinyl, N-substituted piperazinyl such as methylpiperazinyl, and pyrrolidinyl rings.

In combination (iii) $R^1$ and $R^2$ together with the nitrogen to which they are attached form a heterocycloalkyl ring, said ring being substituted by a group —Y—$R^5$, or a group —Z—Y—$R^5$, or a group —Z—$NR^9R^{10}$; or a group —Z—CO—$NR^9R^{10}$; or a group —Z—$NR^9$—CO—$R^5$; or a group —Z—$CO_2$—$R^5$; or a group —Z—$CO_2$H and $R^3$ is a lone pair, or $C_1$-$C_6$-alkyl in which case the nitrogen atom to which it is attached is a quaternary nitrogen and carries a positive charge. In particular $R^1$ and $R^2$ together with the nitrogen to which they are attached may form a monocyclic ring of from 3 to 7 ring atoms, in which the hetero-atoms are nitrogen. Examples of such rings include azetidinyl, piperidinyl, piperazinyl, N-substituted piperazinyl such as methylpiperazinyl, and pyrrolidinyl rings.

Where a group —$R^5$, or a group —Z—Y—$R^5$, or a group —Z—$NR^9R^{10}$; or a group —Z—CO—$NR^9R^{10}$; or a group —Z—$NR^9$—CO—$R^5$; or a group —Z—$CO_2$—$R^5$; or a group —Z—$CO_2$H; is present in $R^2$, or the ring formed by $R^1$, $R^2$ and the nitrogen to which they are attached:

Z may be, for example —(CH$_2$)$_{1-16}$— the latter being optionally substituted on up to three carbons in the chain by methyl;

Y is a bond or —O—;

$R^5$ may be $C_1$-$C_6$-alkyl, such as methyl, ethyl, n- or isopropyl, n-, sec- or tertbutyl;

Optionally substituted aryl such as phenyl or naphthyl, or aryl-fused-heterocycloalkyl such as 3,4-methylenedioxyphenyl, 3,4-ethylenedioxyphenyl, or dihydrobenzofuranyl;

Optionally substituted heteroaryl such as pyridyl, pyrrolyl, pyrimidinyl, oxazolyl, isoxazolyl, benzisoxazolyl, benzoxazolyl, thiazolyl, benzothiazolyl, quinolyl, thienyl, benzothienyl, furyl, benzofuryl, imidazolyl, benzimidazolyl, isothiazolyl, benzisothiazolyl, pyrazolyl, isothiazolyl, triazolyl, benzotriazolyl, thiadiazolyl, oxadiazolyl, pyridazinyl, pyridazinyl, triazinyl, indolyl and indazolyl;

Optionally substituted aryl($C_1$-$C_6$-alkyl)- such as those wherein the aryl part is any of the foregoing specifically mentioned aryl groups and the —($C_1$-$C_6$-alkyl)- part is —$CH_2$— or —$CH_2CH_2$—;

Optionally substituted aryl-fused-cycloalkyl such as indanyl or 1,2,3,4-tetrahydronaphthalenyl;

Optionally substituted heteroaryl($C_1$-$C_8$-alkyl)- such as those wherein the heteroaryl part is any of the foregoing specifically mentioned heteroaryl groups and the —($C_1$-$C_6$-alkyl)- part is —$CH_2$— or —$CH_2CH_2$—;

Optionally substituted cycloalkyl such as cyclopropyl, cyclobutyl, cyclopentyl or cyclohexyl; or Optionally substituted heterocycloalkyl($C_1$-$C_8$-alkyl)-, such as those wherein the heterocycloalkyl part is azetidinyl, piperidinyl, piperazinyl, N-substituted piperazinyl such as methylpiperazinyl, or pyrrolidinyl and the —($C_1$-$C_6$-alkyl)- part is —$CH_2$— or —$CH_2CH_2$—;

$R^9$ and $R^{10}$ may be independently selected from hydrogen; $C_1$-$C_6$-alkyl such as methyl, ethyl or n- or isopropyl; or any of those optionally substituted aryl, aryl-fused-heterocycloalkyl, aryl-fused-cycloalkyl, heteroaryl or aryl ($C_1$-$C_8$-alkyl)-groups specifically mentioned in the discussion of $R^5$ above; or $R^9$ and $R^{10}$ together with the nitrogen atom to which they are attached may form a heterocyclic ring of 4-8 ring atoms, preferably 4-6 ring atoms optionally containing a further nitrogen or oxygen atom, such as azetidinyl, piperidinyl, piperazinyl, N-substituted piperazinyl such as methylpiperazinyl, pyrrolidinyl, morpholinyl, and thiomorpholinyl.

Currently preferred are compounds of the invention wherein, in the group —$NR^1R^2R^3$, $R^1$ is methyl or ethyl, $R^2$ is a group —Z—Y—$R^5$ as discussed above, especially wherein $R^5$ is a cyclic lipophilic group such as phenyl, benzyl or phenylethyl, Y is a bond or —O—, and —Z— is a straight or branched alkylene radical linking the nitrogen and —Y$R^5$ by a chain of up to 12, for example up to 9, carbon atoms, and $R^3$ is methyl, so that the nitrogen is quaternised and carries a positive charge.

The Radical A

A is an oxygen atom or group —$N(R^{12})$—, wherein $R^{12}$ is $C_1$-$C_6$-alkyl (such as methyl or ethyl) or $R^{12}$ is a hydrogen atom. Currently preferred is the case where A is —O—.

The Group $R^4$ $R^4$ is selected from one of the groups of formula (a), (b), (c) or (d);

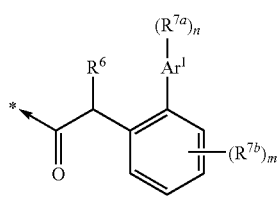

(a)

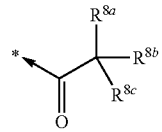

(b)

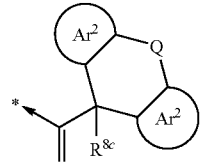

(c)

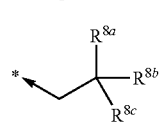

(d)

In the group (a), $R^6$ may be $C_1$-$C_6$-alkyl such as methyl or ethyl or a hydrogen atom; $Ar^1$ may be an aryl group such as phenyl, a heteroaryl group such as thienyl, especially 2-thienyl, or a cycloalkyl group such as cyclohexyl, cyclopentyl, cyclopropyl, or cyclobutyl; ring substituents $R^{7a}$ and $R^{7b}$ may be independently a $C_1$-$C_6$-alkyl group, such as methyl, ethyl, n- or isopropyl, n-, sec- or tertbutyl, or halogen such as fluoro, chloro or bromo; and m and n may be independently 0, 1, 2 or 3.

In the groups (b) and (d), $R^{8a}$ and $R^{8b}$ may be independently selected from any of those aryl, aryl-fused-heterocycloalkyl, aryl-fused-cycloalkyl, heteroaryl, $C_1$-$C_6$-alkyl, or cycloalkyl groups specifically mentioned in the discussion of $R^5$ above. $R^{8c}$ may be —OH, a hydrogen atom, $C_1$-$C_6$-alkyl such as methyl or ethyl, hydroxy-$C_1$-$C_6$-alkyl such as hydroxymethyl, nitrile, or a group $CONR^{8d}_2$ wherein each $R^{8d}$ is independently $C_1$-$C_6$-alkyl such as methyl or ethyl, or a hydrogen atom. Presently preferred is the case where $R^{8c}$ is —OH. Preferred combinations of $R^{8a}$ and $R^{8b}$, especially when $R^{8c}$ is —OH, include those wherein (i) each of $R^{8a}$ and $R^{8b}$ is optionally substituted monocyclic heteroaryl of 5 or 6 ring atoms such as pyridyl, oxazolyl, thiazolyl, furyl and especially thienyl such a 2-thienyl; (ii) optionally substituted phenyl; (iii) one of $R^{8a}$ and $R^{8b}$ is optionally substituted phenyl and the other is cycloalkyl such as cyclopropyl, cyclobutyl, or especially cyclopentyl or cyclohexyl; and (iv) one of $R^{8a}$ and $R^{8b}$ is optionally substituted monocyclic heteroaryl of 5 or 6 ring atoms such as pyridyl, thienyl, oxazolyl, thiazolyl, or furyl; and the other is cycloalkyl such as cyclopropyl, cyclobutyl, cyclopentyl or cyclohexyl.

In the group (c), $R^{8c}$ may be —OH, a hydrogen atom, $C_1$-$C_6$-alkyl such as methyl or ethyl, hydroxy-$C_1$-$C_6$-alkyl such as hydroxymethyl, nitrile, or a group $CONR^{8d}_2$ wherein each $R^{8d}$ is independently $C_1$-$C_6$-alkyl such as methyl or ethyl, or a hydrogen atom. Presently preferred is the case where $R^{8c}$ is —OH. Each $Ar^2$ is an aryl, heteroaryl or cycloalkyl ring and may be, for example, any of those aryl, heteroaryl, $C_1$-$C_6$-alkyl, or cycloalkyl rings specifically mentioned in the discussion of $R^5$ above. Preferred $Ar^2$ rings include phenyl. The bridge -Q- between the two $Ar^2$ rings is —O—, —$CH_2$— or —$CH_2CH_2$—.

Of the $R^4$ options (a), (b), (c) and (d), it is presently preferred that $R^4$ be a group (b) or (c).

A preferred subclass of compounds with which the invention is concerned consists of those of formula (IA)

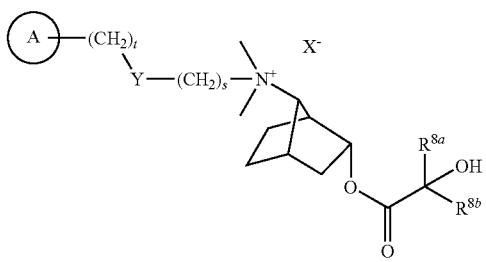

(IA)

wherein ring A is an optionally substituted phenyl ring, or a monocyclic heterocyclic ring of 5 or 6 ring atoms, or a phenyl-fused-heterocycloalkyl ring system wherein the heterocycloalkyl ring is a monocyclic heterocyclic ring of 5 or 6 ring atoms; $R^{8a}$ is phenyl, thienyl, cyclopentyl or cyclohexyl; $R^{8b}$ is phenyl; thienyl, cyclopentyl or cyclohexyl; s is 1, 2, 3, 4, 5, 6 or 7 and t is 0, 1, 2, 3, 4, 5, 6 or 7 provided that s+t is not greater than 10; Y is a bond or —O—, and $X^-$ is a pharmaceutically acceptable anion. In compounds (IA), it is currently preferred that ring A is (i) optionally substituted phenyl, wherein optional substituents are selected from alkoxy, halo especially fluoro or chloro, $C_1$-$C_3$-alkyl, amino $C_1$-$C_3$-acyl, amino $C_1$-$C_3$-alkyl, and aminosulfonyl, or (ii) a phenyl-fused-heterocycloalkyl ring system wherein the heterocycloalkyl ring is a monocyclic heterocyclic ring of 5 or 6 ring atoms, such as dihydrobenzofuranyl.

Another preferred subclass of compounds with which the invention is concerned consists of those of formula (IB)

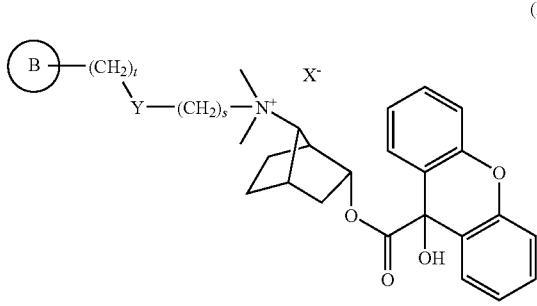

(IB)

wherein ring B is an optionally substituted phenyl ring or a monocyclic heterocyclic ring of 5 or 6 ring atoms or an aryl-fused heterocycloalkyl ring; s is 1, 2, 3, 4, 5, 6 or 7 and t is 0, 1, 2, 3, 4, 5, 6 or 7 provided that s+t is not greater than 10; Y is a bond or —O—; and $X^-$ is a pharmaceutically acceptable anion. In compounds (IB), it is currently preferred that ring B is (i) optionally substituted phenyl, wherein optional substituents are selected from alkoxy, halo especially fluoro or chloro, $C_1$-$C_3$-alkyl, amino $C_1$-$C_3$-acyl, amino $C_1$-$C_3$-alkyl, and aminosulfonyl, or (ii) phenyl-fused-heterocycloalkyl wherein the heterocycloalkyl ring is a monocyclic heterocyclic ring of 5 or 6 ring atoms, such as dihydrobenzofuranyl.

In both subclasses (IA) and (IB), s+t may be, for example 1, 2, 3, 4, 5, 6, or 7 and may arise from suitable combinations of t and s such as where t is 0, 1, 2, 3, 4, 5 or 6 and s is 1, 2, 3, 4, 5, 6 or 7. In compounds (IA) and (IB), a currently preferred combination of t, Y and s is where t is 0, s is 3, and Y is —O—. A further currently preferred combination is where Y is a bond and s+t is 2, 3 or 4.

In both subclasses (IA) and (IB), as in the compounds of the invention generally, compounds predominantly in the anti-endo configuration are preferred.

Examples of compounds of the invention include those of the Examples herein. Preferred compounds of the invention include:

anti-2-(Biphenyl-2-ylcarbamoyloxy)bicyclo[2.2.1]hept-7-yl]-dimethyl-(3-phenoxy-propyl)-ammonium salts anti-[(1S,2R)-2-(2-Hydroxy-2,2-di-thiophen-2-yl-acetoxy)-bicyclo[2.2.1]hept-7-yl]-dimethyl-(3-phenyl-propyl)-ammonium salts anti-(±)-2-(2-Hydroxy-2,2-di-thiophen-2-yl-acetoxy)-bicyclo[2.2.1]hept-7-yl]-dimethyl-(3-phenyl-propyl)-ammonium salts anti-(1S,2R)-2-(2-Hydroxy-2,2-di-thiophen-2-yl-acetoxy)-bicyclo[2.2.1]hept-7-yl]-dimethyl-(3-phenoxy-propyl)-ammonium salts anti-[(1S,2R)-2-(2-Hydroxy-2,2-di-thiophen-2-yl-acetoxy)-bicyclo[2.2.1]hept-7-yl]-dimethyl-phenethyl-ammonium salts anti-[(1S,2R)-2-(2-Hydroxy-2,2-di-thiophen-2-yl-acetoxy)-bicyclo[2.2.1]hept-7-yl]-dimethyl-(4-phenyl-butyl)-ammonium salts anti-[(1S,2R)-2-(2-Hydroxy-2,2-di-thiophen-2-yl-acetoxy)-bicyclo[2.2.1]hept-7-yl]-trimethyl-ammonium salts (2-Benzyloxy-ethyl)-anti-[(1S,2R)-2-(2-hydroxy-2,2-di-thiophen-2-yl-acetoxy)-bicyclo[2.2.1]hept-7-yl]-dimethyl-ammonium salts anti-(1S,2R) 2-(2-Hydroxy-2,2-diphenyl-acetoxy)-bicyclo[2.2.1]hept-7-yl]-dimethyl-(3-phenoxy-propyl)-ammonium salts anti-(1S,2R) Dimethyl-(3-phenoxy-propyl)-[2-(9H-xanthene-9-carbonyloxy)-bicyclo[2.2.1]hept-7-yl]-ammonium salts anti-(1S,2R) 2-(9-Hydroxy-9H-xanthene-9-carbonyloxy)-bicyclo[2.2.1]hept-7-yl]-dimethyl-(3-phenoxy-propyl)-ammonium salts anti-[(1S,2R)-2-(2-Hydroxy-2,2-di-thiophen-2-yl-acetoxy)-bicyclo[2.2.1]hept-7-yl]-indan-2-yl-dimethyl-ammonium salts (Benzylcarbamoyl-methyl)-anti-[(1S,2R)-2-(2-hydroxy-2,2-di-thiophen-2-yl-acetoxy)-bicyclo[2.2.1]hept-7-yl]-dimethyl-ammonium salts

[2-(2,3-Dihydro-benzofuran-5-yl)-ethyl]-anti-[(1S,2R)-2-(2-hydroxy-2,2-di-thiophen-2-yl-acetoxy)-bicyclo[2.2.1]hept-7-yl]-dimethyl-ammonium salts As referred to in the Background to the Invention section above, compounds with dual M3 receptor antagonist and β2-adrenoreceptor agonist activity are known, and treatment of respiratory disease with such dual activity compounds is a recognised form of treatment. The known strategy for the provision of compounds with such dual activity mechanisms is simple covalent linkage of a compound with M3 receptor antagonist activity to a compound with a β2-adrenoreceptor agonist activity. Such covalent conjugates of an M3 receptor agonist compound (I) as defined and discussed above and a β2-adrenoreceptor agonist also form part of the invention. For example, such dual activity conjugates include compounds of formula (I), as defined and discussed above, modified by replacement of the $R^2$ group by a -L-B group wherein L is a linker radical and B is a moiety having β2 adrenoreceptor agonist activity. Structurally, such dual activity conjugates may be represented as in formula (III):

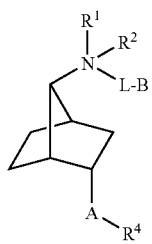

(III)

wherein $R^1$, $R^2$ and $R^4$ are as defined and discussed above in relation to compounds (I) of the invention, L is a divalent linker radical and B is a moiety having (β2-adrenoreceptor agonist activity, such as the β2-agonist pharmacophore referred to above in the Background to the Invention section. Such compounds (III) form another aspect of the present invention. An example of such a compound is that of Example No. 41 herein.

The present invention is also concerned with pharmaceutical formulations comprising, as an active ingredient, a compound of the invention. Other compounds may be combined with compounds of this invention for the prevention and treatment of inflammatory diseases of the lung. Thus the present invention is also concerned with pharmaceutical compositions for preventing and treating respiratory-tract disorders such as chronic obstructive lung disease, chronic bronchitis, asthma, chronic respiratory obstruction, pulmonary fibrosis, pulmonary emphysema, and allergic rhinitis comprising a therapeutically effective amount of a compound of the invention and one or more other therapeutic agents.

Other compounds may be combined with compounds of this invention for the prevention and treatment of inflammatory diseases of the lung. Accordingly the invention includes a combination of an agent of the invention as hereinbefore described with one or more anti-inflammatory, bronchodilator, antihistamine, decongestant or anti-tussive agents, said agents of the invention hereinbefore described and said combination agents existing in the same or different pharmaceutical compositions, administered separately or simultaneously. Preferred combinations would have two or three different pharmaceutical compositions. Suitable therapeutic agents for a combination therapy with compounds of the invention include:

One or more other bronchodilators such as PDE3 inhibitors;
Methyl xanthines such as theophylline;
Other muscarinic receptor antagonists;
A corticosteroid, for example fluticasone propionate, ciclesonide, mometasone furoate or budesonide, or steroids described in WO02/88167, WO02/12266, WO02/100879, WO02/00679, WO03/35668, WO03/48181, WO03/62259, WO03/64445, WO03/72592, WO04/39827 and WO04/66920;
A non-steroidal glucocorticoid receptor agonist;
A β2-adrenoreceptor agonist, for example albuterol (salbutamol), salmeterol, metaproterenol, terbutaline, fenoterol, procaterol, carmoterol, indacaterol, formoterol, arformoterol, picumeterol, GSK-159797, GSK-597901, GSK-159802, GSK-64244, GSK-678007, TA-2005 and also compounds of EP1440966, JP05025045, WO93/18007, WO99/64035, US2002/0055651, US2005/0133417, US2005/5159448, WO00/075114, WO01/42193, WO01/83462, WO02/66422, WO02/70490, WO02/76933, WO03/24439, WO03/42160, WO03/42164, WO03/72539, WO03/91204, WO03/99764, WO04/16578, WO04/016601, WO04/22547, WO04/32921, WO04/33412, WO04/37768, WO04/37773, WO04/37807, WO04/39762, WO04/39766, WO04/45618, WO04/46083, WO04/71388, WO04/80964, EP1460064, WO04/087142, WO04/89892, EP01477167, US2004/0242622, US2004/0229904, WO04/108675, WO04/108676, WO05/033121, WO05/040103, WO05/044787, WO04/071388, WO05/058299, WO05/058867, WO05/065650, WO05/066140, WO05/070908, WO05/092840, WO05/092841, WO05/092860, WO05/092887, WO05/092861, WO05/090288, WO05/092087, WO05/080324, WO05/080313, US20050182091, US20050171147, WO05/092870, WO05/077361, DE10258695, WO05/111002, WO05/111005, WO05/110990, US2005/0272769 WO05/110359, WO05/121065, US2006/0019991, WO06/016245, WO06/014704, WO06/031556, WO06/032627, US2006/0106075, US2006/0106213, WO06/051373, WO06/056471;
A leukotriene modulator, for example montelukast, zafirlukast or pranlukast;
protease inhibitors, such as inhibitors of matrix metalloprotease for example MMP12 and TACE inhibitors such as marimastat, DPC-333, GW-3333;
Human neutrophil elastase inhibitors, such as sivelestat and those described in WO04/043942, WO05/021509, WO05/021512, WO05/026123, WO05/026124, WO04/024700, WO04/024701, WO04/020410, WO04/020412, WO05/080372, WO05/082863, WO05/082864, WO03/053930;
Phosphodiesterase-4 (PDE4) inhibitors, for example roflumilast, arofylline, cilomilast, ONO-6126 or IC-485;
Phosphodiesterase-7 inhibitors;
An antitussive agent, such as codeine or dextramorphan;
Kinase inhibitors, particularly P38 MAPKinase inhibitors;
P2X7 anatgonists;
iNOS inhibitors;
A non-steroidal anti-inflammatory agent (NSAID), for example ibuprofen or ketoprofen;
A dopamine receptor antagonist;
TNF-α inhibitors, for example anti-TNF monoclonal antibodies, such as Remicade and CDP-870 and TNF receptor immunoglobulin molecules, such as Enbrel;
A2a agonists such as those described in EP1052264 and EP1241176;
A2b antagonists such as those described in WO2002/42298;
Modulators of chemokine receptor function, for example antagonists of CCR1, CCR2, CCR3, CXCR2, CXCR3, CX3CR1 and CCR8, such as SB-332235, SB-656933, SB-265610, SB-225002, MCP-1 (9-76), RS-504393, MLN-1202, INCB-3284;
Compounds which modulate the action of prostanoid receptors, for example a $PGD_2$ (DP1 or CRTH2), or a thromboxane $A_2$ antagonist eg ramatroban;
Compounds which modulate Th1 or Th2 function, for example, PPAR agonists;
Interleukin 1 receptor antagonists, such as Kineret;
Interleukin 10 agonists, such as Ilodecakin;
HMG-CoA reductase inhibitors (statins); for example rosuvastatin, mevastatin, lovastatin, simvastatin, pravastatin and fluvastatin;
Mucus regulators such as INS-37217, diquafosol, sibenadet, CS-003, talnetant, DNK-333, MSI-1956, gefitinib;
Antiinfective agents (antibiotic or antiviral), and antiallergic drugs including, but, not limited to, anti-histamines.

The weight ratio of the first and second active ingredients may be varied and will depend upon the effective dose of each ingredient. Generally, an effective dose of each will be used.

Any suitable route of administration may be employed for providing a mammal, especially a human, with an effective dosage of a compound of the present invention. In therapeutic use, the active compound may be administered by any convenient, suitable or effective route. Suitable routes of administration are known to those skilled in the art, and include oral, intravenous, rectal, parenteral, topical, ocular, nasal, buccal and pulmonary.

The magnitude of prophylactic or therapeutic dose of a compound of the invention will, of course, vary depending upon a range of factors, including the activity of the specific compound that is used, the age, body weight, diet, general health and sex of the patient, time of administration, the route of administration, the rate of excretion, the use of any other drugs, and the severity of the disease undergoing treatment. In general, the daily dose range for inhalation will lie within the range of from about 0.1 μg to about 10 mg per kg body weight of a human, preferably 0.1 μg to about 0.5 mg per kg, and more preferably 0.1 μg to 50 μg per kg, in single or divided doses. On the other hand, it may be necessary to use dosages outside these limits in some cases. Compositions suitable for administration by inhalation are known, and may include carriers and/or diluents that are known for use in such compositions. The composition may contain 0.01-99% by weight of active compound. Preferably, a unit dose comprises the active compound in an amount of 1 μg to 10 mg. For oral administration suitable doses are 10 μg per kg to 100 mg per kg, preferably 40 μg per kg to 4 mg per kg.

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the invention, additional active ingredient(s), and pharmaceutically acceptable excipients.

The pharmaceutical compositions of the present invention comprise a compound of the invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids, and salts of quaternary ammonium compounds with pharmaceutically acceptable counter-ions.

For delivery by inhalation, the active compound is preferably in the form of microparticles. They may be prepared by a variety of techniques, including spray-drying, freeze-drying and micronisation.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($C_2H_4F_2$) and isobutane.

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321). Additionally, compounds of the invention may be delivered in multi-chamber devices thus allowing for delivery of combination agents.

Methods of Synthesis

The compounds of the invention can be prepared according to the procedures of the following schemes and examples, using appropriate materials, and are further exemplified by the following specific examples. Moreover, by utilising the procedures described with the disclosure contained herein, one of ordinary skill in the art can readily prepare additional compounds of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 1999, may be used.

Compounds of the invention may be prepared according to the routes illustrated in Scheme 1.

Scheme 1
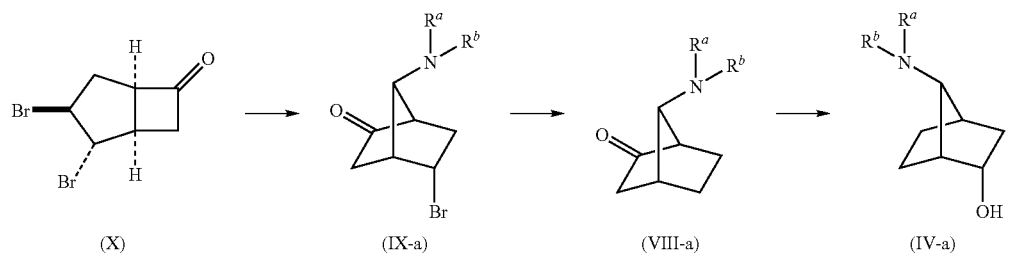
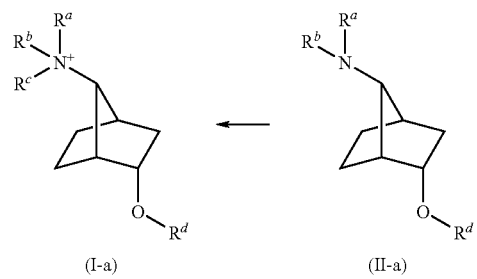
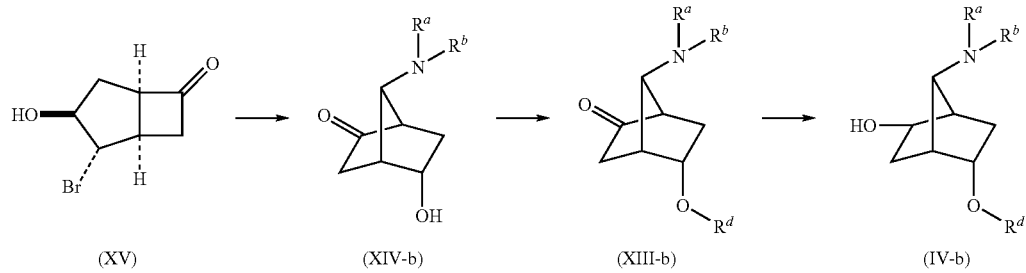
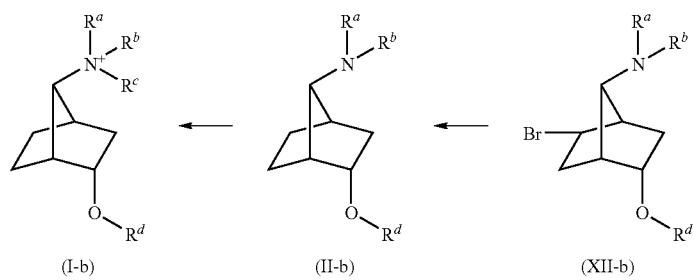

Compounds of formula (I-a) and (I-b) wherein $R^a$, $R^b$ and $R^c$ and $R^d$ are as defined for $R^1$, $R^2$, $R^3$ and $R^4$ in compounds of Formula (I) can be prepared from compounds of formula (II-a) or (II-b):

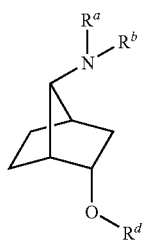
(II-a)

by reaction with a compound of formula (III-a):

$$R^c\text{—}X \quad \text{(III-a)}$$

wherein X is a leaving group such as halogen, tosylate, mesylate. The reaction can be performed in a range of solvents, such as acetonitrile, chloroform, DMF or DMSO, optionally in the presence of a tertiary amine base such as DIPEA, at a temperature from 0° C. to the reflux temperature of the solvent, preferably from ambient temperature to the reflux temperature of the solvent.

Compounds of formula (II-a) and (II-b) wherein $R^a$, $R^b$ and $R^d$ are as defined for $R^1$, $R^2$ and $R^4$ in compounds of formula (I) can be prepared from compounds of formula (II-a) or (II-b), where $R^b$=H, by reaction with a compound of formula (III-b):

$$R^b\text{—}CHO \quad \text{(III-b)}$$

In the presence of a suitable reducing agent such as a metal borohydride, especially sodium triacetoxyborohydride. The reaction can be performed in a range of solvents such as 1,2-dichloroethane, chloroform, dichloromethane, alcohols, optionally in the presence of an acid such as acetic acid, at a temperature from 0° C. to the reflux temperature of the solvent, preferably from 0° C. to ambient temperature of the solvent. Compounds of formula (III-a) and (III-b) are well known in the art and are readily available or can be prepared by known methods.

Suitable methods for the preparation of compounds of formula (II-a) or (II-b), where $R^b$=H include reaction of (II-a) or (II-b), where $R^b$=benzyl, with hydrogen in the presence of palladium on carbon or palladium hydroxide on carbon in suitable solvents such as methanol, ethanol, acetic acid, ethyl acetate and mixtures thereof. Alternatively, reaction of (II-a) or (II-b), where $R^b$=methyl or benzyl with 1-chloroethyl chloroformate in suitable solvent such as 1,2-dichloroethane at reflux temperature of the solvent then subsequent reaction with methanol is a preferred method for the preparation of compounds of formula (II-a) or (II-b), where $R^b$=H.

Compounds of formula (II-a) and (II-b) exist in two enantiomeric forms which can be separated by chiral preparative HPLC using conditions know to those skilled in the art and exemplified below. Alternatively, as the absolute configuration of compounds (II-a) and (II-b) are dictated by the absolute configuration of compounds (X) and (XV) respectively, and compounds (X) and (XV) are known in the literature (see EP0074856A2) one skilled in the art will recognise that use of homochiral starting material will deliver homochiral product of defined stereochemistry.

Compounds of formula (II-a) wherein $R^d$ is the group of formula (a), and $R^6$ is H as defined above for formula (I) may be prepared from compounds of formula (IV-a) wherein $R^a$ and $R^b$ are as defined above, by reaction with a compound of formula (V):

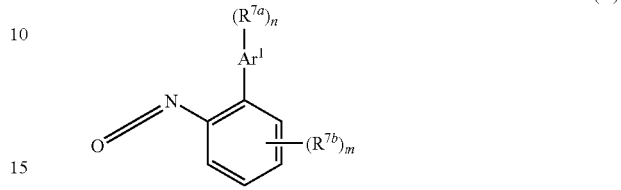
(V)

wherein $R^{7a}$, $R^{7b}$, n and m are as defined for formula (I). The reaction may take place in a range of non-nucleophilic organic solvents such as DMF or toluene at a range of temperatures, preferably between 0° C. and the reflux temperature of the solvent.

Compounds of formula (V) are well known in the art and are readily available or can be prepared by known methods.

Compounds of formula (II-a) in which $R^d$ is the group of formula (b) as defined above, may be prepared from compounds of formula (IV-a) by reaction with a compound of formula (VI):

(VI)

wherein $R^{8a}$, $R^{8b}$, and $R^{8c}$ are as defined for formula (I) and LG is a leaving group, for example, an O-alkyl, halogen or 1-imidazolyl group. The reaction is conducted in the presence of a strong base such as NaH in a solvent such as toluene, THF or dichloromethane at a range of temperatures, preferably between 0° C. and the reflux temperature of the solvent.

Compounds of formula (VI) wherein $R^{8a}$, $R^{8b}$, and $R^{8c}$ are as defined for formula (I) and LG is an O-alkyl, halogen or 1-imidazolyl group can be prepared from compounds of formula (VII) by known methods.

(VII)

Compounds of formula (VII) are well known in the art and are readily available or can be prepared by known methods such as those described in WO01/04118

Compounds of formula (II-a) in which $R^d$ is the group of formula (c) as defined above, may be prepared from compounds of formula (IV-a) by reaction with a compound of formula (VI-a):

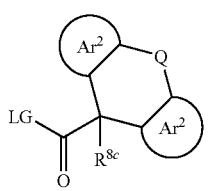
(VI-a)

wherein Ar² is as defined for formula (I) and LG is a leaving group, for example, an O-alkyl, halogen or 1-imidazolyl group. The reaction is conducted in the presence of a strong base such as NaH in a solvent such as toluene, THF or dichloromethane at a range of temperatures, preferably between 0° C. and the reflux temperature of the solvent.

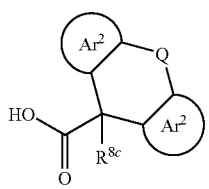
(VII-a)

Compounds of formula (VI-a) wherein $R^{8d}$ and $R^{8c}$ are as defined for formula (I) and LG is an O-alkyl, halogen or 1-imidazolyl group can be prepared from compounds of formula (VII-a) by known methods.

Compounds of formula (VII-a) are well known in the art and are readily available or can be prepared by known methods.

Compounds of formula (II-a) in which $R^d$ is the group of formula (d) as defined above, may be prepared from compounds of formula (IV-a) by reaction with a compound of formula (VI-b):

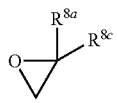
(VI-b)

The reaction is conducted in the presence of a strong base such as NaH in a solvent such as toluene, THF, preferably DMSO at a range of temperatures, preferably between 0° C. and the reflux temperature of the solvent.

Compounds of formula (VI-b) are well known in the art and are readily available or can be prepared by known methods.

Compounds of formula (IV-a) can be prepared from compounds of formula (VIII-a) by reaction with a suitable reducing agent, preferably a bulky reducing agent such as LiAlH(O$^t$Bu)$_3$. The reaction is carried out in a polar organic solvent preferably THF at a range of temperatures, preferably from −78° C. up to the reflux temperature of the solvent.

Compounds of formula (VIII-a) can be prepared from compounds of formula (IX-a) by reaction with a tin reagent, preferably Bu$_3$SnH and a radical initiator, preferably AIBN. The reaction can be performed in a range of solvents, preferably toluene, at a range of temperatures, preferably between ambient temperature and the reflux temperature of the solvent.

Compounds of formula (IX-a) can be prepared from compounds of formula (X) by reaction with an amine formula (XI):

$$R^aR^bNH \tag{XI}$$

The reaction is performed in a range of solvents, preferably THF/DCM at a range of temperatures, preferably between 0 and 100° C.

Compounds of formula (X) are known in the art: J. Chem. Soc. Perkin Trans I (1975) 1767-1773; Synthesis (1997), 155-166.

Compounds of formula (XI) are well known in the art and can be prepared by known methods, or are commercially available.

Compounds of formula (I-b) may be prepared from compounds of formula (II-b) by a method similar to the preparation of compounds of formula (I-a) from compounds of formula (II-a) above. Compounds of formula (II-b) may be prepared from compounds of formula (XII-b) by reaction with a tin reagent, preferably Bu$_3$SnH and a radical initiator, preferably AIBN. The reaction can be performed in a range of solvents, preferably toluene, at a range of temperatures, preferably between ambient temperature and the reflux temperature of the solvent.

Compounds of formula (XII-b) may be prepared from compounds of formula (IV-b) by is reaction with a brominating agent, preferably triphenylphosphine in carbon tetrabromide as solvent.

Compounds of formula (IV-b) can be prepared from compounds of formula (XIII-b) by reaction with a suitable reducing agent, preferably sodium borohydride. The reaction is carried out in a polar organic solvent preferably THF at a range of temperatures, preferably from −78° C. up to the reflux temperature of the solvent.

Compounds of formula (XIII-b) can be prepared from compounds of formula (XIV-b) by analogous methods to those used to prepare compounds of formula (II-a) from compounds of formula (IV-a).

Compounds of formula (XIV-b) can be prepared from compounds of formula (XV):

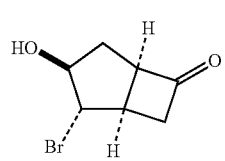
(XV)

by reaction with an amine of formula (XI). The reaction is performed in a range of solvents, preferably THF/DCM at a range of temperatures, preferably between 0 and 100° C.

Compounds of formula (XV) are described in GB2075503.

Scheme 2

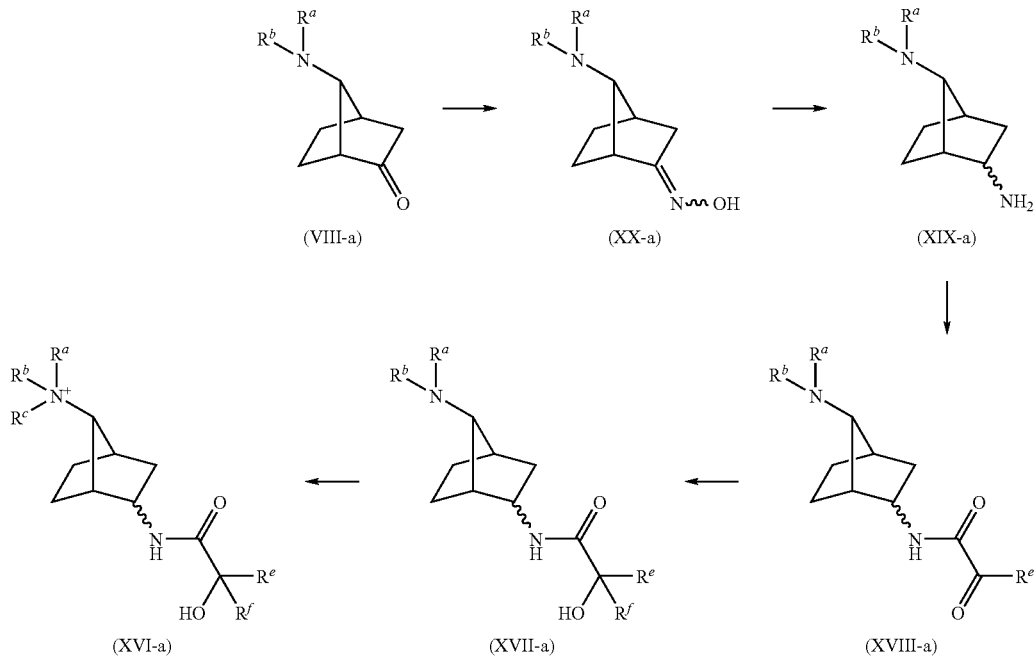

The preparation of compounds of Formula (I) in which A is a group —NR—, is outlined in Scheme 2.

Compounds of Formula (XVI-a) may be prepared from compounds of Formula (XVII-a) by similar methods as used to prepare compounds of Formula (I-a) from compounds of Formula (II-a).

Compounds of Formula (XVII-a) may be prepared from compounds of Formula (XVIII-a) by treatment with an organometallic reagent of Formula (XXI-a);

Where M is a metal species such as lithium or Mg-halide, especially a Grignard reagent in a suitable inert solvent such as THF or diethyl ether at a temperature between −78° and the reflux temperature of the solvent, preferably between 0° and ambient temperature. Compounds of Formula (XXI-a) are known in the art or may be prepared according to known methods.

Compounds of Formula (XVIII-a) may be prepared from compounds of Formula (XIX-a);

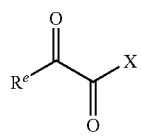

(XIX-a)

Where X is a leaving group, especially a halogen group, optionally in the presence of a suitable solvent such as dichloromethane, in the absence or presence of a base such as diisopropylethylamine. Compounds of formula (XIX-a) are commercially available or readily prepared according to the literature.

Compounds of Formula (XIX-a) may be prepared from compounds of Formula (VIII-a) by reduction of the oxime with a suitable reducing agent, such as a borohydride reagent, specifically $NaBH_4/NiCl_2$ in a suitable solvent such as methanol at a suitable temperature, such as 20° C.

Compounds of Formula (XX-a) may be prepared from compounds of Formula (VIII-a) by treatment with hydroxylamine or a salt thereof in the presence of a suitable solvent such as methanol, optionally in the presence of a base such as sodium acetate, at a temperature between 0° C. and the reflux temperature of the solvent, preferably at ambient temperature.

The following non-limiting Examples illustrate the invention.

General Experimental Details:

All reactions were carried out under an atmosphere of nitrogen unless specified otherwise.

Where products were purified by column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution. Where thin layer chromatography (TLC) has been used, it refers to silica gel TLC using plates, typically 3×6 cm silica gel on aluminium foil plates with a fluorescent indicator (254 nm), (e.g. Fluka 60778). All solvents and commercial reagents were used as received.

All compounds containing a basic centre(s), which were purified by HPLC, were obtained as the TFA salt unless otherwise stated.

Preparative HPLC Conditions:

HPLC System 1:

C18-reverse-phase column (100×22.5 mm i.d Genesis column with 7 μm particle size), eluting with a gradient of A: water+0.1% TFA; B: acetonitrile+0.1% TFA at a flow rate of 5 ml/min and gradient of 1%/min increasing in B. UV detection at 230 nm.

HPLC System 2:

Phenyl hexyl column (250×21.20 mm Luna column with 5 μm particle size), eluting with a gradient of A: water+0.1% TFA; B: acetonitrile+0.1% TFA at a flow rate of 5 ml/min with UV detection at 254 nm.

LC/MS Systems

The Liquid Chromatography Mass Spectroscopy (LC/MS) systems used:

LC-MS Method 1

Micromass Platform LCT with a C18-reverse-phase column (100×3.0 mm Higgins Clipeus with 5 μm particle size), elution with A: water+0.1% formic acid; B: acetonitrile+0.1% formic acid. Gradient:

| Gradient - Time | flow ml/min | % A | % B |
|---|---|---|---|
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection—MS, ELS, UV (100 μl split to MS with in-line UV detector)

MS ionisation method—Electrospray (positive ion)

LC-MS Method 2

Micromass Platform LCT with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow ml/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 μl split to MS with in-line UV detector)

MS ionisation method—Electrospray (positive and negative ion)

LC-MS Method 3

Waters Micromass ZQ with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow ml/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 μl split to MS with in-line UV detector)

MS ionisation method—Electrospray (positive and negative ion)

LC-MS Method 4

Waters Micromass ZQ with a C18-reverse-phase column (Higgins Clipeus 5 micron C18 100×3.0 mm or equivalent), elution with A: water+0.1% formic acid; B: acetonitrile+0.1% formic acid. Gradient:

| Gradient - Time | flow ml/min | % A | % B |
|---|---|---|---|
| 0.00 | 1.0 | 95 | 5 |
| 1.00 | 1.0 | 95 | 5 |
| 15.0 | 1.0 | 5 | 95 |
| 20.0 | 1.0 | 5 | 95 |
| 22.0 | 1.0 | 95 | 5 |
| 25.0 | 1.0 | 95 | 5 |

Detection—MS, ELS, UV (100 μl split to MS with in-line UV detector)

MS ionisation method—Electrospray (positive and negative ion)

Abbreviations Used in the Experimental Section:

DCM=dichloromethane; THF=tetrahydrofuran; MeOH=methanol; EtOH=ethanol; DMSO=dimethylsulfoxide; EtOAc=ethyl acetate; DIPEA=di-isopropylethylamine; EDCI=1-(3-dimethylaminopropyl)-3-ethylcarbodiimide hydrochloride; DMAP=dimethylaminopyridine; RT=ambient temperature; HATU=O-(7-Azabenzotriazol-1-yl)-N,N,N',N'-tetramethyluronium hexafluoro phosphate; TFA=trifluoroacetic acid; Rt=retention time; Satd=saturated

EXAMPLE 1

(±)-anti-Biphenyl-2-yl-carbamic acid 7-dimethylamino-bicyclo[2.2.1]hept-2-yl ester. (II-a): $R^a$, $R^b$=CH$_3$, $R^d$=biphenyl-2-ylcarbamyl

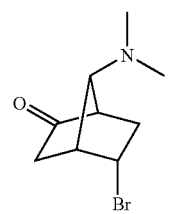

a. (±)-anti-5-Bromo-7-dimethylamino-bicyclo[2.2.1]hept-2-one. (IX-a): $R^a$, $R^b$=CH$_3$ To a chilled (−10° C.) DCM (20 mL) solution of (±)-2,3-dibromo-bicyclo[3.2.0]heptan-6-one was added a THF solution of dimethylamine (2 M, 8.23 mL, 16.5 mmol) dropwise. The reaction was allowed to slowly warm to ambient temperature over several hours. After 17 hours the reaction mixture was concentrated and the residue dissolved in Et$_2$O and filtered. The filtrate was absorbed onto diatomaceous earth and chromatographed on a column of silica gel eluting with 25% Et$_2$O in pentane to give 0.88 g (58%) of the title product as an orange solid. $^1$H NMR (CDCl$_3$, 400 MHz): δ 1.70 (1H, ddd, J=14.2 Hz, 4.4 Hz, 1.3 Hz), 2.18 (6H, s), 2.2 (1H, m), 2.47 (1H, d, J=1.2 Hz), 2.60 (1H, d, J=4.8 Hz), 2.80 (3H, m), 4.66 (1H, m).

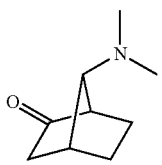

b. (±)-anti-7-Dimethylamino-bicyclo[2.2.1]heptan-2-one. (VIII-a): $R^a$, $R^b$=CH$_3$ Toluene was degassed prior to the reaction by vigorously bubbling nitrogen gas through it for 30 minutes. To (±)-5-bromo-7-dimethylamino-bicyclo[2.2.1]heptan-2-one (200 mg, 0.75 mmol) and azoisobutyronitrile (12 mg, 0.07 mmol) in a nitrogen atmosphere was added the degassed toluene (8 mL). To this was added tributyltin hydride (221 µL, 0.82 mmol) and the solution was stirred under a nitrogen atmosphere at 80° C. for 1 hour. A toluene (300 µL) solution of tributyltin hydride (30 µL, 0.11 mmol) and a few flakes of azoisobutyronitrile were added and the reaction was heated at 80° C. for 1.5 hours. The reaction mixture was evaporated to give 0.5 g of a yellow liquid that was chromatographed on a column of silica gel eluting with pentane, then 20% Et$_2$O in pentane up to 100% Et$_2$O to provide a colourless oil 214 mg (>100%, tin residue contamination). TLC: Rf 0.25 (50% Et$_2$O in pentane); $^1$H NMR (CDCl$_3$, 400 MHz): including signals for tin residues. δ 0.90 (3H, t, J=7.4 Hz), 1.35 (6H, m), 1.61 (2H, m), 1.98 (2H, m), 2.09 (2H, m), 2.18 (6H, s), 2.25 (1H, s), 2.53 (1H, t, J=4.4 Hz), 2.58 (1H, d, J=4.8 Hz).

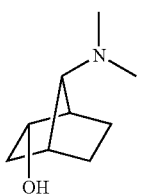

c. (±)-anti-7-Dimethylamino-bicyclo[2.2.1]heptan-2-ol. (IV-a): $R^a$, $R^b$=CH$_3$ To a chilled (−10° C.) THF (4 mL) solution of (±)-7-dimethylamino-bicyclo[2.2.1]heptan-2-one (214 mg, ≦0.75 mmol) was added lithium tri-tert-butoxyaluminohydride (380 mg, 1.49 mol.) The reaction mixture was stirred at 0° C. for 1.5 hours and then another portion of lithium tri-tert-butoxyaluminohydride (190 mg, 0.75 mol) was added and the reaction mixture was stirred for a further 1.5 hours. The reaction mixture was diluted with DCM and directly evaporated on to diatomaceous earth and chromatographed on a column of silica gel eluting with 5% MeOH in DCM with a 2.5% MeOH gradient up to 20% MeOH in DCM to give 120 mg (100%) of the title product as a white solid. $^1$H NMR spectroscopy indicated the solid was a 93:7 mixture of the title product and its (±)-2-epi isomer. The isomers were not separated. TLC: Rf 0.1 (75% Et$_2$O in pentane); $^1$H NMR (d$_4$-MeOH, 400 MHz): δ 0.96 (1H, dd, J=4.0 Hz, 13.2 Hz), 1.31 (1H, m), 1.56 (1H, m), 1.80 (1H, m), 1.93 (1H, m), 2.01 (1H, m), 2.17 (1H, m), 2.28 (8H, s), 4.14 (1H, m).

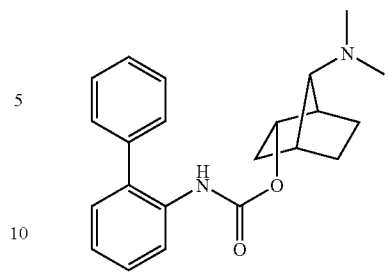

d. (±)-anti-Biphenyl-2-yl-carbamic acid 7-dimethylamino-bicyclo[2.2.1]hept-2-yl ester To a DMF (1.5 mL) and toluene (0.5 mL) solution of (±)-7-dimethylamino-bicyclo[2.2.1]heptan-2-ol (120 mg, 0.75 mmol) was added some powdered 3 Å molecular sieves and 2-biphenylisocyanate (189 mg, 0.97 mmol). The reaction mixture was stirred at 50° C. for 15.5 hours and was then diluted with EtOAc and washed twice with water, then with brine, dried (Na$_2$SO$_4$), filtered and evaporated to give 358 mg of a colourless syrup. This was purified on a column of silica gel eluting with 2-4% MeOH in DCM giving two fractions (143 mg) of differing purities. The purer fraction collected (91 mg) was re-chromatographed on a column of silica gel eluting with 80% Et$_2$O in pentane giving three fractions, the purest of which contained the title compound effectively free of the (±)-2-epi isomer, 42 mg (16%). TLC: Rf 0.2 (100% Et$_2$O in pentane); LC-MS (Method 1): Rt 6.99 min, m/z 351 [MH]+; $^1$H NMR (CDCl$_3$, 400 MHz): δ 1.11 (1H, dd, J=3.6 Hz, 13.6 Hz), 1.25 (1H, m), 1.62 (2H, m), 1.83 (1H, m), 2.05 (2H, m), 2.13 (1H, t, J=4.4 Hz), 2.18 (6H, s), 2.56 (1H, m), 4.95 (1H, m), 6.60 (1H, bs), 7.13 (1H, dt, J=1.2 Hz, 7.4 Hz), 7.22 (1H, dd, J=1.6 Hz, 7.6 Hz), 7.33-7.44 (4H, m), 7.49 (2H, m), 8.09 (1H, d, J=8.0 Hz).

EXAMPLE 2 anti-Biphenyl-2-yl-carbamic acid 7-dimethylamino-bicyclo[2.2.1]hept-2-yl ester. (II-a): $R^a$, $R^b$=CH$_3$, $R^d$=biphenyl-2-ylcarbamyl (first eluting enantiomer)

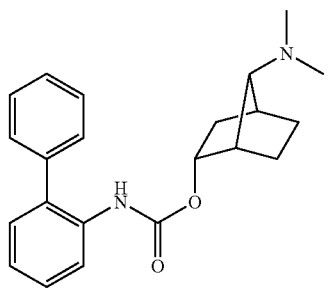

The title compound was isolated following preparative chiral HPLC of example 1 (Chiralpac IA, 250×20 mm i.d.; 12% tert butyl methyl ether/heptane/0.25% diethylamine; 14 mL/min; Rt 20.6 min). LC-MS (Method 1): Rt 7.03, m/z 351.2 [MH]+; NMR as obtained for example 1.

EXAMPLE 3 anti-Biphenyl-2-yl-carbamic acid 7-dimethylamino-bicyclo[2.2.1]hept-2-yl ester. (II-a): $R^a$, $R^b$=CH$_3$, $R^d$=biphenyl-2-ylcarbamyl (second eluting enantiomer)

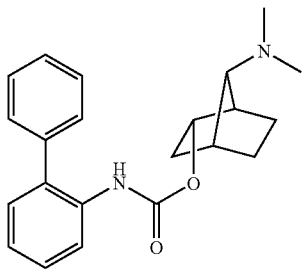

The title compound was isolated following preparative chiral HPLC of example 1 (Chiralpac IA, 250×20 mm i.d.; 12% tart butyl methyl ether/heptane/0.25% diethylamine; 14 mL/min; Rt 24 min). LC-MS (Method 1): Rt 7.07, m/z 351.2 [MH]+; NMR as obtained for example 1.

EXAMPLE 4

(±)-anti-[2-(Biphenyl-2-ylcarbamoyloxy)-bicyclo[2.2.1]hept-7-yl]-trimethyl-ammonium iodide. (I-a): $R^a$, $R^b$, $R^c$=CH$_3$, $R^d$=biphenyl-2-ylcarbamyl

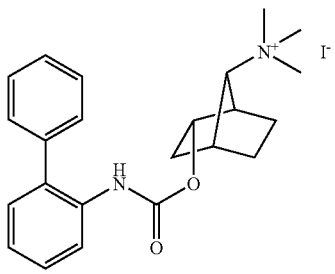

A solution of (±)-biphenyl-2-yl-carbamic acid 7-dimethylamino-bicyclo[2.2.1]hept-2-yl ester in methyl iodide (2.5 mL) was stirred at 40° C. for 21 hours. The reaction mixture was evaporated and the resultant solid was chromatographed on a column of silica gel eluting with 10% MeOH in DCM to give 61 mg (41%) of the title compound as a slightly yellow coloured solid. LC-MS (Method 3): Rt 2.2 min, m/z 365 [M]+; LC-MS (Method 1): Rt 7.16 min, m/z 365 [M]+; $^1$H NMR (CDCl$_3$, 400 MHz): δ 1.13 (1H, dd, J=3.2 Hz, 13.6 Hz), 1.60 (1H, m), 1.81 (1H, m), 1.99 (2H, m), 2.06 (1H, s), 2.41 (1H, m), 2.78 (1H, s), 3.11 (1H, t, J=3.8 Hz), 3.52 (9H, s), 4.00 (1H, s), 5.02 (1H, m), 6.63 (1H, s), 7.13 (1H, dt, J=0.8 Hz, 7.2 Hz), 7.22 (1H, dd, J=1.6 Hz, 8.0 Hz), 7.31-7.51 (6H, m), 7.95 (1H, d, J=6.4 Hz).

EXAMPLE 5

(±)-syn-Biphenyl-2-yl-carbamic acid 7-dimethylamino-bicyclo[2.2.1]hept-2-yl ester. (II-b): $R^a$, $R^b$=CH$_3$; $R^d$=biphenyl-2-ylcarbamyl

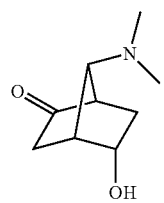

a. (±)-7-Dimethylamino-5-hydroxy-bicyclo[2.2.1]heptan-2-one. (XIV-b): $R^a$, $R^b$=CH$_3$ A solution of dimethylamine (2.0 M, 24 ml, 48 mmol) in THF was added to a solution of 2-bromo-bicyclo[3.2.0]heptan-3-ol (4.00 g, 19.5 mmol) in acetone (40 ml) at 0° C. and the mixture allowed to warm to ambient temperature over 1 h and stirred at ambient temperature overnight. The orange solution was filtered and the filtrate was evaporated to dryness. Purification was achieved by column chromatography on silica gel using 5% MeOH in DCM to yield 3.01 g (91%) of the product as a tan powder. LC-MS (Method 2): Rt 0.37 min, m/z 170.09 [MH]+.

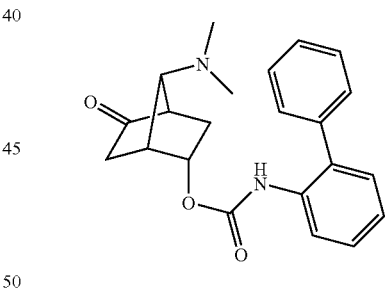

b. (±)-syn-Biphenyl-2-yl-carbamic acid 7-dimethylamino-5-oxo-bicyclo[2.2.1]hept-2-VI ester. (XIII-b): $R^a$, $R^b$=CH$_2$; $R^d$=biphenyl-2-ylcarbamyl 2-Biphenylisocyanate (90 μl, 0.52 mmol) was added to a solution of 7-dimethylamino-5-hydroxy-bicyclo[2.2.1]heptan-2-one (90 mg, 0.53 mmol) in toluene (1 ml) and the mixture heated at 70° C. overnight. The solvent was removed in vacuo and the residue purified by column chromatography using 100% DCM followed by 1% MeOH in DCM to yield the product as a white powder, 144 mg (75%). LC-MS (Method 1): Rt 6.50 min, m/z 365.15 [MH]+.

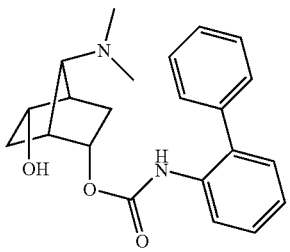

c. (±)-syn-Biphenyl-2-yl-carbamic acid 7-dimethylamino-5-hydroxy-bicyclo[2.2.1]hept-2-yl ester. (IV-b): $R^a$, $R^b$=CH$_3$; $R^d$=biphenyl-2-ylcarbamyl Sodium borohydride (25 mg, 0.68 mmol) was added to a solution of biphenyl-2-yl-carbamic acid 7-dimethylamino-5-oxo-bicyclo[2.2.1]hept-2-yl ester (200 mg, 0.55 mmol) in anhydrous MeOH at 0° C. and the mixture allowed to warm to ambient temperature over 1 h. The solvent was removed in vacuo and the residue purified by column chromatography using 100% DCM followed by 2% MeOH in DCM to yield 194 mg (97%) of the product as a white powder. LC-MS (Method 1): Rt 6.31, m/z 367.16 [MH]+.

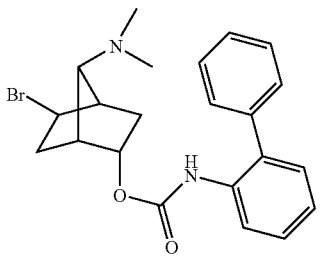

d. (±)-syn-Biphenyl-2-yl-carbamic acid 5-bromo-7-dimethylamino-bicyclo[2.2.1]hept-2-yl ester. (XII-b): $R^a$, $R^b$=CH$_3$; $R^d$=biphenyl-2-ylcarbamyl A suspension of biphenyl-2-yl-carbamic acid 7-dimethylamino-5-hydroxy-bicyclo[2.2.1]hept-2-yl ester (180 mg, 0.49 mmol), polymer-supported triphenylphosphine (2.18 mmol/g, 0.90 g, 1.96 mmol), tetrabromomethane (1.56 g, 4.71 mmol), and imidazole (130 mg, 1.91 mmol) in acetonitrile (4 ml) was stirred gently at 50° C. overnight. The solvent was removed in vacuo and the residue purified using HPLC (System 2: flow rate 18 ml/min, gradient of 0.25%/min increasing in B). The resulting TFA salt was converted to the free base by loading onto an SCX-2 cartridge followed by elution with NH$_3$/MeOH to give 45 mg (21%) of the title compound. LC-MS (Method 3): Rt 2.25 min, m/z 429.19/431.14 [MH]+.

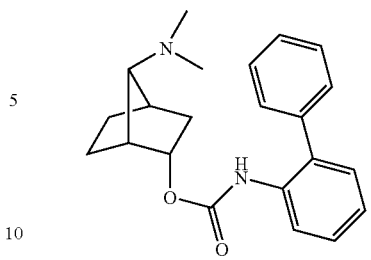

e. (±)-syn-Biphenyl-2-yl-carbamic acid 7-dimethylamino-bicyclo[2.2.1]hept-2-yl ester A solution of tributyltin hydride (40 µl, 0.15 mmol) in anhydrous toluene (200 µl) was added to a solution of biphenyl-2-yl-carbamic acid 5-bromo-7-dimethylamino-bicyclo[2.2.1]hept-2-yl ester (45 mg, 0.10 mmol) and 2,2'-azobis(2-methylpropionitrile) (10 mg, 0.06 mmol) in anhydrous toluene (0.8 ml) at 50° C. before stirring at 80° C. for 40 min. The solvent was removed in vacuo and the residue purified using HPLC (System 2: flow rate 18 ml/min, gradient of 4%/min increasing in B. UV detection at 210 nm). The resulting TFA salt was converted to the free base by passing through an SCX-2 cartridge to give 28 mg (76%) of the title compound. LC-MS (Method 1): Rt 7.18, m/z 351.19 [MH]+; (CDCl$_3$) δ 1.09 (1H, m), 1.36 (2H, m), 1.66 (2H, m), 2.13 (1H t, J=4.3 Hz), 2.24 (7H, s), 2.34 (1H, m), 2.54 (1H, t, J=4.0 Hz), 5.26 (1H, m), 6.58 (1H, s), 7.11 (1H, td, J=7.5, 1.2 Hz), 7.21 (1H, dd, J=7.5, 1.6 Hz), 7.34 (1H, m), 7.38 (2H, m), 7.41 (1H, m), 7.49 (2H, m), 8.11 (1H, d, J=8.2 Hz).

EXAMPLE 6 syn-Biphenyl-2-yl-carbamic acid 7-dimethylamino-bicyclo[2.2.1]hept-2-yl ester. (II-b): $R^a$, $R^b$=CH$_3$; $R^d$=biphenyl-2-ylcarbamyl (first eluting enantiomer)

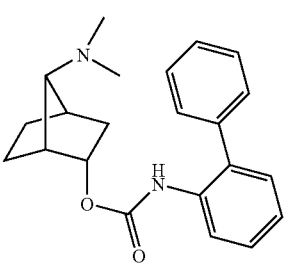

The title compound was isolated following preparative chiral HPLC of example 5 under conditions reported for example 2 (Rt 19 min). LC-MS (Method 1): Rt 7.16 min, m/z 351 [MH]+; NMR as obtained for example 5.

EXAMPLE 7 syn-Biphenyl-2-yl-carbamic acid 7-dimethylamino-bicyclo[2.2.1]hept-2-yl ester. (II-b): $R^a$, $R^b$=CH$_3$; $R^d$=biphenyl-2-ylcarbamyl (second eluting enantiomer)

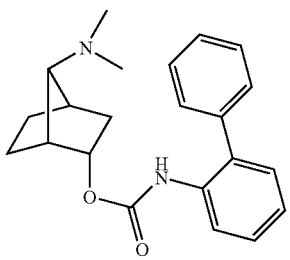

The title compound was isolated following preparative chiral HPLC of example 5 under conditions reported for example 2 (Rt 20.4 min). LC-MS (Method 1): Rt 7.14 min, m/z 351 [MH]+; NMR as obtained for example 5.

EXAMPLE 8

(±)-syn-[2-(Biphenyl-2-ylcarbamoyloxy)-bicyclo[2.2.1]hept-7-yl]-trimethyl-ammonium iodide. (I-b): $R^a$, $R^b$, $R^c$=CH$_3$, $R^d$=biphenyl-2-ylcarbamyl

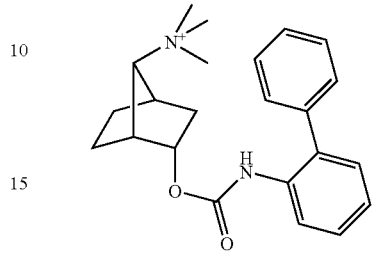

The title compound was prepared using conditions described for the preparation of example 4. LC-MS (Method 1): Rt 7.02, m/z 365 [M]+; (CDCl$_3$) δ 1.43 (1H, m), 1.50 (1H, dd, J=15.1, 3.8 Hz), 1.78 (1H, m), 1.88 (1H, m), 2.04 (1H, m), 2.51 (1H, m), 2.73 (1H, t, J=4.0 Hz), 2.96 (1H t, J=3.9 Hz), 3.54 (9H, s), 4.31 (1H, s), 5.33 (1H, m), 6.65 (1H, s), 7.17 (1H, m), 7.25 (1H, m), 7.37 (3H, m), 7.43 (1H, m), 7.50 (2H, m), 7.99 (1H, d, br).

The following examples were prepared in a similar manner to that described for example 1.

| Ex. | Name | Structure | $^1$H NMR (400 MHz) | Rt/min (Method 1); [MH]+ or [M]+ |
|---|---|---|---|---|
| 9 | anti-Biphenyl-2-yl-carbamic acid-7-[methyl-(3-phenoxy-propyl)-amino]bicyclo[2.2.1]hept-2-yl ester. Enantiomer 1. | 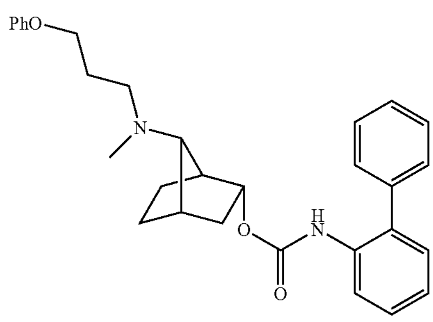 | (CDCl$_3$) δ 1.09(1H, dd, J = 13.6, 3.6 Hz), 1.16(1H, m), 1.57(2H, m), 1.79(1H, m), 1.90(2H, pent, J = 6.6 Hz), 2.05(1H, m), 2.14(1H, t, J = 4.4 Hz), 2.16(3H, s), 2.29 (1H, s), 2.51(2H, m), 2.56 (1H, t, J = 4.0 Hz), 3.98(2H, t, J = 6.6 Hz), 4.93(1H, m), 6.57(1H, s), 6.88(2H, m), 6.92(1H, m), 7.12(1H, m), 7.21(1H, m), 7.26(2H, m), 7.36(3H, m), 7.41(1H, m), 7.48(2H, m), 8.08(1H, d, br, J = 8.0 Hz) | 8.63; 471 |
| 10 | anti-Biphenyl-2-yl-carbamic acid-7-[methyl-(3-phenoxy-propyl)-amino]-bicyclo[2.2.1]hept-2-yl ester. Enantiomer 2. | 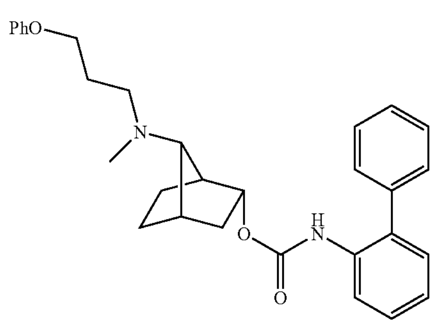 | (CDCl$_3$) δ 1.09(1H, dd, J = 13.6, 3.6 Hz), 1.16(1H, m), 1.57(2H, m), 1.79(1H, m), 1.90(2H, pent, J = 6.6 Hz), 2.05(1H, m), 2.14(1H, t, J = 4.4 Hz), 2.16(3H, s), 2.29 (1H, s), 2.51(2H, m), 2.56 (1H, t, J = 4.0 Hz), 3.98(2H, t, J = 6.6 Hz), 4.93(1H, m), 6.57(1H, s), 6.88(2H, m), 6.92(1H, m), 7.12(1H, m), 7.21(1H, m), 7.26(2H, m), 7.36(3H, m), 7.41(1H, m), 7.48(2H, m), 8.08(1H, d, br, J = 8.0 Hz) | 8.60; 471 |

-continued

| Ex. | Name | Structure | ¹H NMR (400 MHz) | Rt/min (Method 1); [MH]+ or [M]+ |
|---|---|---|---|---|
| 11 | anti-2-(Biphenyl-2-ylcarbamoyloxy)bicyclo[2.2.1]hept-7-yl]-dimethyl-(3-phenoxy-propyl)-ammonium iodide. Enantiomer prepared from example 9. | 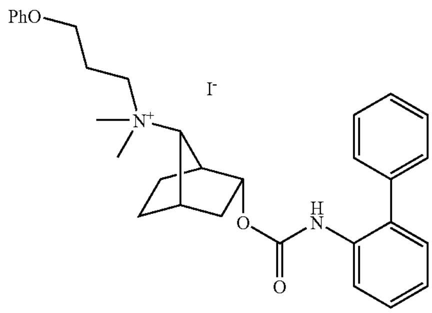 | (CDCl$_3$) δ 1.10(1H, dd, J = 13.7, 3.4 Hz), 1.58(1H, m), 1.80(1H, m), 2.00(2H, m), 2.37(3H, m), 2.77(1H, t, br, J = 3.8 Hz), 3.11(1H, t, br, J = 3.8 Hz), 3.39(3H, s), 3.41 (3H, s), 3.87(1H, s), 3.90 (2H, m), 4.11(2H, t, J = 5.4 Hz), 5.02(1H, m), 6.63 (1H, s), 6.90(2H, m), 6.93 (1H, m), 7.13(1H, td, J = 7.5, 1.2 Hz), 7.24(3H, m), 7.34 (3H, m), 7.42(1H, m), 7.49 (2H, m), 7.98(1H, d, br, J = 7.4 Hz) | 8.84; 485 |
| 12 | anti-2-(Biphenyl-2-ylcarbamoyloxy)bicyclo[2.2.1]hept-7-yl]-dimethyl-(3-phenoxy-propyl)-ammonium iodide. Enantiomer prepared from example 10. | 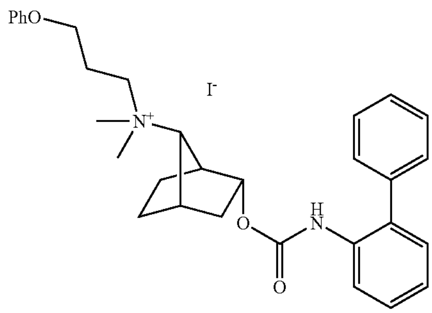 | (CDCl$_3$) δ 1.10(1H, d, J = 13.7 Hz), 1.58(1H, m), 1.80 (1H, m), 2.00(2H, m), 2.37 (3H, m), 2.77(1H, s, br), 3.11(1H, s br), 3.39(3H, s), 3.40(3H, s), 3.87(1H, s), 3.90(2H, m), 4.12(2H, t, J = 5.4 Hz), 5.02(1H, m), 6.63 (1H, s), 6.90(2H, m), 6.93 (1H, m), 7.13(1H, t, J = 7.5 Hz), 7.24(3H, m), 7.34 (3H, m), 7.42(1H, m), 7.49 (2H, m), 7.98(1H, d, br, J = 7.4 Hz) | 8.81; 485 |

EXAMPLE 13 anti-[(1S,2R)-2-(2-Hydroxy-2,2-di-thiophen-2-yl-acetoxy)bicyclo[2.2.1]hept-7-yl]-dimethyl-(3-phenylpropyl)ammonium bromide: (II-a): $R^a$, $R^c$=Me, $R^b$=3-Phenyl-propyl, $R^d$=2,2-di-thiophen-2-yl-acetoxy

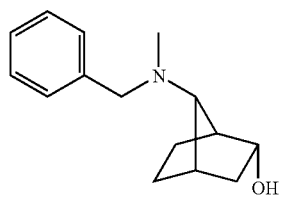

a. anti-(1S,2R)-7-(Benzylmethylamino)-bicyclo[2.2.1]heptan-2-ol

The title compound was prepared from (1S,2R,3R)-2,3-dibromo-bicyclo[3.2.0]heptan-6-one and N-methyl benzylamine using analogous methods to those in Example 1. LC-MS (Method 2): Rt 0.76 min, m/z 232 [MH]+.

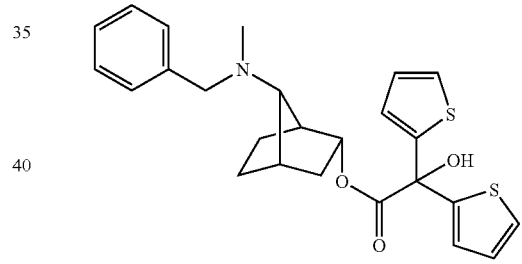

b. anti-Hydroxy-di-thiophen-2-yl-acetic acid (1S,2R)-7-(benzylmethylamino)-bicyclo[2.2.1]hept-2-yl ester To a cooled (0° C.) solution of anti-(1S,2R)-7-(benzylmethylamino)-bicyclo[2.2.1]heptan-2-ol (1 g, 4.3 mmol) was added sodium hydride (432 mg of 60% suspension in mineral oil, 10.8 mmol) portionwise. The mixture was allowed to warm to ambient temperature for 10 minutes then re-cooled to 0° C. Hydroxy-di-thiophen-2-yl-acetic acid ethyl ester (1.39 g, 5.2 mmol) was added portionwise and then the mixture was heated at 80° C. for 2 hours. After allowing the mixture to cool to ambient temperature the reaction was quenched by dropwise addition of aqueous ammonium chloride (sat. 50 mL) then extracted with ethyl acetate (3×100 mL). Combined organics were dried over sodium sulfate, filtered and evaporated to a yellow oil. Purification by flash column over silica gel using 5-10% ethyl acetate in hexane as JO eluent then by a further flash column using 0-5% ethyl acetate in DCM gave 1.12 g (57%) of the title compound as a yellow oil: LC-MS (Method 2): Rt 2.44 min, m/z 454 [MH]+.

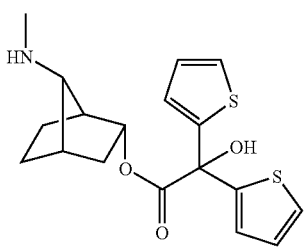

c. anti-Hydroxy-di-thiophen-2-yl-acetic acid (1S, 2R)-7-methylaminobicyclo[2.2.1]hept-2-yl ester To a solution of anti-hydroxy-di-thiophen-2-yl-acetic acid (1S,2R)-7-(benzylmethyl-amino)-bicyclo[2.2.1]hept-2-yl ester (400 mg, 0.88 mmol) in 1,2-dichloroethane (5 mL) was added 1-chloroethyl chloroformate (0.57 mL, 5.3 mmol) and the mixture was heated at 80° C. for 8 hours. The solvent and excess 1-chloroethyl chloroformate were removed under reduced pressure leaving a yellow/brown oil. This was re-dissolved in methanol (5 mL) and stirred at ambient temperature for 1 hour then evaporated to a yellow foam. The residue was suspended in water (10 mL) and basified using sodium hydroxide (0.1N) then extracted with ethyl acetate (4×20 mL). The combined organics were dried over sodium sulfate, filtered and evaporated to a brown solid. Purification by flash chromatography over silica gel using 5-10% methanol in DCM as eluent gave 180 mg (56%) of the title compound as a yellow solid: LC-MS (Method 2): Rt 2.20 min, m/z 364 [MH]+.

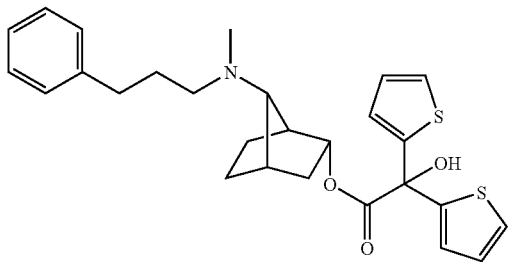

d. anti-Hydroxy-di-thiophen-2-yl-acetic acid (1S, 2R)-7-[methyl-(3-phenyl-propyl)-amino]-bicyclo[2.2.1]hept-2-yl ester To a solution of anti-hydroxy-di-thiophen-2-yl-acetic acid (1S,2R)-7-methylamino-bicyclo[2.2.1]hept-2-yl ester (150 mg, 0.41 mmol) in 1,2-dichloroethane (10 mL) was added 3-phenyl propanal (55 μL, 0.41 mmol). The mixture was stirred at ambient temperature for 10 minutes then sodium triacetoxyborohydride (174 mg, 0.82 mmol) was added and the mixture stirred at ambient temperature for 2 hours. Aqueous sodium hydrogen carbonate (sat. 10 mL) was added and the mixture separated through a phase separation cartridge, washing the aqueous phase with DCM. The combined organics were evaporated to a yellow oil. Purification by flash chromatography over silica gel using 0-10% ethyl acetate in DCM as eluent gave 150 mg (76%) of the title compound: LC-MS (Method 2): Rt 2.65 min, m/z 482 [MH]+.

e. anti-[(1S,2R)-2-(2-Hydroxy-2,2-di-thiophen-2-yl-acetoxy)-bicyclo[2.2.1]hept-7-yl]-dimethyl-(3-phenyl-propyl)-ammonium bromide

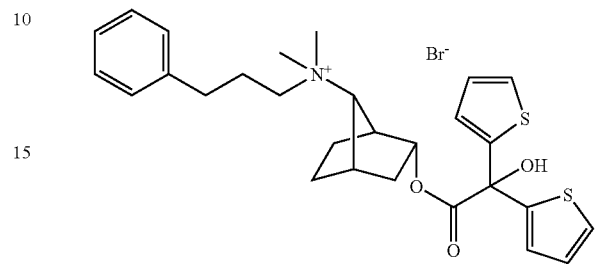

A solution of anti-hydroxy-di-thiophen-2-yl-acetic acid (1S,2R)-7-[methyl-(3-phenyl-propyl)-amino]-bicyclo[2.2.1]hept-2-yl ester (150 mg, mmol) in a 30% w/w solution of methyl bromide in acetonitrile (5 mL) was heated in a sealed tube for 3 days at 60° C. The solvent was removed and the residue purified by flash chromatography over silica gel using 5-10% methanol in DCM as eluent to give 100 mg (65%) of the title compound as a white solid: LC-MS (Method 1): Rt 8.43 min, m/z 496 [M]+; $^1$H NMR (DMSO, 400 MHz) δ 1.01 (1H, dd, J=13.4 Hz, 3.1 Hz), 1.35 (1H, m), 1.69 (2H, m), 1.95 (1H, m), 2.04 (2H, m), 2.19 (1H, m), 2.61 (3H, m), 2.93 (1H, t, br, J=3.5 Hz), 3.07 (3H, s), 3.06 (3H, s), 3.39 (2H, m), 3.53 (1H, s), 5.0 (1H, m), 7.01 (2H, m), 7.10 (2H, m), 7.22 (1H, m), 7.27 (2H, m), 7.32 (2H, m), 7.39 (1H, s), 7.51 (2H, m).

EXAMPLE 14 AND 15 trans-1-anti-[(1S,2R)-2-(2-Hydroxy-2,2-di-thiophen-2-yl-acetoxy)-bicyclo[2.2.1]hept-7-yl]-1-methyl-4-phenylpiperidinium bromide and cis-1-anti-[(1S,2R)-2-(2-Hydroxy-2,2-di-thiophen-2-yl-acetoxy)-bicyclo[2.2.1]hept-7-yl]-1-methyl-4-phenylpiperidinium bromide: (II-a): NR$^a$R$^b$=piperidinyl, R$^c$=Me, R$^d$=2, 2-dl-thiophen-2-yl-acetoxy

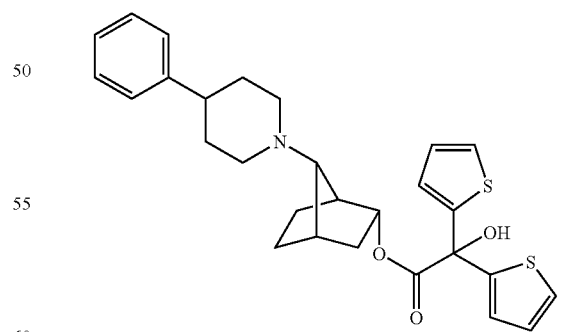

a. anti-Hydroxy-di-thiophen-2-yl-acetic acid (1S,2R)-7-(4-phenyl-piperidin-1-yl)-bicyclo[2.2.1]hept-2-yl ester The title compound was prepared from (1S,2R,3R)-2,3-dibromo-bicyclo[3.2.0]heptan-6-one and 4-phenylpiperidine using analogous methods to those in Examples 1 and 13. LC-MS (Method 2): Rt 2.60 min, m/z 494 [MH]+.

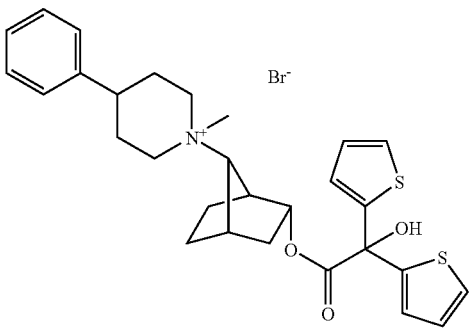

b. trans-1-anti-[(1S,2R)-2-(2-Hydroxy-2,2-di-thiophen-2-yl-acetoxy)-bicyclo[2.2.1]hept-7-yl]-1-methyl-4-phenyl-piperidinium bromide and cis-1-anti-[(1S,2R)-2-(2-Hydroxy-2,2-di-thiophen-2-acetoxy)-bicyclo[2.2.1]hept-7-yl]-1-methyl-4-phenyl-piperidinium bromide The title compounds were prepared from anti-hydroxy-di-thiophen-2-yl-acetic acid (1S,2R)-7-(4-phenylpiperidin-1-yl)bicyclo[2.2.1]hept-2-yl ester using a method analogous to example 13, then separated using column chromatography over silica gel using 5-15% methanol in DCM as eluent:

trans-1-anti-[(1S,2R)-2-(2-Hydroxy-2,2-di-thiophen-2-yl-acetoxy)-bicyclo[2.2.1]hept-7-yl]-1-methyl-4-phenylpiperidinium bromide: LC-MS (Method 1): Rt 8.06 min, m/z 508 [M]+; (CDCl$_3$) δ 1.27 (1H, m), 1.57 (1H, m), 1.77 (1H, m), 1.86 (1H, m), 2.06 (3H, m), 2.20 (2H, d, J=15.3 Hz), 2.40 (1H, m), 2.86 (1H, t, br, J=3.7 Hz), 3.03 (1H, t, br, J=3.7 Hz), 3.42 (1H, m), 3.61 (3H, s), 3.65 (1H, d, J=13.6 Hz), 3.69 (1H, s), 3.82 (1H, d, J=13.6 Hz), 4.50 (2H, m), 4.66 (1H, s), 5.16 (1H, m), 7.00 (2H, m), 7.17 (2H, m), 7.23 (2H, m), 7.26 (1H, m), 7.33 (4H, m).

cis-1-anti-[(1S,2R)-2-(2-Hydroxy-2,2-di-thiophen-2-yl-acetoxy)-bicyclo[2.2.1]hept-7-yl]-1-methyl-4-phenylpiperidinium bromide: LC-MS (Method 1): Rt 8.10 min, m/z 508 [M]+; (CDCl$_3$) δ 1.16 (1H, dd, J=13.8, 3.0 Hz), 1.52 (1H, m), 1.72 (2H, m), 2.08 (5H, m), 2.59 (1H, m), 2.86 (1H, t, br, J=4.0 Hz), 3.09 (1H, m), 3.20 (1H, s, br), 3.36 (3H, s), 3.82 (2H, d, J=12.2 Hz), 3.99 (2H, t, J=12.2 Hz), 4.63 (1H, s), 5.01 (1H, s), 5.32 (1H, m), 6.96 (2H, m), 7.16 (2H, m), 7.24 (5H, m), 7.31 (2H, m).

The following examples were prepared in a similar manner to that described for examples 13-14.

| Ex. | Name | Structure | $^1$H NMR (400 MHz) | Rt/min (Method 1); [MH]+ or [M]+ |
|---|---|---|---|---|
| 16 | (±) anti-Hydroxy-di-thiophen-2-yl-acetic acid 7-[methyl-(3-phenoxy-propyl)-amino]-bicyclo[2.2.1]hept-2-yl ester | 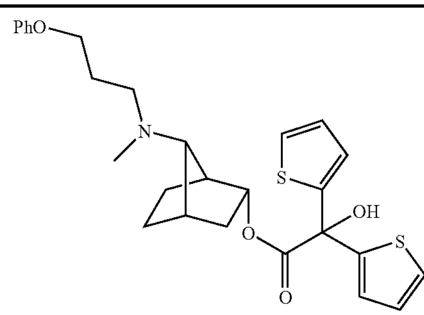 | (CDCl$_3$) δ 1.08(1H, m), 1.10 (1H, dd, J = 13.7, 3.4 Hz), 1.40(1H, m), 1.56(1H, m), δ 1.77(1H, m), 1.89(2H, pent, J = 6.5 Hz), 2.09(1H, m), 2.15(3H, s), 2.19(1H, m), 2.28(1H, s), 2.50(2H, m), 2.52(1H, m), 3.98(2H, t, j = 6.5 Hz), 5.07(1H, m), 6.87 (2H, m), 6.93(1H, m), 6.98 (2H, m), 7.16(1H, dd, J = 3.7, 1.3 Hz), 7.19(1H, dd, J = 3.7, 1.3 Hz), 7.27(4H, m) | 8.16; 498 |
| 17 | (±) anti-2-(2-Hydroxy-2,2-di-thiophen-2-yl-acetoxy)-bicyclo[2.2.1]hept-7-yl]-dimethyl-(3-phenoxy-propyl)-ammonium acetate | 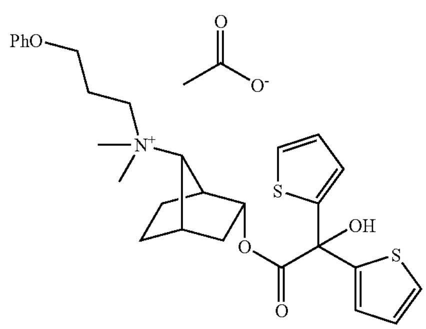 | (CDCl$_3$) δ 1.10(1H, dd, J = 13.6, 2.5 Hz), 1.45(1H, m), 1.63(1H, m), 1.75(1H, m), 1.88(1H, m), 2.28(2H, m), 2.37(1H, m), 2.67(1H, s, br), 3.07(1H, s, br), 3.23 (3H, s), 3.24(3H, s), 3.70 (2H, m), 3.87(1H, s), 4.04 (2H, t, J = 5.1 Hz), 5.14(1H, m), 6.85(2H, m), 6.94(3H, m), 7.14(2H, m), 7.24(4H, m) | 8.20; 512 |
| 18 | anti-(1R,2S)-2-(2-Hydroxy-2,2-di-thiophen-2-yl-acetoxy)-bicyclo[2.2.1]hept-7-yl]-dimethyl-(3-phenoxy-propyl)-ammonium iodide | 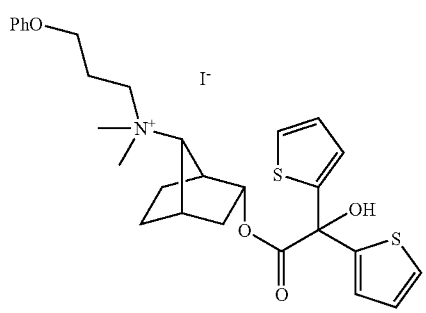 | (CDCl$_3$) δ 1.24(1H, m), 1.57 (1H, m), 1.68(1H, m), 1.76 (1H, m), 1.97(1H, m), 2.38 (2H, m, br), 2.53(1H, m), 2.82(1H, t, br, J = 3.0 Hz), 3.13(1H, t, br, J = 3.0 Hz), 3.38(3H, s), 3.39(3H, s), 3.95(2H, m), 4.05(1H, s), 4.15(2H, t, J = 4.8 Hz), 4.62 (1H, s), 5.21(1H, m), 6.89 (2H, m), 6.99(3H, m), 7.16 (1H, dd, J = 3.7, 1.3 Hz) 7.18 (1H, dd, J = 3.7, 1.3 Hz), 7.29 (4H, m). | 8.15; 512 |

-continued

| Ex. | Name | Structure | ¹H NMR (400 MHz) | Rt/min (Method 1); [MH]+ or [M]+ |
|---|---|---|---|---|
| 19 | anti-(±)-2-(2-Hydroxy-2,2-di-thiophen-2-yl-acetoxy)-bicyclo[2.2.1]hept-7-yl]-dimethyl-(3-phenyl-propyl)-ammonium bromide | 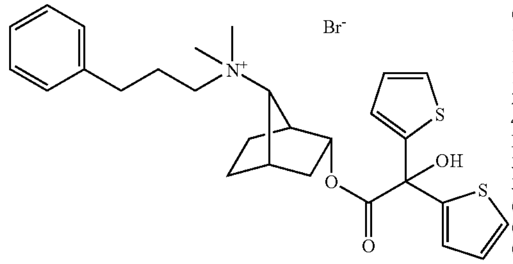 | (CD₃OD) δ 1.16(1H, dd, J = 13.7, 3.3 Hz), 1.46(1H, m), 1.70(1H, m), 1.80(1H, m), 1.97(1H, m), 2.15(2H, m), 2.26(2H, m), 2.62(1H, t, J = 4.2 Hz), 2.71(2H, t, J = 7.5 Hz), 2.94(1H, t, J = 4 Hz), 3.12(6H, s), 3.41(2H, m), 3.50(1H, s), 5.05(1H, m), 7.0 (2H, m), 7.15(2H, m), 7.20 (1H, m), 7.29(4H, m), 7.40 (2H, m). | 8.28; 496 |
| 20 | anti-(1S,2R)-2-(2-Hydroxy-2,2-di-thiophen-2-yl-acetoxy)-bicyclo[2.2.1]hept-7-yl]-dimethyl-(3-phenoxy-propyl)-ammonium iodide | 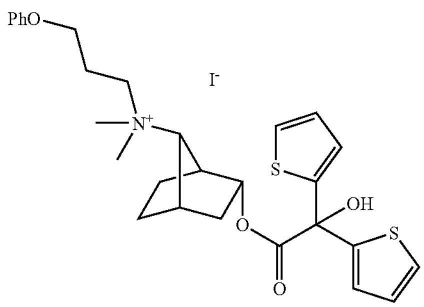 | (CDCl₃) δ 1.24(1H, m), 1.57 (1H, m), 1.68(1H, m), 1.76 (1H, m), 1.97(1H, m), 2.38 (2H, m, br), 2.53(1H, m), 2.82(1H, t, br, J = 3.0 Hz), 3.13(1H, t, br, J = 3.0 Hz), 3.38(3H, s), 3.39(3H, s), 3.95(2H, m), 4.05(1H, s), 4.15(2H, t, J = 4.8 Hz), 4.62 (1H, s), 5.21(1H, m), 6.89 (2H, m), 6.99(3H, m), 7.16 (1H, dd, J = 3.7, 1.3 Hz) 7.18 (1H, dd, J = 3.7, 1.3 Hz), 7.29 (4H, m) | 8.25; 512 |
| 21 | anti-(1S,2R) [2-(2-Hydroxy-2,2-di-thiophen-2-yl-acetoxy)-bicyclo[2.2.1]hept-7-yl]-dimethyl-(3-phenoxy-propyl)-ammonium toluene-4-sulfonate | 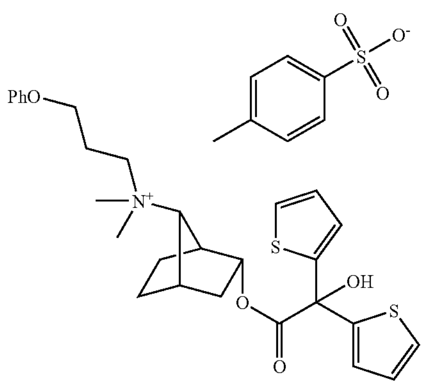 | (CDCl₃) δ 1.13(1H, dd, J = 13.6, 3.1 Hz), 1.47(1H, m), 1.63(1H, m), 1.71(1H, m), 1.91(1H, m), 2.29(3H, s), 2.29(2H, m), 2.41(1H, m), 2.72(1H, t, br, J = 3.5 Hz), 3.09(1H, t, br, J = 3.5 Hz), 3.30(3H, s), 3.31(3H, s), 3.79(2H, m), 3.86(1H, s), 4.00(2H, t, J = 5.3 Hz), 4.83 (1H, s), 5.13(1H, m), 6.82 (2H, m), 6.95(1H, m), 6.98 (2H, m), 7.09(2H, d, J = 8.1 Hz), 7.15(2H, m), 7.25(2H, m), 7.29(2H, m), 7.74(2H, m) | 8.25; 512 |
| 22 | anti-[(1S,2R)-2-(2-Hydroxy-2,2-di-thiophen-2-yl-acetoxy)-bicyclo[2.2.1]hept-7-yl]-dimethyl-phenethyl-ammonium bromide | 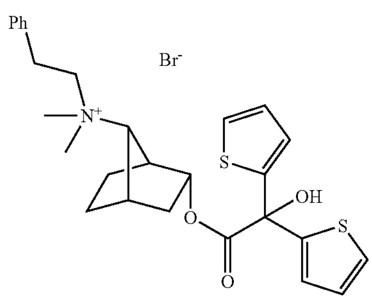 | (d₆-DMSO) δ 1.03(1H, dd, J = 13.4 Hz, 3.1 Hz), 1.37(1H, m), 1.72(2H, m), 2.00(1H, m), 2.22(1H, m), 2.70(1H, t, br, J = 3.5 Hz), 3.01(1H, t, br, J = 3.5 Hz), 3.09(2H, m), 3.15(3H, s), 3.17(3H, s), 3.59(3H, m), 5.03(1H, m), 7.01(2H, m), 7.10(2H, m), 7.29(1H, dd, J = 3.6, 1.3 Hz), 7.36(4H, m), 7.39(1H, s), 7.51(2H, m) | 7.87; 482 |
| 23 | Benzyl-anti-[(1S,2R)-2-(2-hydroxy-2,2-di-thiophen-2-yl-acetoxy)-bicyclo[2.2.1]hept-7-yl]-dimethyl-ammonium bromide | 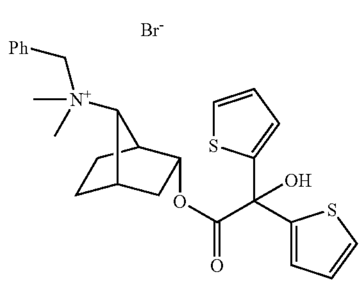 | (d₆-DMSO) δ 1.05(1H, dd, J = 13.4, 3.2 Hz), 1.37(1H, m), 1.67(1H, m), 1.78(1H, m), 2.02(1H, m), 2.18(1H, m), 2.63(1H, t, br, J = 4.0 Hz), 2.98(1H, t, br, J = 4 Hz), 3.00 (6H, s), 3.59(1H, s), 4.60 (2H, s), 4.98(1H, m), 7.01 (2H, m), 7.10(2H, m), 7.40 (1H, m), 7.53(5H, m), 7.60 (2H, m) | 7.38; 468 |

-continued

| Ex. | Name | Structure | $^1$H NMR (400 MHz) | Rt/min (Method 1); [MH]+ or [M]+ |
|---|---|---|---|---|
| 24 | anti-[(1S,2R)-2-(2-Hydroxy-2,2-di-thiophen-2-yl-acetoxy)-bicyclo[2.2.1]hept-7-yl]-dimethyl-(4-phenyl-butyl)-ammonium bromide | 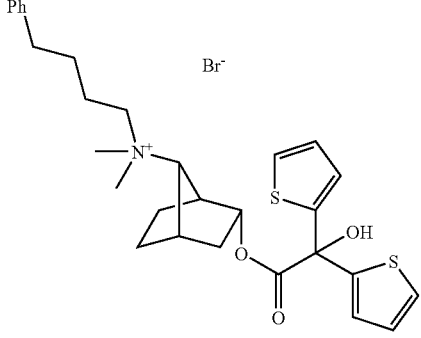 | (CDCl$_3$) δ 1.14(1H, dd, J = 13.9, 3.1 Hz), 1.48(1H, m), 1.62(1H, m), 1.73(5H, m), 1.91(1H, m), 2.44(1H, m), 2.70(3H, m), 2.98(1H, t, br, J = 3.8 Hz), 3.29(3H, s), 3.30(3H, s), 3.66(2H, m), 4.04(1H, s), 4.80(1H, s), 5.15(1H, m), 6.98(2H, m), 7.17(5H, m), 7.26(2H, m), 7.29(2H, m) | Method 4: 7.73; 510 |
| 25 | anti-[(1S,2R)-2-(2-Hydroxy-2,2-di-thiophen-2-yl-acetoxy)-bicyclo[2.2.1]hept-7-yl]-trimethyl-ammonium bromide | 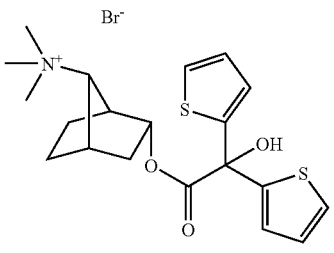 | (d$_6$-DMSO) δ 1.04(1H, dd, J = 13.4, 3.3 Hz), 1.35(1H, m), 1.68(2H, m), 1.96(1H, m), 2.17(1H, m), 2.67(1H, t, br, J = 4.0 Hz), 2.98(1H, t, br, J = 3.9 Hz), 3.13(9H, s), 3.55(1H, s), 4.97(1H, m), 7.01(2H, m), 7.10(2H, m), 7.39(1H, s), 7.51(2H, m) | 6.35; 392 |
| 26 | (2-Benzyloxy-ethyl)-anti-[(1S,2R)-2-(2-hydroxy-2,2-di-thiophen-2-yl-acetoxy)-bicyclo[2.2.1]hept-7-yl]-dimethyl-ammonium bromide | 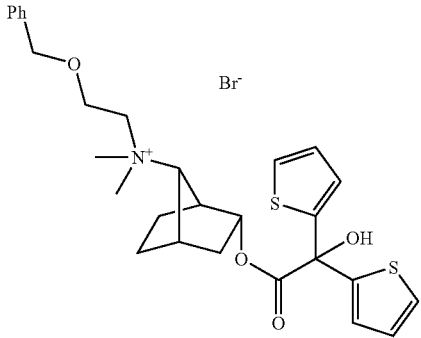 | (CD$_3$OD) δ 1.11(1H, dd, J = 13.6 Hz, 3.3 Hz), 1.47(1H, m), 1.75(1H, m), 1.81(1H, m), 2.00(1H, m), 2.15(1H, m), 2.66(1H, t, J = 4.1 Hz), 3.01(1H, t, J = 3.9 Hz), 3.204(3H, s), 3.20(3H, s), 3.57(1H, s), 3.70(2H, m), 3.95(2H, t, br, J = 4.0 Hz), 4.58(2H, s), 4.90(1H, s), 7.00(2H, m), 7.14(2H, m), 7.26-7.38(5H, m), 7.40(2H, m). | Method 4: 7.35; 512 |
| 27 | anti-[(1S,2R)-2-(2-Hydroxy-2,2-di-thiophen-2-yl-acetoxy)-bicyclo[2.2.1]hept-7-yl]-dimethyl-[2-(tetrahydro-pyran-4-yl)-ethyl]-ammonium bromide | 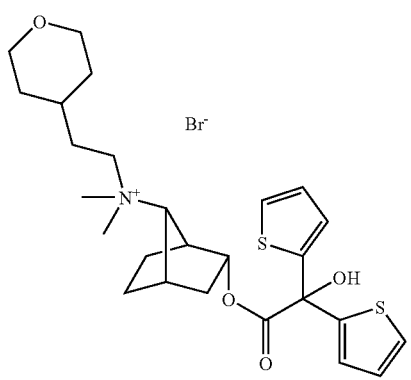 | (d$_6$-DMSO) δ 1.01(1H, dd, J = 13.4, 3.2 Hz), 1.23(2H, m), 1.35(1H, m), 1.51(1H, m), 1.60(2H, d, J = 13.1 Hz), 1.68(4H, m), 1.97(1H, m), 2.20(1H, m), 2.64(1H, t, br, J = 3.7 Hz), 2.96(1H, t, br, J = 3.5 Hz), 3.04(3H, s), 3.05(3H, s), 3.27(2H, m), 3.39(2H, m), 3.50(1H, s), 3.84(2H, m), 5.01(1H, m), 7.01(2H, m), 7.10(2H, dd, J = 3.6, 1.3 Hz), 7.39(1H, s), 7.51(2H, m) | 6.78; 490 |

| Ex. | Name | Structure | $^1$H NMR (400 MHz) | Rt/min (Method 1); [MH]+ or [M]+ |
|---|---|---|---|---|
| 28 | anti-(1S,2R) Hydroxy-di-thiophen-2-yl-acetic acid 7-(4-benzyl-piperidin-1-yl)-bicyclo[2.2.1]hept-2-yl ester | 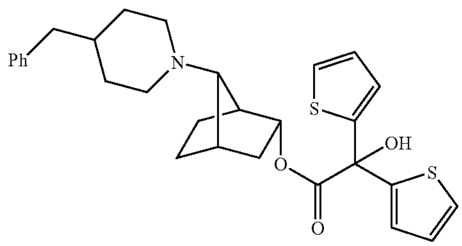 | (CDCl$_3$) δ 1.09(2H, m), 1.19 (2H, m), 1.44(2H, m), 1.59 (3H, m), 1.76(3H, m), 2.06 (1H, m), 2.10(1H, s), 2.15 (1H, t, J = 4.3 Hz), 2.51(3H, m), 2.81(2H, d, J = 11.4 Hz), 4.76(1H, s), 5.05(1H, m), 6.98(2H, m), 7.12(2H, m), 7.18(3H, m), 7.27(4H, m) | Method 4: 7.48, 508 |
| 29 | anti-(1S,2R) Hydroxy-diphenyl-acetic acid 7-(4-benzyl-piperidin-1-yl)-bicyclo[2.2.1]hept-2-yl ester | 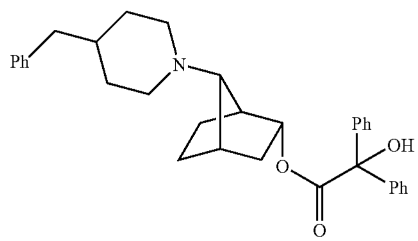 | (CDCl$_3$) δ 0.97(2H, m), 1.20 (3H, m), 1.51(5H, m), 1.73 (3H, m), 2.04(1H, m), 2.09 (1H, s), 2.11(1H, t, J = 4.4 Hz), 2.48(1H, m), 2.49 (2H, d, J = 7.0 Hz), 2.79(1H, m), 4.26(1H, m), 5.07(1H, m), 7.12(2H, m), 7.18(1H, m), 7.26(2H, m), 7.33(6H, m), 7.42(4H, m) | Method 4: 7.91, 496 |
| 30 | cis-4-Benzyl-1-[anti-(1S,2R)-2-(2-hydroxy-2,2-diphenyl-acetoxy)-bicyclo[2.2.1]hept-7-yl]-1-methyl-piperidinium bromide | 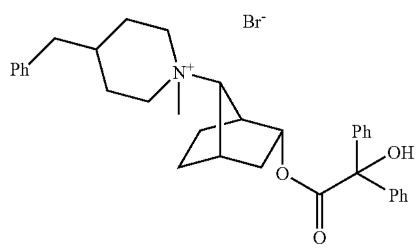 | (CDCl$_3$) δ 1.02(1H, dd, J = 13.8, 3.0 Hz), 1.30(1H, m), 1.45(2H, m), 1.74(5H, m), 2.00(1H, m), 2.55(1H, m), 2.62(2H, d, J = 7.0 Hz), 2.74 (1H, t, br, J = 4.0 Hz), 3.08 (1H, t, br, J = 4.0 Hz), 3.25 (3H, s), 3.66(4H, m), 4.20 (1H, s), 4.55(1H, s), 5.28 (1H, m), 7.11(2H, m), 7.20 (1H, m), 7.27(2H, m), 7.33 (8H, m), 7.41(2H, m) | Method 4: 8.30; 510 |
| 31 | trans-4-Benzyl-1-[anti-(1S,2R)-2-(2-hydroxy-2,2-diphenyl-acetoxy)-bicyclo[2.2.1]hept-7-yl]-1-methyl-piperidinium bromide | 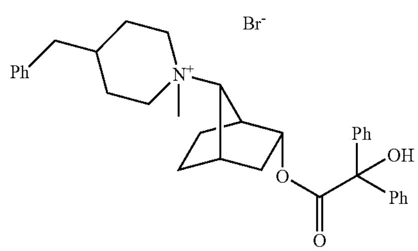 | (CDCl$_3$) δ 1.09(1H, dd, J = 13.8, 3.0 Hz), 1.35(1H, m), 1.57(4H, m), 1.92(3H, m), 2.36(2H, m), 2.70(3H, m), 2.93(1H, t, br, J = 4.0 Hz), 3.39(3H, s), 3.58(1H, d, br, J = 13.0 Hz), 3.74(2H, m), 4.05(1H, s), 4.07(2H, m), 5.16(1H, m), 7.17(2H, m), 7.21(1H, m), 7.28(2H, m), 7.38(10H, m) | Method 4: 8.24; 510 |
| 32 | anti-(1S,2R) Hydroxy-diphenyl-acetic acid 7-[methyl-(3-phenoxy-propyl)-amino]-bicyclo[2.2.1]hept-2-yl ester | 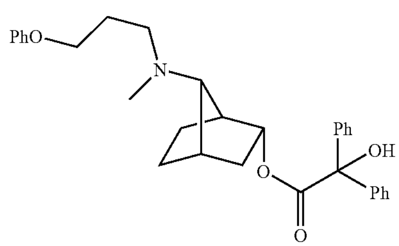 | (CDCl$_3$) δ 0.95(1H, m), 0.99 (1H, dd, J = 13.5, 3.3 Hz), 1.21(1H, m), 1.47(1H, m), 1.70(1H, m), 1.88(2H, pent, J = 6.5 Hz), 2.05(1H, m), 2.11(1H, m), 2.13(3H, s), 22.6(1H, s), 2.48(3H, m), 3.96(2H, t, J = 6.5 Hz), 4.26 (1H, s), 5.09(1H, m), 6.87 (2H, m), 6.93(1H, m), 7.26 (2H, m), 7.33(6H, m), 7.42 (4H, m) | 8.62; 486 |
| 33 | anti-(1S,2R) 2-(2-Hydroxy-2,2-diphenyl-acetoxy)-bicyclo[2.2.1]hept-7-yl]-dimethyl-(3-phenoxy-propyl)-ammonium bromide | 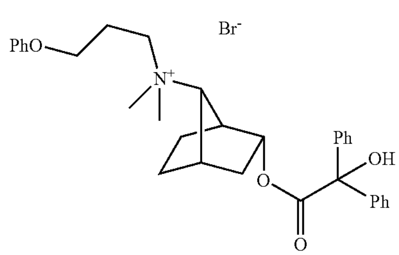 | (CDCl$_3$) δ 1.08(1H, dd, J = 13.8, 3.2 Hz), 1.36(1H, m), 1.51(2H, m), 1.87(1H, m), 2.36(2H, m), 2.47(1H, m), 2.75(1H, t, br, J = 4.0 Hz), 3.08(1H, t, br, J = 4.0 Hz), 3.38(3H, s), 3.40(3H, s), 3.93(2H, m), 4.11(4H, m), 5.23(1H, m), 6.87(2H, m), 6.97(1H, m), 7.27(2H, m), 7.35(8H, m), 7.42(2H, m) | 8.69; 500 |

| Ex. | Name | Structure | $^1$H NMR (400 MHz) | Rt/min (Method 1); [MH]+ or [M]+ |
|---|---|---|---|---|
| 34 | anti-(1S,2R) 9H-Xanthene-9-carboxylic acid 7-[methyl-(3-phenoxy-propyl)-amino]-bicyclo[2.2.1]hept-2-yl ester | 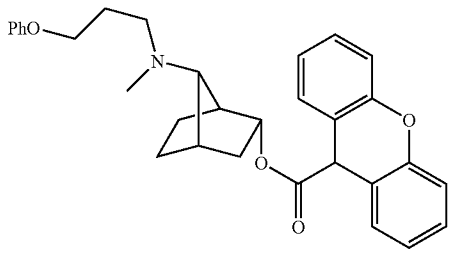 | (CDCl$_3$) δ 0.83(1H, dd, J = 13.7, 3.4 Hz), 0.96(1H, m), 1.26(1H, m), 1.44(1H, m), 1.69(1H, m), 1.86(2H, pent, J = 6.5 Hz), 1.93(1H, m), 2.05(1H, t, J = 4.0 Hz), 2.10 (3H, s), 2.18(1H, s), 2.38 (1H, t, J = 4.0 Hz), 2.44(2H, m), 3.95(2H, t, J = 6.5 Hz), 4.83(1H, m), 4.94(1H, s), 6.86(2H, m), 6.93(1H, m), 7.07(2H, m), 7.14(2H, m), 7.28(6H, m) | 9.29; 484 |
| 35 | anti-(1S,2R) 9-Hydroxy-9H-xanthene-9-carboxylic acid 7-[methyl-(3-phenoxy-propyl)-amino]-bicyclo[2.2.1]hept-2-yl ester | 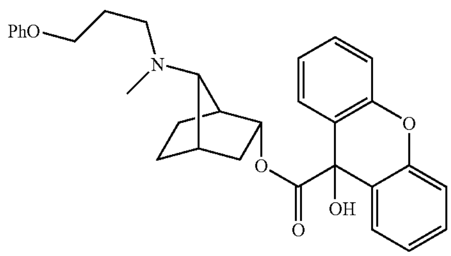 | (CDCl$_3$) δ 0.62(1H, dd, J = 13.8, 3.0 Hz), 0.66(1H, m), 0.77(1H, m), 1.25(1H, m), 1.55(1H, m), 1.83(3H, m), 1.96(1H, t, br, J = 4.0 Hz), 2.05(3H, s), 2.11(1H, s), 2.28(1H, t, br, J = 4.0 Hz), 2.40(2H, m), 3.91(2H, t, J = 6.4 Hz), 4.79(1H, m), 4.90 (1H, s), 6.84(2H, m), 6.93 (1H, m), 7.13(2H, m), 7.19 (2H, m), 7.26(2H, m), 7.35 (2H, m), 7.50(2H, m) | 2.53; 500 |
| 36 | anti-(1S,2R) Dimethyl-(3-phenoxy-propyl)-[2-(9H-xanthene-9-carbonyloxy)-bicyclo[2.2.1]hept-7-yl]-ammonium bromide | 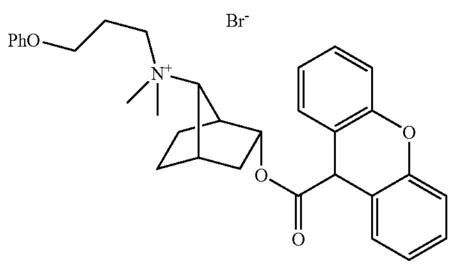 | (CDCl$_3$) δ 0.91(1H, dd, J = 13.7, 3.2 Hz), 1.37(1H, m), 1.58(2H, m), 1.89(1H, m), 2.27(3H, m), 2.68(1H, t, J = 4.0 Hz), 2.89(1H, t, J = 4.0 Hz), 3.32(3H, s), 3.35 (3H, s), 3.75(1H, s), 3.86 (2H, m), 4.07(2H, t, J = 5.5 Hz), 4.90(1H, m), 4.96 (1H, s), 6.84(2H, m), 6.95 (1H, m), 7.09(2H, m), 7.15 (2H, m), 7.28(6H, m) | 9.26; 499 |
| 37 | anti-(1S,2R) 2-(9-Hydroxy-9H-xanthene-9-carbonyloxy)-bicyclo[2.2.1]hept-7-yl]-dimethyl-(3-phenoxy-propyl)-ammonium bromide | 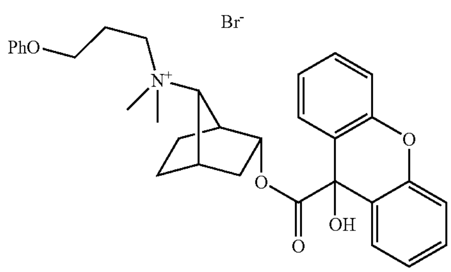 | (CDCl$_3$) δ 0.72(1H, dd, J = 13.8, 3.0 Hz), 1.13(1H, m), 1.22(1H, m), 1.37(1H, m), 1.77(1H, m), 2.23(1H, m), 2.30(2H, m), 2.62(1H, t, br, J = 4 Hz), 2.83(1H, t, br, J = 4.0 Hz), 3.31(3H, s), 3.33 (3H, s), 3.88(2H, m), 3.92 (1H, s), 4.08(2H, t, J = 5.4 Hz), 4.79(1H, s), 4.94 (1H, m), 6.83(2H, m), 6.96 (1H, m), 7.18(4H, m), 7.26 (2H, m), 7.37(2H, m), 7.50 (1H, dd, J = 7.8, 1.6 Hz), 7.54 (1H, dd, J = 7.8, 1.6 Hz) | Method 4: 7.55; 514 |
| 38 | anit-[(1S,2R)-2-(2-Hydroxy-2,2-di-thiophen-2-yl-acetoxy)-bicyclo[2.2.1]hept-7-yl]-indan-2-yl-dimethyl-ammonium bromide | 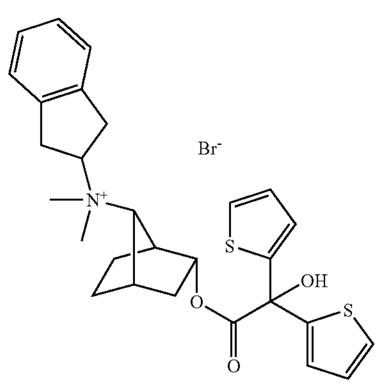 | (CDCl$_3$) δ 1.16(1H, m), 1.52 (1H, m), 1.74(2H, t), 2.03 (1H, m), 2.47(1H, m), 2.81 (1H, m), 3.11(1H, m), 3.34-3.46(8H, m), 3.48-3.58(2H, m), 4.07(1H, s), 4.74-4.81 (2H, m), 5.20(1H, m), 6.97 (2H, m), 7.14-7.30(8H, m). | Method 4: 7.42, 494 |

| Ex. | Name | Structure | $^1$H NMR (400 MHz) | Rt/min (Method 1); [MH]+ or [M]+ |
|---|---|---|---|---|
| 39 | Hydroxy-di-thiophen-2-yl-acetic acid anti-(1S,2R)-7-(carboxylmethyl-methyl-amino)-bicyclo[2.2.1]hept-2-yl ester | 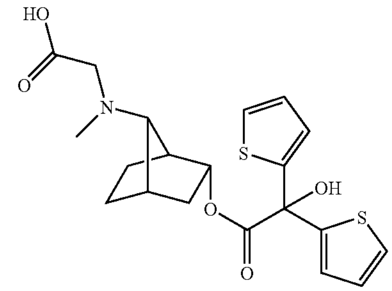 | (CDCl$_3$) δ 1.20(1H, m), 1.24-1.32(1H, m), 1.56(2H, m), 1.80(1H, m), 2.11-2.22(2H, m), 2.37(3H, s), 2.58(1H, br s), 2.73(1H, br s), 3.20(2H, m), 5.08(1H, m), 6.99(2H, q), 7.18(2H, m), 7.30(2H, m). | Method 4: 6.53, 422 |

EXAMPLE 40 anti-(1S,2R) 2-(2-Hydroxy-2,2-diphenyl-ethoxy)-bicyclo[2.2.1]hept-7-yl]-dimethyl-(3-phenoxy-propyl)-ammonium bromide a. 2-{anti-(1S,2R)-7-[Methyl-(3-phenoxy-propyl)-amino]-bicyclo[2.2.1]hept-2-yloxy}-1,1-diphenyl-ethanol

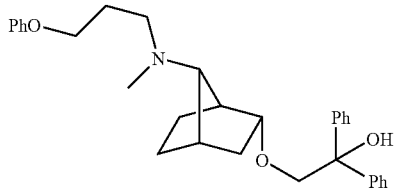

A solution of anti-(1S,2R)-7-[methyl-(3-phenoxy-propyl)-amino]-bicyclo[2.2.1]heptan-2-ol (177 mg, 0.64 mmol) in 5 mL DMSO was stirred under a nitrogen atmosphere at ambient temperature. Sodium hydride (45 mg, 60% dispersion in oil) was added and the reaction warmed to 70° C. for 60 minutes before being cooled to 50° C. 1,1-diphenylethylene oxide (256 mg, 1.31 mmol) was added to the anion and heating continued for 60 minutes. The reaction was cooled to ambient temperature, quenched by addition of water, extracted into EtOAc and the combined organic extracts washed with brine, dried over MgSO$_4$ and concentrated in vacuo. The reaction mixture was purified by chromatography on silica using a gradient of 0-15% Et$_2$O-cyclohexane as eluent to give the product as a clear oil (22 mg). LC-MS (Method 3): Rt 2.62 min, m/z 472 [MH]+;

b. anti-(1S,2R) 2-(2-Hydroxy-2,2-diphenyl-ethoxy)-bicyclo[2.2.1]hept-7-yl]-dimethyl-(3-phenoxy-propyl)-ammonium bromide The title compound was prepared from 2-{anti-(1S,2R)-7-[methyl-(3-phenoxy-propyl)-amino]-bicyclo[2.2.1]hept-2-yloxy}-1,1-diphenyl-ethanol using analogous methods to those described in example 13. LC-MS (Method 1): Rt 8.69 min, m/z 486 [M]+; (CDCl$_3$) δ 1.07 (1H, dd, J=13.3, 3.4 Hz), 1.60 (2H, m), 1.89 (1H, m), 2.09 (1H, m), 2.30 (1H, m), 2.37 (2H, m), 2.66 (1H, t, br, J=4.0 Hz), 2.93 (1H, t, br, J=4.0 Hz), 3.22 (1H, s), 3.37 (3H, s), 3.38 (3H, s), 3.09 (2H, s), 3.97 (2H, m), 4.07 (1H, s), 4.14 (2H, t, J=5.5 Hz), 4.17 (1H, m), 6.86 (2H, m), 6.96 (1H, m), 7.26 (3H, m), 7.31 (5H, m), 7.40 (4H, m)

EXAMPLE 41

Hydroxy-di-thiophen-2-yl-acetic acid (1S,2R,4S,7S)-7-({9-[(R)-2-hydroxy-2-(8-hydroxy-2-oxo-1,2-dihydro-quinolin-5-yl)-ethylamino]-nonyl}-methyl-amino)-bicyclo[2.2.1]hept-2-yl ester

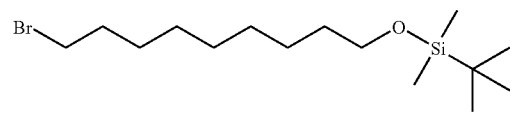

a. (9-Bromo-nonyloxy)-tert-butyl-dimethyl-silane

Tert-butyl-dimethylsilyl chloride (28.16 g, 186.8 mmol) was added in portions to a solution of 9-bromo-nonan-1-ol (27.8 g, 124.6 mmol) and imidazole (25.4 g, 373 mmol) in dry DCM (400 mL) at −10° C. under a nitrogen atmosphere. The reaction mixture was allowed to warm to RT overnight. The solids were removed by filtration and the filtrate was washed with 10% citric acid (aq), then brine, dried (MgSO$_4$), filtered, and concentrated to dryness to afford the title compound as a yellow oil.

Yield: 41.4 g, 98%.

TLC: Rf 0.91 (50% diethyl ether/cyclohexane).

b. [9-(tert-Butyl-dimethyl-silanyloxy)-nonyl]-methyl-amine

A solution of methylamine (120 mL, 2 M) was added to a solution of (9-bromo-nonyloxy)-tert-butyl-dimethyl-silane (41.4 g, 123 mmol) in IMS (200 mL) at −10° C. and then allowed to warm to RT overnight. After evaporation of the solvent the residue was triturated with diethyl ether and the solids were removed by filtration to afford the title compound as the HBr salt. The filtrate was concentrated in vacuo, suspended in K$_2$CO$_3$ (aq), and extracted with DCM. The combined organic layers were dried (MgSO$_4$), filtered, and concentrated to afford the title compound as an oil.

Yield: 24.1 g, 68% (11.1 g of HBr salt, 24%).

LC-MS (method 2): Rt 2.80 min, m/z 288 [MH+].

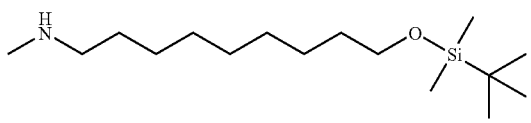

c. (1S,4S,7S)-5-Bromo-7-{[9-(tert-butyl-dimethyl-silanyloxy)-nonyl]-methyl-amino}-bicyclo[2.2.1]heptan-2-one.

To a solution of (1S)-2,3-dibromo-bicyclo[3.2.0]heptan-6-one (2.15 g, 8.02 mmol) in acetone (20 mL) was added [9-(tert-butyl-dimethyl-silanyloxy)-nonyl]-methyl-amine (5.77 g, 12.3 mmol) and the reaction mixture was stirred at RT for 3 days. After evaporation of the solvent the residue was taken up in diethyl ether/ethyl acetate and washed with a satd NaHCO$_3$ (aq)/brine mixture. The aqueous layer was extracted with diethyl ether. The combined organic layers were dried (Na$_2$SO$_4$), filtered, and concentrated to dryness to afford a dark brown oil, which was purified by column chromatography over silica gel using a gradient of 5-15% diethyl ether/pentane as eluent. After evaporation of the volatiles the title compound was obtained as a light yellow/brown oil.

Yield: 1.67 g, 44%.

LC-MS (method 3): Rt 4.83 min, m/z 474+476 [MH+].

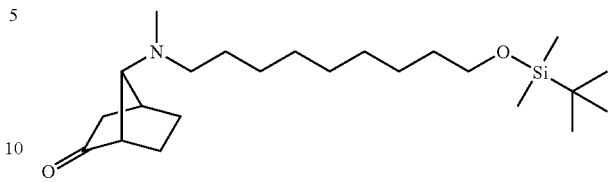

d. (1S,4S,7S)-7-{[9-(tert-Butyl-dimethyl-silanyloxy)-nonyl]-methyl-amino}-bicyclo[2.2.1]-heptan-2-one To a solution of (1S,4S,7S)-5-bromo-7-{[9-(tertbutyl-dimethyl-silanyloxy)-nonyl]-methyl-amino}-bicyclo[2.2.1]heptan-2-one (1.97 g, 4.2 mmol) and AIBN (70 mg, 0.42 mmol) in dry, degassed toluene (40 mL) under a nitrogen atmosphere was added tri-n-butyltin hydride (1.25 mL, 4.65 mmol) and heated at 80° C. on a preheated sand bath. After 2 h at 80° C. the reaction mixture was concentrated in vacuo and purified by column chromatography over silica gel using a gradient of 1-40% diethyl ether/pentane as eluent. After evaporation of the volatiles the title compound was obtained as a light yellow/brown oil.

Yield: 2.41 g, quantitative (contains butyltin residues).

LC-MS (method 3): Rt 3.10 min, m/z 396 [MH+].

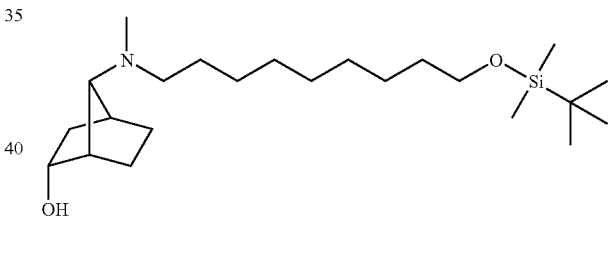

e. (1S,2R,4S,7S)-7-{[9-(tert-Butyldimethylsilanyloxy)nonyl]methylamino}bicyclo[2.2.1]-heptan-2-ol To a solution of (1S,4S,7S)-7-{[9-(tert-butyldimethylsilanyloxy)nonyl]methylamino}-bicyclo[2.2.1]heptan-2-one (4.11 g, 10.4 mmol max) in dry THF (41 mL) at −5° C. under a nitrogen atmosphere was added lithium tri-tert-butoxyaluminum hydride (3.44 g, 13.5 mmol). After 1.5 h at −5° C. more lithium tri-tert-butoxyaluminum hydride (2.64 g, 10.4 mmol) was added. After 1 h at −5° C. the reaction was quenched with satd ammonium chloride solution (aq) and partitioned between ethyl acetate and water. The solids were removed by filtration and washed with ethyl acetate. The phases were separated and the aqueous layer was extracted with ethyl acetate. The combined organic layers were washed with satd NaHCO$_3$ (aq), brine, dried (Na$_2$SO$_4$), filtered, and concentrated to dryness to afford a turbid yellow oil. The crude product was purified by column chromatography over silica gel using a gradient of 7.5-10% MeOH/DCM as eluent. After evaporation of the volatiles a light yellow/brown viscous oil was obtained.

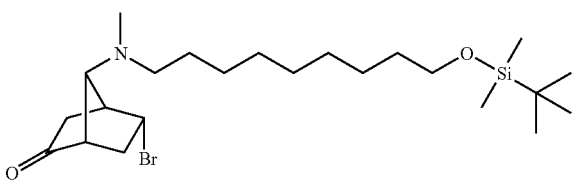

Yield: 2.36 g, 57%.
LC-MS (method 2): Rt 2.95 min, m/z 398 [MH+].

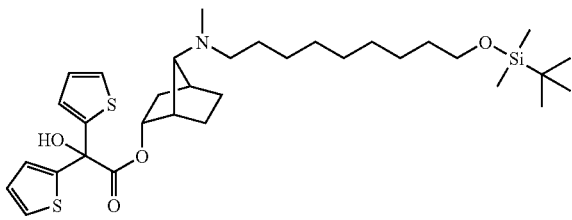

f. Hydroxy-di-thiophen-2-yl-acetic acid (1S,2R,4S, 7S)-7-{[9-(tert-butyldimethyl-silanyloxy)nonyl]methylamino}bicyclo[2.2.1]hept-2-yl ester Sodium hydride (254 mg, 60% suspension in mineral oil, 6.35 mmol) was added to a solution of (1S,2R,4S,7S)-7-{[9-(tert-butyldimethylsilanyloxy)nonyl]methylamino}-bicyclo[2.2.1]heptan-2-ol (1.01 g, 2.54 mmol) in dry toluene (20 mL) at 0° C. under a nitrogen atmosphere. As soon as the gas evolution subsided hydroxy-di-thiophen-2-yl-acetic acid ethyl ester (817 mg, 3.04 mmol) was added in portions, and when the gas evolution stopped the reaction mixture was heated at 80° C. on a preheated sand bath. After 2.5 h the reaction mixture was poured onto satd ammonium chloride (aq) and ether. The layers were separated, the aqueous layer extracted with ether, and the combined organic layers were washed with brine, dried (Na$_2$SO$_4$), filtered, and concentrated to dryness to afford a light brown viscous oil. The crude product was purified by column chromatography over silica gel using a gradient of 1-40% ethyl acetate in DCM as eluent to afford the product as a very light brown viscous oil.

Yield: 0.76 g, 48%.
LC-MS (method 3): Rt 3.44 min, m/z 620 [MH+].

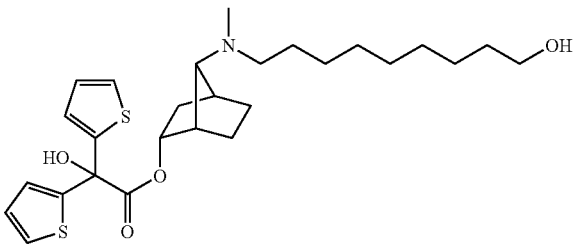

a. Hydroxy-di-thiophen-2-yl-acetic acid (1S,2R,4S, 7S)-7-[(9-hydroxy-nonyl)-methyl-amino]-bicyclo [2.2.1]hept-2-yl ester A solution of hydroxy-di-thiophen-2-yl-acetic acid (1S, 2R,4S,7S)-7-{[9-(tert-butyl-dimethyl-silanyloxy)-nonyl]-methyl-amino}-bicyclo[2.2.1]hept-2-yl ester (0.51 g, 0.82 mmol) in THF (7 mL) was treated with 1 M HCl (3.5 mL) and stirred at RT for 45 min. The reaction mixture was neutralised with satd NaHCO$_3$ (aq) and extracted with ethyl acetate. The combined organic layers were dried (Na$_2$SO$_4$), filtered, and concentrated to dryness to afford a light brown oil, which was used without further purification.

Yield: 273 mg, 66%.
LC-MS (method 3): Rt 2.39 min, m/z 506 [MH+].

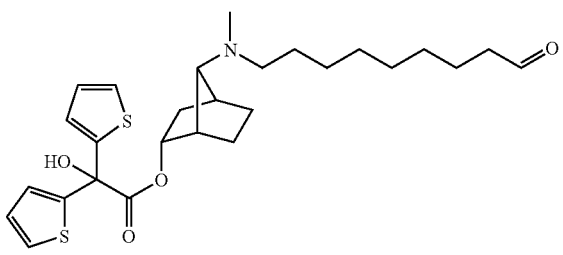

h. Hydroxy-di-thiophen-2-yl-acetic acid (1S,2R,4S, 7S)-7-[methyl-(9-oxo-nonyl)-amino]-bicyclo[2.2.1] hept-2-yl ester Dess-Martin periodinane (450 mg, 1.06 mmol) was added to a solution of hydroxy-di-thiophen-2-yl-acetic acid (1S,2R, 4S,7S)-7-[(9-hydroxy-nonyl)-methyl-amino]-bicyclo[2.2.1] hept-2-yl ester (370 mg, 0.732 mmol) in dry DCM (3 mL) at 0° C., and the reaction mixture allowed to warm to RT. After 1 h at RT the reaction mixture was treated with satd NaHCO$_3$ (aq) and extracted with ethyl acetate. The organic layer was washed with brine, dried (Na$_2$SO$_4$), filtered, and concentrated to dryness. The residue was triturated with ether, and the solids removed by filtration. The filtrate was concentrated to afford an orange/brown viscous oil and used directly without further purification.

Yield: 456 mg, 0.73 mmol max.

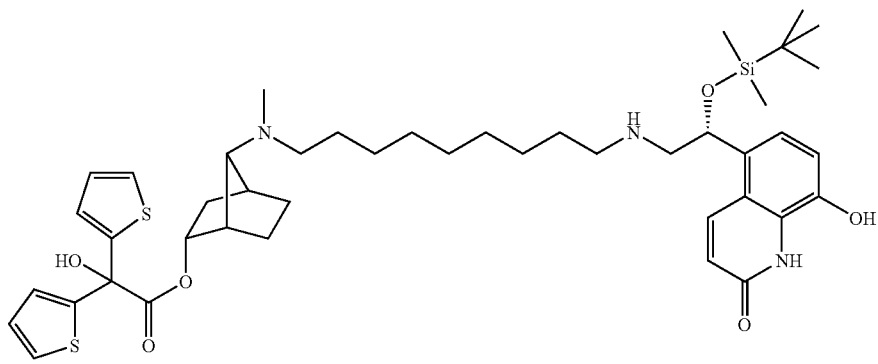

i. Hydroxy-di-thiophen-2-yl-acetic acid (1S,2R,4S, 7S)-7-({9-[(R)-2-(tert-butyldimethyl-silanyloxy)-2-(8-hydroxy-2-oxo-1,2-dihydroquinolin-5-yl)ethylamino]nonyl}methyl-amino)bicyclo[2.2.1]hept-2-yl ester A mixture of hydroxy-di-thiophen-2-yl-acetic acid (1S, 2R,4S,7S)-7-[methyl-(9-oxo-nonyl)amino]bicyclo[2.2.1] hept-2-yl ester (max 0.73 mmol), 5-[(R)-2-amino-1-(tert-butyldimethylsilanyloxy)ethyl]-8-hydroxy-1H-quinolin-2-one (245 mg, 0.73 mmol), sodium triacetoxyborohydride (186 mg, 0.88 mmol), and acetic acid (2 drops) in dry 1,2-dichloroethane was stirred at ambient temperature overnight. The reaction mixture was partitioned between DCM and satd NaHCO₃ (aq). The organic layer was dried (Na₂SO₄), filtered, and concentrated in vacuo to afford a dark green/brown gum that solidified on standing, which was purified by preparative HPLC (system 2, 35% B+1% B/min). The fractions containing pure product were concentrated, neutralised with satd NaHCO₃ (aq), and extracted with DCM. After concentration in vacuo a green/brown oil was obtained.

Yield: 72 mg, 12%.

LC-MS (method 3): Rt 2.51 min, m/z 822 [MH+].

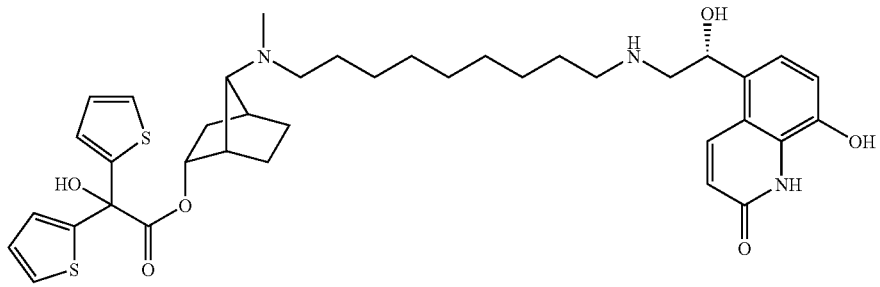

j. Hydroxy-di-thiophen-2-yl-acetic acid (1S,2R,4S, 7S)-7-({9-[(R)-2-hydroxy-2-(8-hydroxy-2-oxo-1,2-dihydro-quinolin-5-yl)-ethylamino]-nonyl}-methyl-amino)-bicyclo[2.2.1]hept-2-yl ester.

A solution of hydroxy-di-thiophen-2-yl-acetic acid (1S, 2R,4S,7S)-7-({9-[(R)-2-(tert-butyldimethylsilanyloxy)-2-(8-hydroxy-2-oxo-1,2-dihydro-quinolin-5-yl)ethylamino]-nonyl}methylamino)bicyclo[2.2.1]hept-2-yl ester (72 mg, 0.087 mmol) and triethylamine trihydrofluoride (60 μL, 0.37 mmol) was stirred in THF/DCM (1:1, 2 mL) at ambient temperature overnight. The reaction mixture was neutralised with satd NaHCO₃ (aq) and extracted with DCM. The organic layer was concentrated to dryness to afford a green/brown oil, which was purified by preparative HPLC (system 1, 15% B+1% B/min for 20 min, then 6% B/min for 10 min). The fractions containing pure product were concentrated, neutralised with satd NaHCO₃ (aq), and extracted with THF. After concentration in vacuo a light brown oil was obtained.

Yield: 50 mg, 81%.

LC-MS (method 3): Rt 2.04 min, m/z 708 [MH+].

EXAMPLE 42

(Benzylcarbamoyl-methyl)-anti-[(1S,2R)-2-(2-hydroxy-2,2-di-thiophen-2-yl-acetoxy)-bicyclo[2.2.1] hept-7-yl]-dimethyl-ammonium bromide

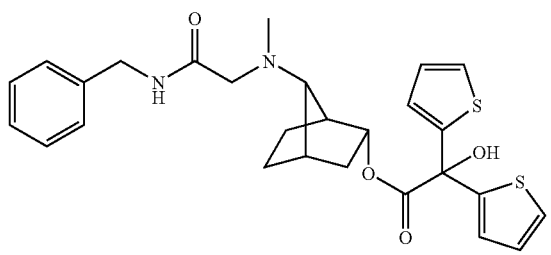

a. Hydroxy-di-thiophen-2-yl-acetic acid anti-(1S, 2R)-7-[(benzylcarbamoyl-methyl)-methyl-amino]-bicyclo[2.2.1]hept-2-yl ester A solution of anti-hydroxy-di-thiophen-2-yl-acetic acid (1S,2R)-7-methylamino-bicyclo[2.2.1]hept-2-yl ester (50 mg, 0.14 mmol) was formed in acetonitrile (3 mL). DIPEA (49 μL, 0.28 mmol) and N-benzyl-2-bromo-acetamide (48 mg, 0.21 mmol) were added and the mixture stirred at 50° C. for 2 hours. The solvent was evaporated and purified by flash column chromatography over silica gel using a gradient of 0-10% ethyl acetate in DCM as eluent to give the title compound as a pale yellow oil (60 mg, 84%): LCMS (method 2): Rt 2.83 mins, m/z 511 [MH+].

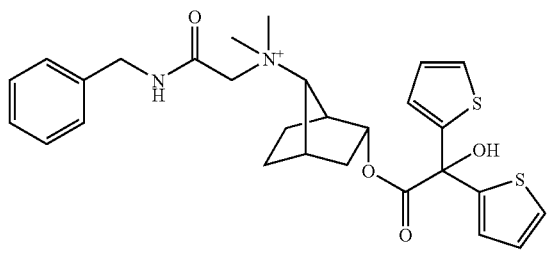

b. (Benzylcarbamoyl-methyl)-anti-[(1S,2R)-2-(2-hydroxy-2,2-di-thiophen-2-yl-acetoxy)-bicyclo[2.2.1]hept-7-yl]-dimethyl-ammonium bromide The title compound was prepared from hydroxy-dithiophen-2-yl-acetic acid anti-(1S,2R)-7-[(benzylcarbamoylmethyl)methylamino]bicyclo[2.2.1]hept-2-yl ester using a method analogous to that described in example 13: LCMS (method 4): Rt 7.53 mins, m/z 525 [M+]; (CDCl₃) δ 1.12 (1H, dd), 1.45-1.52 (1H, m), 1.63 (1H, m), 1.72-1.80 (1H, m), 1.88-1.97 (1H, m), 2.28 (1H, m), 2.74 (1H, br, t), 3.06 (1H, br t), 3.34 (3H, s), 3.36 (3H, s), 4.17 (1H, s), 4.41 (2H, d), 4.68 (2H, dd), 4.79 (1H, s), 5.60 (1H, m), 6.98 (2H, m), 7.15 (2H, m), 7.19-7.23 (1H, m), 7.25-7.31 (4H, m), 7.36 (2H, d), 9.55 (1H, t).

The following example was prepared in a similar manner to that described for example 42.

drous THF (10 mL) was stirred at ambient temperature under a nitrogen atmosphere with sodium hydride (145 mg of 60% dispersion in oil) for 3 hours. Oxo-phenyl-acetyl chloride (611 mg, 3.64 mmol) was added and the reaction allowed to stand for 60 hours. The reaction was quenched by addition of satd NH₄Cl, extracted into EtOAc and the combined organic extracts washed with brine, dried over MgSO₄ and concentrated in vacuo. The reaction was purified by chromatography on silica using a gradient of 0-5% Et₂O-cyclohexane as eluent to give the product as a yellow oil (600 mg). (CDCl₃) δ 1.20-1.30 (2H, m), 1.63-1.71 (2H, m), 1.78-1.88 (1H, m), 1.88-1.96 (2H, m), 2.14-2.25 (5H, m), 2.35-2.37 (1H, m), 2.50-2.58 (2H, m), 2.66-2.70 (1H, m), 3.97-4.03 (2H, m), 5.20-5.26 (1H, m), 6.85-6.95 (3H, m), 7.24-7.30 (2H, m), 7.48-7.54 (2H, m), 7.63-7.69 (2H, m), 7.95-8.00 (2H, m).

| Ex. | Name | Structure | ¹H NMR (400 MHz) | Rt/min (Method 4); [MH]+ or [M]+ |
|---|---|---|---|---|
| 43 | [2-(2,3-Dihydro-benzofuran-5-yl)-ethyl]-anti-[(1S,2R)-2-(2-hydroxy-2,2-di-thiophen-2-yl-acetoxy)-bicyclo[2.2.1]hept-7-yl]-dimethyl-ammonium bromide | 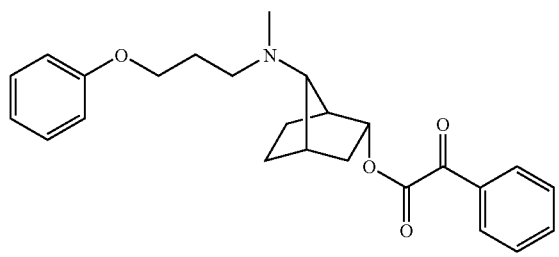 | (CDCl₃) δ 1.16(1H, dd), 1.46-1.54(1H, m), 1.68-1.75(2H, m), 1.90-1.99(1H, m), 2.45 (1H, m), 2.76(1H, s), 3.05-3.11(3H, m), 3.16(2H, t), 3.39(3H, s), 3.41(3H, s), 3.86(2H, m), 4.17(1H, s), 4.52(2H, t), 4.81(1H, s), 5.16 (1H, m), 6.69(1H, d), 6.97 (2H, m), 7.03(1H, d), 7.15 (2H, dd), 7.24-7.30(3H, m). | 7.39; 524 |

EXAMPLE 44 anti-(1S,2R) [2-(2-Cyclohexyl-2-hydroxy-2-phenyl-acetoxy)-bicyclo[2.2.1]hept-7-yl]-dimethyl-(3-phenoxy-propyl)-ammonium bromide

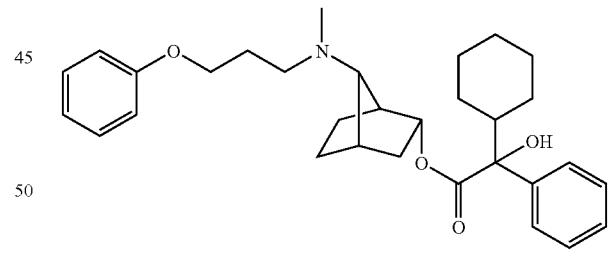

a. anti-(1S,2R) Cyclohexyl-hydroxy-phenyl-acetic acid 7-[methyl-(3-phenoxypropyl)-amino]-bicyclo[2.2.1]hept-2-yl ester To a stirred solution of anti-(1S,2R) oxo-phenyl-acetic acid 7-[methyl-(3-phenoxy-propyl)-amino]-bicyclo[2.2.1]hept-2-yl ester (200 mg, 0.49 mmol) in anhydrous THF (5 mL) under a nitrogen atmosphere was added cyclohexylmagnesium chloride (0.5 mL, 0.98 mmol). The reaction was warmed at 50° C. for 18 hours. The cooled reaction was quenched by addition of satd NH₄Cl, extracted into EtOAc and the combined organic extracts dried over MgSO₄ and concentrated in vacuo. The reaction was purified by chromatography on silica a. anti-(1S,2R) Oxo-phenyl-acetic acid 7-[methyl-(3-phenoxy-propyl)-amino]-bicyclo[2.2.1]hept-2-yl ester A solution of anti-(1S,2R) 7-[methyl-(3-phenoxy-propyl)amino]bicyclo[2.2.1]heptan-2-ol (0.77 g, 2.8 mmol) in anhyusing a gradient of 5-10% Et$_2$O-cyclohexane as eluent to give the product as a clear oil (123 mg). LCMS (method 1): Rt 2.86 mins, m/z 492 [MH+].

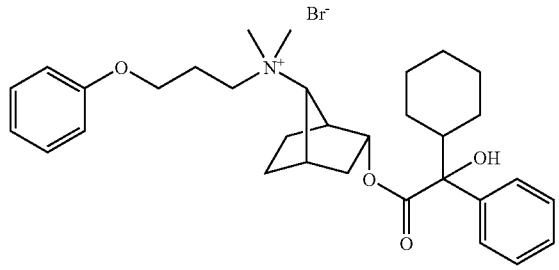

c. anti-(1S,2R) [2-(2-Cyclohexyl-2-hydroxy-2-phenyl-acetoxy)-bicyclo[2.2.1]hept-7-yl]dimethyl-(3-phenoxy-propyl)-ammonium bromide The title compound was prepared from anti-(1S,2R) cyclohexyl-hydroxy-phenyl-acetic acid 7-[methyl-(3-phenoxypropyl)-amino]-bicyclo[2.2.1]hept-2-yl ester using procedures outlined in example 13. LCMS (method 1): Rt 2.75 mins, m/z 506 [M+].

EXAMPLE 45 anti-(1S,2R) 2-Hydroxy-3,3-dimethyl-2-phenyl-butyric acid 7-[methyl-(3-phenoxy-propylamino]bicyclo[2.2.1]hept-2-yl ester

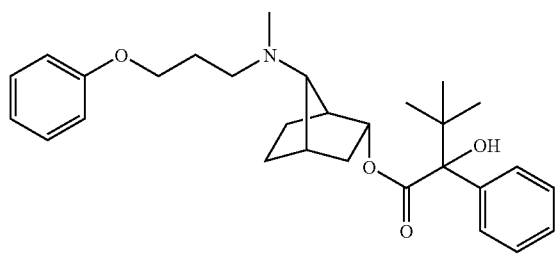

The title compound was prepared from anti-(1S,2R) oxo-phenyl-acetic acid 7-[methyl-(3-phenoxy-propyl)-amino]-bicyclo[2.2.1]hept-2-yl ester using procedures outlined in example 44. (CDCl$_3$) δ 0.97-1.05 (9H, s), 1.07-1.28 (2H, m), 1.68-1.79 (2H, m), 1.81-1.96 (3H, m), 2.1-2.24 (5H, m), 2.31 (1H, s), 2.49-2.61 (3H, m), 3.80 (1H, s), 3.97-4.03 (2H, m), 5.02-5.11 (1H, m), 6.86-6.95 (3H, m), 7.23-7.34 (5H, m), 7.69-7.74 (2H, m). LCMS (method 4): Rt 8.29 mins, m/z 466 [MH+].

EXAMPLE 46 anti-(1S,2R) [2-(2-tert-Butyl-2-hydroxy-2-phenyl-acetoxy)-bicyclo[2.2.1]hept-7yl]-dimethyl-(3-phenoxy-propyl)-ammonium bromide

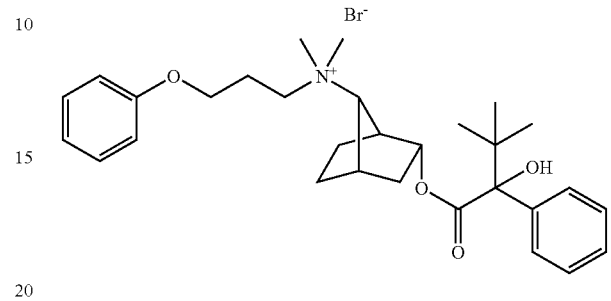

The title compound was prepared from anti-(1S,2R) 2-hydroxy-3,3-dimethyl-2-phenyl-butyric acid 7-[methyl-(3-phenoxy-propylamino]bicyclo[2.2.1]hept-2-yl ester using procedures described in example 13. LCMS (method 2) Rt 2.82 mins, m/z 480 [M+].

EXAMPLE 47

[anti-(1R,2R)-2-(2-Hydroxy-2,2-diphenyl-acetylamino)-bicyclo[2.2.1]hept-7-yl]-dimethyl-(3-phenoxy-propyl)-ammonium bromide

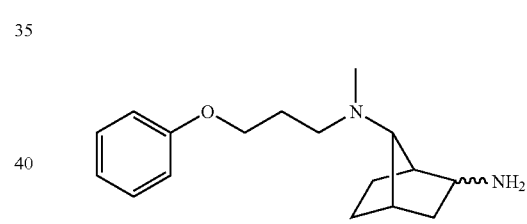

a. (1R,7S)—N$^7$-Methyl-N$^7$-(3-phenoxy-propyl)-bicyclo[2.2.1]heptane-2,7-diamine A solution of (1S,7S)-7-[methyl-(3-phenoxy-propyl)-amino]-bicyclo[2.2.1]heptan-2-one (1.35 g, 4.9 mmol) was formed in methanol (90 mL). Sodium acetate (648 mg, 7.9 mmol) was added followed by hydroxylamine hydrochloride (566 mg, 8.2 mmol). The mixture was stirred at room temperature for 18 hours. Nickel (II) chloride hexahydrate (2.11 g, 8.9 mmol) was added followed by portionwise addition of sodium borohydride (1.68 g, 44.5 mmol). The mixture was stirred at room temperature for a further 18 hours. The solvent was removed under reduced pressure and the residue partitioned between ethyl acetate and aqueous sodium hydroxide. The organic phase was dried over sodium sulphate, filtered and evaporated to a gum. This was loaded onto an SCX cartridge, washed with methanol and then eluted with 4M ammonia in methanol. The material was further purified by column chromatography over silica gel using a gradient of 0-10% methanol in DCM as eluent to give the title compound as a brown oil (526 mg, 39%). LCMS (method 2): Rt 0.34 mins, m/z 275 [MH+].

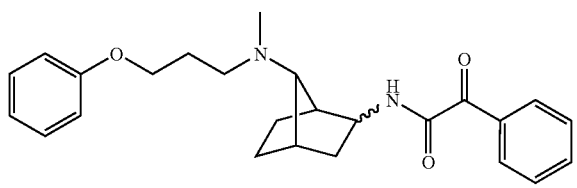

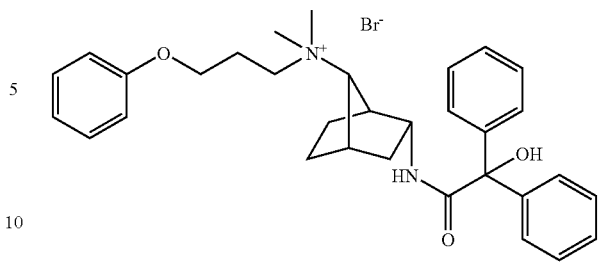

b. N-{(1R,7S)-7-[Methyl-(3-phenoxy-propyl)-amino]-bicyclo[2.2.1]hept-2-yl}-2-oxo-2-phenyl-acetamide A solution of (1R,7S)—N$^7$-methyl-N$^7$-(3-phenoxy-propyl)-bicyclo[2.2.1]heptane-2,7-diamine (200 mg, 0.73 mmol) was formed in DCM (3 mL) with diisopropylethylamine (0.25 mL, 1.46 mmol). A solution of oxo-phenyl-acetyl chloride (184 mg, 1.09 mmol) in DCM (1 mL) was added dropwise. The mixture was stirred at room temperature for 3 hours. The solvent was evaporated and the residue purified by chromatography over silica gel using a gradient of 0-20% ethyl acetate in DCM to give the title compound as a colourless oil (150 mg, 51%). LCMS (method 2): Rt 2.28 mins, m/z 407 [MH+].

d. [anti-(1R,2R)-2-(2-Hydroxy-2,2-diphenyl-acetylamino)-bicyclo[2.2.1]hept-7-yl]-dimethyl-(3-phenoxy-propyl)-ammonium bromide The title compound was prepared from 2-hydroxy-N-{anti-(1R,2R)-7-[methyl-(3-phenoxy-propyl)-amino]-bicyclo[2.2.1]hept-2-yl}-2,2-diphenyl-acetamide using a method analogous to that in example 13: LCMS (method 1): Rt 7.88 mins, 499 m/z [M+]; (CD$_3$OD) δ 1.27 (1H, m), 1.66-1.75 (1H, m), 1.85 (2H, t), 2.05 (1H, m), 2.22-2.38 (3H, m), 2.73 (1H, m), 3.00 (1H, s), 3.20 (6H, s), 3.60-3.68 (3H, m), 4.11 (3H, m), 6.92-6.96 (3H, m), 7.25-7.34 (8H, m), 7.40-7.45 (4H, m).

EXAMPLE 48

Hydroxy-di-thiophen-2-yl-acetic acid anti-(1S,2R)-7-[(3-dimethylamino-propyl)-methyl-amino]-bicyclo[2.2.1]hept-2-yl ester

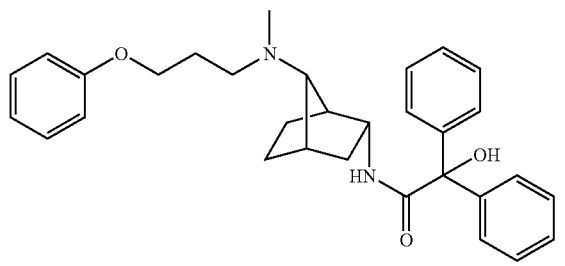

c. 2-Hydroxy-N-{anti-(1R,2R)-7-[methyl-(3-phenoxy-propyl)-amino]-bicyclo[2.2.1]hept-2-yl}-2,2-diphenyl-acetamide A cooled (0° C.) solution of N-{(1R,7S)-7-[methyl-(3-phenoxy-propyl)-amino]-bicyclo[2.2.1]hept-2-yl}-2-oxo-2-phenyl-acetamide (100 mg, 0.25 mmol) was formed in THF (5 mL). A solution of phenyl magnesium chloride (0.26 mL, 2M in THF, 0.52 mmol) was added and the solution stirred for 1 hour at 0° C. then allowed to warm to room temperature for a further 1 hour. The reaction was quenched by the addition of aqueous ammonium chloride (sat. 10 mL). The mixture was extracted with ethyl acetate then the combined organics were dried over sodium sulphate, filtered and evaporated. Purification by chromatography over silica gel using a gradient of 0-5 methanol in DCM gave the title compound as a colourless oil (20 mg, 17%). LCMS (method 2): Rt 2.55 mins, 485 m/z [MH+].

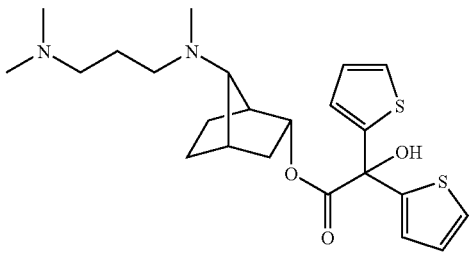

The title compound was formed from anti-hydroxy-di-thiophen-2-yl-acetic acid (1S,2R)-7-methylamino-bicyclo[2.2.1]hept-2-yl ester and (3-Methanesulfonyloxy-propyl)-dimethyl-ammonium chloride using a method analogous to that in example 42: LCMS (method 1): Rt 5.02 mins, 449 m/z [MH+]; (CD$_3$OD) δ 1.07-1.18 (2H, m), 1.50 (2H, m), 1.77 (3H, m), 2.10 (1H, m), 2.17 (3H, s), 2.32 (1H, s), 2.42 (2H, t), 2.54 (1H, s), 2.61 (6H, s), 2.79 (2H, m), 4.57 (1H, br s), 5.02 (1H, m), 6.98 (2H, m), 7.14 (2H, m), 7.38 (2H, m).

EXAMPLE 49

(3-Dimethylamino-propyl)-[anti-(1S,2R)-2-(2-hydroxy-2,2-di-thiophen-2-yl-acetoxy)-bicyclo[2.2.1]hept-7-yl]-dimethyl-ammonium bromide

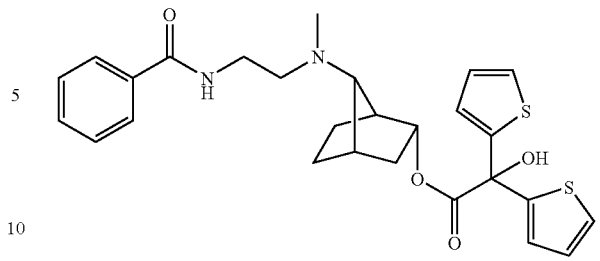

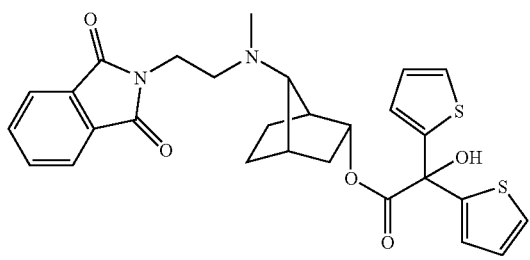

a. Hydroxy-di-thiophen-2-yl-acetic acid anti-(1S, 2R)-7-{[2-(1,3-dioxo-1,3-dihydro-isoindol-2-yl)-ethyl]-methyl-amino}-bicyclo[2.2.1]hept-2-yl ester The title compound was formed from anti-hydroxy-di-thiophen-2-yl-acetic acid (1S,2R)-7-methylamino-bicyclo[2.2.1]hept-2-yl ester and N-(2-bromoethyl)phthalimide using a method analogous to that in example 42. LCMS (method 2): Rt 2.70 mins, 537 m/z [MH+].

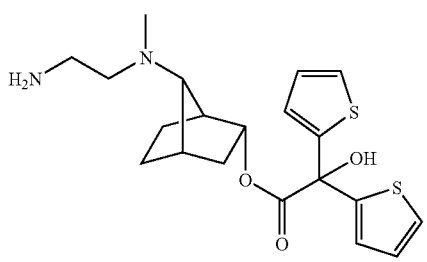

b. Hydroxy-di-thiophen-2-yl-acetic acid anti-(1S, 2R)-7-[(2-amino-ethyl)-methyl-amino]-bicyclo[2.2.1]hept-2-yl ester A solution of hydroxy-di-thiophen-2-yl-acetic acid anti-(1S,2R)-7-{[2-(1,3-dioxo-1,3-dihydro-isoindol-2-yl)-ethyl]-methyl-amino}-bicyclo[2.2.1]hept-2-yl ester (80 mg, 0.15 mmol) was formed in ethanol (3 mL). Hydrazine monohydrate (72 µL, 1.49 mmol) was added and the mixture heated at 80° C. for 1 hour then allowed to cool to room temperature. The resulting white precipitate was filtered and the filter washed with ethanol. The filtrate was evaporated to give crude title compound: LCMS (method 3): Rt 2.03 mins, 407 m/z [MH+].

c. Hydroxy-di-thiophen-2-yl-acetic acid anti-(1S, 2R)-7-[(2-benzoylamino-ethyl)-methyl-amino]-bicyclo[2.2.1]hept-2-yl ester The crude hydroxy-di-thiophen-2-yl-acetic acid anti-(1S, 2R)-7-[(2-amino-ethyl)-methyl-amino]-bicyclo[2.2.1]hept-2-yl ester (0.15 mmol) was dissolved in DCM (5 mL). Diisopropylethylamine (31 pt, 0.23 mmol) was added followed by benzoyl chloride (17 µL, 0.15 mmol). The mixture was stirred at room temperature for 30 mins. Water (5 mL) was added and the organics isolated through a phase-separation cartridge and evaporated. Purification by chromatography over silica gel using a gradient of 0-20% ethyl acetate in DCM as eluent gave the title compound as a colourless oil (30 mg, 39%). LCMS (method 3): Rt 2.47 mins, 511 m/z [MH+].

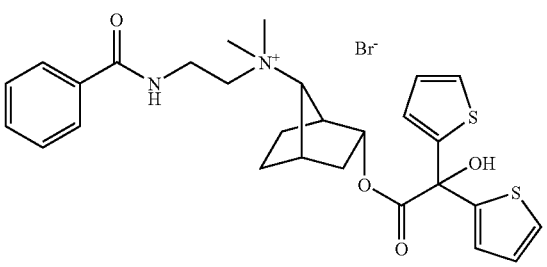

d. (2-Benzoylamino-ethyl)-anti-[(1S,2R)-2-(2-hydroxy-2,2-di-thiophen-2-yl-acetoxy)-bicyclo[2.2.1]hept-7-yl]-dimethyl-ammonium bromide The title compound was prepared from hydroxy-di-thiophen-2-yl-acetic acid anti-(1S,2R)-7-[(2-benzoylamino-ethyl)-methyl-amino]-bicyclo[2.2.1]hept-2-yl ester using a method analogous to that in example 13: LCMS (method 1): Rt 7.25 mins, m/z 525 [M+]; (CD$_3$OD) δ 1.18 (1H, dd), 1.47-1.55 (1H, m), 1.74-1.90 (2H, m), 1.99-2.09 (1H, m), 2.31 (1H, m), 2.80 (1H, m), 3.12 (1H, m), 3.27 (3H, s), 3.27 (3H, s), 3.64-3.69 (3H, m), 3.89 (2H, t), 5.09 (1H, m), 7.00 (2H, m), 7.14 (2H, m), 7.40 (2H, m), 7.45-7.50 (2H, m), 7.54-7.58 (1H, m), 7.85-7.88 (2H, m).

BIOLOGICAL EXAMPLES

The inhibitory effects of compounds of the present invention at the M3 muscarinic receptor and (in the case of Example 41) the β$_2$ adrenergic receptor, were determined by the following binding assays:

Muscarinic Receptor Radioligand Binding Assays

Radioligand binding studies utilising [$^3$H]-N-methyl scopolamine ([$^3$H]-NMS) and commercially available cell membranes expressing the human muscarinic receptors (M2 and M3) were used to assess the affinity of muscarinic antagonists for M2 and M3 receptors. Membranes in TRIS buffer were incubated in 96-well plates with [$^3$H]-NMS and M3 antagonist at various concentrations for 3 hours. Membranes and bound radioligand were then harvested by filtration and allowed to dry overnight. Scintillation fluid was then added and the bound radioligand counted using a Canberra Packard Topcount scintillation counter.

The half-life of antagonists at each muscarinic receptor was measured using the alternative radioligand [$^3$H]-QNB and an adaptation of the above affinity assay. Antagonists were incubated for 3 hours at a concentration 10-fold higher than their Ki, as determined with the [$^3$H]-QNB ligand, with membranes expressing the human muscarinic receptors. At the end of this time, [$^3$H]-QNB was added to a concentration 25-fold higher than its Kd for the receptor being studied and the incubation continued for various time periods from 15 minutes up to 180 minutes. Membranes and bound radioligand were then harvested by filtration and allowed to dry overnight. Scintillation fluid was then added and the bound radioligand counted using a Canberra Packard Topcount scintillation counter.

The rate at which [3H]-QNB is detected binding to the muscarinic receptors is related to the rate at which the antagonist dissociates from the receptor, ie, to the half life of the antagonists on the receptors.

Results:

| Example | Binding potency |
|---------|-----------------|
| 1 | +++ |
| 2 | +++ |
| 3 | ++ |
| 4 | ++ |
| 5 | +++ |
| 6 | ++ |
| 7 | ++ |
| 8 | ++ |
| 9 | + |
| 10 | + |
| 11 | +++ |
| 12 | +++ |
| 13 | +++ |
| 14 | + |
| 15 | + |
| 16 | ++ |
| 17 | +++ |
| 18 | ++ |
| 19 | +++ |
| 20 | +++ |
| 21 | +++ |
| 22 | +++ |
| 23 | + |
| 24 | +++ |
| 25 | +++ |
| 26 | +++ |
| 27 | ++ |
| 28 | + |
| 29 | + |
| 30 | + |
| 31 | + |
| 32 | + |
| 33 | +++ |
| 34 | ++ |
| 35 | ++ |
| 36 | +++ |
| 37 | +++ |
| 38 | +++ |
| 39 | + |
| 40 | + |
| 41 | +++ |
| 42 | +++ |

| Example | Binding potency |
|---------|-----------------|
| 43 | +++ |
| 44 | NT |
| 45 | + |
| 46 | NT |
| 47 | NT |
| 48 | NT |
| 49 | NT |

In the table above, M3 binding potencies (Ki values) are indicated as follows: <1 nM '+++'; 1-10 nM '++'; >10 nM '+'. All compounds tested exhibited Ki values <5000 nM. NT = Not Tested.

β-Adrenergic Receptor Radioligand Binding Assay

Radioligand binding studies utilising [$^{125}$I]-Iodocyanopindolol and commercially available cell membranes expressing the human $β_2$ adrenergic receptor were used to assess the affinity of antagonists for $β_2$-adrenergic receptor. Membranes and SPA-beads were incubated with [$^{125}$I]-Iodocyanopindolol and $β_2$ antagonist at various concentrations for 3 hours at ambient temperature in TRIS buffer. The assay was performed in 96-well plates which were read using the Wallac Microbeta counter. Example 41 exhibited a $K_i$ value of <100 nM in this assay.

Analysis of Inhibition of M3 Receptor Activation Via Calcium Mobilization

IN an alternative M3 receptor binding assay, CHO cells expressing the human M3 receptor were seeded and incubated overnight in 96 well collagen coated plates (black-wall, clear bottom) at a density of 50000/75 μL of medium in 3% serum. The following day, a calcium-sensitive dye (Molecular Devices, Cat #R8041) was prepared in HBSS buffer with the addition of 5 mM probenecid (pH 7.4). An equal volume of the dye solution (75 μL) was added to the cells and incubated for 45 minutes followed by addition of 50 μL of muscarinic antagonists or vehicle. After a further 15 minutes the plate was read on a FLEXstation™ (excitation 488 nm, emission 525 nm) for 15 seconds to determine baseline fluorescence. The muscarinic agonist Carbachol was then added at an $EC_{80}$ concentration and the fluorescence measured for a further 60 seconds. The signal was calculated by subtracting the peak response from the mean of the baseline fluorescence in control wells in the absence of antagonist. The percentage of the maximum response in the presence of antagonist was then calculated in order to generate $IC_{50}$ curves.

The inhibitory effects of compounds of the present invention at the M3 muscarinic Receptor may be evaluated in the following ex-viva and in vivo assays:

Evaluation of Potency and Duration of Action in Isolated Guinea Pig Trachea

Experiments were carried out at 37° C. in modified Krebs-Henseleit solution, (114 mM NaCl, 15 mM NaHCO$_3$, 1 mM MgSO$_4$, 1.3 mM CaCl$_2$, 4.7 mM KCl, 11.5 mM glucose and 1.2 mM KH$_2$PO$_4$, pH 7.4) gassed with 95% O$_2$/5% CO$_2$. Indomethacin was added to a final concentration of 3 μM Tracheae were removed from adult male Dunkin Hartley Guinea pigs and dissected free of adherent tissue before being cut open longitudinally in a line opposite the muscle. Individual strips of 2-3 cartilage rings in width were cut and suspended using cotton thread in 10 ml water-jacketed organ baths and attached to a force transducer ensuring that the tissue is located between two platinum electrodes. Responses were recorded via a MP100W/Acknowledge data acquisition system connected to a PC. Tissues were equilibrated for one hour under a resting tone of 1 g and were then subjected to electrical field stimulation at a frequency of 80 Hz with a pulse width of 0.1 ms, a unipolar pulse, triggered every 2 minutes. A "voltage-response" curve was generated for each tissue and a submaximal voltage then applied to every piece of tissue according to its own response to voltage. Tissues were washed with Krebs solution and allowed to stabilize under stimulation prior to addition of test compound. Concentration response curves were obtained by a cumulative addition of test compound in half-log increments. Once the response to each addition had reached a plateau the next addition was made. Percentage inhibition of EFS-stimulated contraction is calculated for each concentration of each compound added and dose response curves constructed using Graphpad Prism software and the $EC_{50}$ calculated for each compound.

Onset time and duration of action studies were performed by adding the previously determined $EC_{50}$ concentration of compound to EFS contracted tissues and the response allowed to plateau. The time taken to reach 50% of this response was determined to be the onset time. Tissues were then washed free of compound by flushing the tissue bath with fresh Krebs solution and the time taken for the contraction in response to EFS to return to 50% of the response in the presence of compound is measured. This is termed the duration of action. By way of example, in this assay the compound of Example 20 had an $EC_{50}$ of 0.8 nM and a duration of action of 540 minutes.

Methacholine Induced Bronchoconstriction In Vivo

Male Guinea pigs (Dunkin Hartley), weighing 500-600 g housed in groups of 5 were individually identified. Animals were allowed to acclimatize to their local surroundings for at least 5 days. Throughout this time and study time animals were allowed access to water and food ad libitum.

Guinea pigs were anaesthetized with the inhaled anaesthetic Halothane (5%). Test compound or vehicle (0.25-0.50 mL/kg) was administered intranasally. Animals were placed on a heated pad and allowed to recover before being returned to their home cages.

Up to 24 hrs post dosing guinea pigs were terminally anaesthetized with Urethane (250 µg/mL, 2 mL/kg). At the point of surgical anaesthesia, the jugular vein was cannulated with a portex i.v. cannula filled with heparinised phosphate buffered saline (hPBS) (10 U/mL) for i.v. administration of methacholine. The trachea was exposed and cannulated with a rigid portex cannula and the oesophagus cannulated transorally with a flexible portex infant feeding tube.

The spontaneously breathing animal was then connected to a pulmonary measurement system (EMMS, Hants, UK) consisting of a flow pneumotach and a pressure transducer. The tracheal cannula was attached to a pneumotach and the oesophageal cannula attached to a pressure transducer.

The oesophageal cannula was positioned to give a baseline resistance of between 0.1 and 0.2 cmH20/mL/s. A 2 minute baseline reading was recorded before i.v. administration of methacholine (up to 30 µg/kg, 0.5 mL/kg). A 2 minute recording of the induced constriction was taken from the point of i.v. administration.

The software calculated a peak resistance and a resistance area under the curve (AUC) during each 2 minute recording period which was used to analyse the bronchoprotective effects of test compounds. The results obtained in this assay for the compound of Example 20 (0.1, 0.3 and 1 µg/kg i.n.) 4 hours prior to MCh (10 µg/kg i.v.) induced bronchoconstriction, and the comparator compound tiotropium, are shown in FIG. 1.

The invention claimed is:

1. A compound which is an anti-[(1S, 2R) 2-(9-Hydroxy-9H-xanthene-9-carbonyloxy)-bicyclo[2.2.1]hept-7-yl]-dimethyl-(3-phenoxy-propyl)-ammonium salt.

2. A pharmaceutical composition, wherein said composition comprises a compound of claim 1 and a pharmaceutically acceptable carrier or excipient.

3. A pharmaceutical composition as claimed in claim 2, wherein said composition is in a form suitable for inhalation.

4. A method of treating chronic obstructive lung disease, chronic bronchitis or asthma, wherein said method comprises administering to a subject in need thereof an effective amount of a compound as claimed in claim 1.

5. A compound as claimed in claim 1, wherein said compound is a chloride, bromide, sulfate, methanesulfonate, benzenesulfonate, toluenesulfonate, phosphate, acetate, citrate, lactate, tartrate, mesylate, maleate, fumarate, or succinate salt.

6. A compound as claimed in claim 5, wherein said compound is anti-[(1S,2R) 2-(9-Hydroxy-9H-xanthene-9-carbonyloxy)-bicyclo[2.2.1]hept-7-yl]-dimethyl-(3-phenoxy-propyl)-ammonium bromide.

7. A pharmaceutical composition, wherein said composition comprises the compound of claim 6 and a pharmaceutically acceptable carrier or excipient.

8. A pharmaceutical composition as claimed in claim 7, wherein said composition is in a form suitable for inhalation.

9. A method of treating chronic obstructive lung disease, chronic bronchitis or asthma, wherein said method comprises administering to a subject in need thereof an effective amount of a compound as claimed in claim 6.

* * * * *